(12) United States Patent
Gregerson

(10) Patent No.: US 12,725,347 B2
(45) **Date of Patent: *Sep. 1, 2026**

(54) SYSTEM AND METHOD FOR RECONSTRUCTION OF 3D VOLUMES FROM BIPLANAR RADIOGRAPHIC IMAGES

(71) Applicant: See All AI Inc., Nashua, NH (US)

(72) Inventor: Eugene Alma Gregerson, North Salt Lake, UT (US)

(73) Assignee: See All AI Inc., Nashua, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/265,222

(22) Filed: Jul. 10, 2025

(65) Prior Publication Data

US 2025/0363726 A1 Nov. 27, 2025

Related U.S. Application Data

(63) Continuation of application No. 18/974,545, filed on Dec. 9, 2024, now Pat. No. 12,444,127.

(Continued)

(51) Int. Cl.

| | |
|---|---|
| ***A61B 6/00*** | (2024.01) |
| ***A61B 6/58*** | (2024.01) |

(Continued)

(52) U.S. Cl.

CPC ................ *G06T 15/08* (2013.01); *A61B 6/52* (2013.01); *A61B 6/5205* (2013.01); *A61B 6/582* (2013.01);

(Continued)

(58) Field of Classification Search

CPC .. G06T 15/08; G06T 7/33; G06T 7/73; G06T 11/006; G06T 2207/10116;

(Continued)

(56) References Cited

U.S. PATENT DOCUMENTS

| | | | |
|---|---|---|---|
| 4,559,936 | A | 12/1985 | Hill |
| 6,266,453 | B1 | 7/2001 | Hibbard et al. |

(Continued)

FOREIGN PATENT DOCUMENTS

| | | | |
|---|---|---|---|
| CN | 113628260 | A | 11/2021 |
| JP | 2020-509870 | A | 4/2020 |

(Continued)

OTHER PUBLICATIONS

Jecklin, S. et al., "Domain adaptation strategies for 3D reconstruction of the lumbar spine using real fluoroscopy data," Medical Image Analysis, Aug. 22, 2024, pp. 1-19, vol. 98, 103322, ScienceDirect, Elsevier, https://doi.org/10.1016/j.media.2024. 103322.

(Continued)

*Primary Examiner* — Ali Bayat

(74) *Attorney, Agent, or Firm* — ARENTFOX SCHIFF LLP; Shawn P. Foley; Sean Salimi

(57) ABSTRACT

A system and method combine optical and radiographic data to enhance imaging capabilities. Specifically, the system combines visually obtained patient pose position information and radiographic image information to facilitate calibrated surgical navigation. A reconstruction of a 3D CT volume is generated from biplanar X-ray projections which are back projected into two separate volumes and then concatenated into a single volume along a new dimension and passed through a pretrained deep learning model to decode the concatenated volume into a single 3D volume.

5 Claims, 36 Drawing Sheets

Related U.S. Application Data

(60) Provisional application No. 63/608,122, filed on Dec. 8, 2023, provisional application No. 63/607,956, filed on Dec. 8, 2023.

(51) Int. Cl.
*A61B 34/20* (2016.01)
*G06T 7/33* (2017.01)
*G06T 7/73* (2017.01)
*G06T 12/20* (2026.01)
*G06T 15/08* (2011.01)
*A61B 90/00* (2016.01)

(52) U.S. Cl.
CPC ................ *A61B 34/20* (2016.02); *G06T 7/33* (2017.01); *G06T 7/73* (2017.01); *G06T 12/20* (2026.01); *A61B 2034/2065* (2016.02); *A61B 2090/367* (2016.02); *A61B 2090/376* (2016.02); *A61B 2090/3966* (2016.02); *G06T 2207/10116* (2013.01); *G06T 2207/30204* (2013.01)

(58) Field of Classification Search
CPC . G06T 2207/30204; G06T 2207/10081; G06T 2207/20084; G06T 2211/436; G06T 2211/441; G06T 2210/41; G06T 2219/2004; G06T 19/20; A61B 6/52; A61B 6/5205; A61B 6/582; A61B 34/20; A61B 2034/2065; A61B 2090/367; A61B 2090/376; A61B 2090/3966; A61B 6/032; A61B 2034/2055; A61B 6/12; A61B 6/4405; A61B 6/4441; A61B 6/5223; A61B 6/5235; A61B 6/583; A61B 6/584
USPC .......................................................... 382/131
See application file for complete search history.

(56) References Cited

U.S. PATENT DOCUMENTS 6,569,203 B1 5/2003 Keller
8,232,798 B2 7/2012 Krueger et al.
8,911,447 B2 12/2014 Van et al.
10,258,414 B2 4/2019 O'Grady et al.
10,390,843 B1 8/2019 Henderson
10,709,394 B2 7/2020 Zhou et al.
10,839,543 B2 11/2020 Cheng et al.
10,925,572 B1 2/2021 Chang et al.
11,207,135 B2 12/2021 Schmidt et al.
11,379,985 B2 7/2022 Wang et al.
11,457,883 B1 10/2022 Hartley et al.
12,039,685 B2 * 7/2024 Lavi ...................... A61B 6/463
12,053,247 B1 8/2024 Chiou
12,245,825 B2 * 3/2025 Harris, Jr. ............ A61F 2/4609
12,361,631 B2 7/2025 Gregerson
12,383,219 B2 8/2025 Kovler et al.
12,462,469 B2 11/2025 Gregerson
2002/0103479 A1 8/2002 Sarver
2003/0093080 A1 5/2003 Brown et al.
2003/0130576 A1 7/2003 Seeley et al.
2003/0181809 A1 9/2003 Hall et al.
2004/0015077 A1 1/2004 Sati et al.
2004/0215071 A1 10/2004 Frank et al.
2005/0018891 A1 1/2005 Barfuss et al.
2005/0117708 A1 6/2005 Cho et al.
2005/0148854 A1 7/2005 Ito et al.
2005/0159759 A1 7/2005 Harbaugh et al.
2005/0165479 A1 7/2005 Drews et al.
2005/0228256 A1 10/2005 Labadie et al.
2008/0285843 A1 * 11/2008 Lim .................... G06V 10/145
382/154
2008/0285854 A1 11/2008 Kotake et al.
2008/0317321 A1 12/2008 Zhang et al.
2009/0088622 A1 4/2009 Mostafavi
2009/0123042 A1 5/2009 Gagnon et al.
2009/0207971 A1 8/2009 Uhde et al.
2009/0285366 A1 11/2009 Essenreiter et al.
2010/0249800 A1 9/2010 Kim et al.
2010/0312103 A1 12/2010 Gorek et al.
2011/0255661 A1 10/2011 Schweizer
2012/0163686 A1 6/2012 Liao et al.
2012/0203336 A1 8/2012 Annest
2012/0236993 A1 9/2012 Graumann
2013/0170627 A1 7/2013 Topfer et al.
2014/0050375 A1 2/2014 Baker et al.
2014/0222074 A1 8/2014 Rathbun et al.
2014/0294140 A1 10/2014 Kirby et al.
2015/0018944 A1 1/2015 O'Connell et al.
2015/0216498 A1 8/2015 Schulze et al.
2015/0305823 A1 10/2015 Claus
2016/0242724 A1 8/2016 LaVallee et al.
2017/0105695 A1 4/2017 Ma et al.
2017/0156800 A1 6/2017 Brown
2017/0238897 A1 8/2017 Siewerdsen et al.
2018/0185113 A1 7/2018 Gregerson et al.
2018/0197315 A1 7/2018 Choi et al.
2018/0263706 A1 9/2018 Averbuch
2018/0315221 A1 11/2018 Jones et al.
2018/0315243 A1 11/2018 Mahler et al.
2019/0000372 A1 1/2019 Gullotti et al.
2019/0000564 A1 1/2019 Navab et al.
2019/0001156 A1 1/2019 Tulik et al.
2019/0183447 A1 6/2019 Mori et al.
2019/0209080 A1 7/2019 Gullotti et al.
2019/0216409 A1 7/2019 Zhou et al.
2020/0085404 A1 3/2020 Siewerdsen et al.
2020/0155238 A1 5/2020 Tillett et al.
2020/0160122 A1 5/2020 Lints et al.
2020/0222018 A1 * 7/2020 van Walsum ........ A61B 6/5264
2020/0286237 A1 9/2020 Butler
2020/0334897 A1 10/2020 Oved
2021/0049468 A1 2/2021 Karras et al.
2021/0113176 A1 4/2021 Sehnert et al.
2021/0169504 A1 6/2021 Brown
2021/0174561 A1 6/2021 Stayman et al.
2021/0192810 A1 * 6/2021 Paysan .................. G06T 11/008
2021/0407106 A1 12/2021 Fukutani et al.
2022/0020215 A1 1/2022 Banerjee et al.
2022/0031423 A1 2/2022 Halpert
2022/0160321 A1 5/2022 Le Meur et al.
2022/0215627 A1 7/2022 Haslam et al.
2022/0273375 A1 9/2022 Mucha et al.
2023/0015717 A1 * 1/2023 Wang ..................... A61B 6/466
2023/0024671 A1 1/2023 Kim et al.
2023/0076168 A1 3/2023 Sun et al.
2023/0100078 A1 3/2023 Toporek et al.
2023/0133825 A1 5/2023 Row et al.
2024/0108204 A1 4/2024 Zimmer
2024/0185509 A1 6/2024 Kovler et al.

FOREIGN PATENT DOCUMENTS

WO 2016/085973 A1 6/2016
WO 2017/029203 A1 2/2017
WO 2023/186996 A1 10/2023

OTHER PUBLICATIONS

Jecklin, S. et al., "X23D—Intraoperative 3D Lumbar Spine Shape Reconstruction Based on Sparse Multi-View X-ray Data," Journal of Imaging, Oct. 2, 2022, pp. 1-17, vol. 8, Issue 10, 271, MDPI, https://doi.org/10.3390/jimaging8100271.

An et al., "Robust Orthogonal-View 2-D/3-D Rigid Registration for Minimally Invasive Surgery", Micromachines, vol. 12, No. 7, Jul. 20, 2021, pp. 1-16.

Calvosa et al., "Imaging in Lumbar Spine Surgery: The Role of Intraoperative CT Scan", Modern Thoraco-Lumbar Implants for Spinal Fusion, 2018, pp. 15-22.

Dewey et al., "Efficient Multi-Atlas Registration using an Intermediate Template Image", Proceedings of SPIE—The International Society for Optical Engineering, Feb. 2017, pp. 1-11.

(56) References Cited

OTHER PUBLICATIONS

International Search Report and Written Opinion received for PCT Patent Application No. PCT/US2024/059213, mailed on Apr. 8, 2025, 14 pages.
International Search Report and Written Opinion received for PCT Patent Application No. PCT/US2024/059215, mailed on Mar. 24, 2025, 13 pages.
Ji et al., "Intraoperative CT as a Registration Benchmark for Intervertebral Motion Compensation in Image-guided Open Spinal Surgery", International journal of Computer Assisted Radiology and Surgery, vol. 10, No. 12, Dec. 2015, pp. 1-25.
Lecointre et al., "Preoperative SPECT/CT+ Intraoperative CT Fusion Enabling Surgical Augmented Reality to Target Sentinel Lymph Node in Endometrial Cancer", EJNMMI Physics, vol. 9, No. 1, Nov. 2022, pp. 1-8.
Masoumi et al., "Multimodal 3D Ultrasound and CT in Image-guided Spinal Surgery: Public Database and New Registration Algorithms", International Journal of Computer Assisted Radiology and Surgery, vol. 16, No. 4, Mar. 8, 2021, 555-565.
Pojskic et al., "Intraoperative Computed Tomography-Based Navigation with Augmented Reality for Lateral Approaches to the Spine", Brain Sciences, vol. 11, No. 5, May 15, 2021, pp. 1-22.
Tomaževic et al., "Reconstruction-Based 3D/2D Image Registration", International Conference on Medical Image Computing and Computer-Assisted Intervention, LNCS, vol. 3750, 2005, pp. 231-238.
Ying et al., "X2CT-GAN: Reconstructing CT From Biplanar X-Rays With Generative Adversarial Networks", Proceedings of the IEEE/CVF Conference on Computer Vision and Pattern Recognition, Jun. 15-20, 2019, pp. 10619-10628.

* cited by examiner

SYSTEM AND METHOD FOR RECONSTRUCTION OF 3D VOLUMES FROM BIPLANAR RADIOGRAPHIC IMAGES

CROSS REFERENCE TO RELATED APPLICATIONS

This application is a continuation of U.S. application Ser. No. 18/974,545 filed on Dec. 9, 2024, entitled SYSTEM AND METHOD FOR RECONSTRUCTION OF 3D VOLUMES FROM BIPLANAR RADIOGRAPHIC IMAGES which claims the benefit of priority to the following applications, filed by the same Applicant, See All AI Inc., the entire contents of all of which are incorporated herein by this reference for all purposes:

U.S. Provisional Application No. 63/607,956, filed on Dec. 8, 2023, and,

U.S. Provisional Application No. 63/608,122, filed on Dec. 8, 2023.

Further, the entire contents of the following applications, filed by the same Applicant on Dec. 9, 2024, are incorporated herein by this reference for all purposes:

U.S. patent application Ser. No. 18/974,399, entitled "System And Method For Generation Of Registration Transform For Surgical Navigation"; and U.S. patent application Ser. No. 18/974,359, entitled "Wire-Based Calibration Apparatus for X-ray Imaging Systems".

FIELD OF THE INVENTION

Disclosed is a system and technique related to three-dimensional (3D) imaging in medical diagnostics for providing surgical navigation, and, more particularly to tracking of surgical instruments within a reconstructed 3D volume, and aligning the instrument coordinates with the patient and volume coordinate systems.

BACKGROUND OF THE INVENTION

Traditional static radiographic images, including X-rays and computer tomography, have been used in medical imaging and diagnostics, however, these technologies are not well suited for procedures requiring real time imaging of patient anatomy and/or surgical navigation assistance. Instead, fluoroscopy, comprising pulsed radiographic energy, is utilized for multiple procedures in which real time visual assistance is required during the procedure. However, fluoroscopic images provide only two-dimensional views of the patient anatomy and are not suitable for complicated procedures, especially surgical procedures which require three-dimensional image of the patient anatomy and real time displays of instruments relative to the patient's anatomy. Unfortunately, real time generation of a patient's anatomy via computerized tomography is very expensive. More recently, attempts have been made to generate or reconstruct three-dimensional volume of CT quality images from a limited number of X-rays, as disclosed in U.S. Pat. No. 10,709,394, however, the disclosed system and method is not useful for real time surgical navigation assistance and the resulting volume from lack of accuracy due to the averaging of values to create the reconstructed CT images.

Computer assisted surgical systems utilize predominantly visual position data to assist surgeons, without the benefit of radiographic images, such as that disclosed in US Patent Application Publication US20050159759A1, however, such systems are typically limited to used identifying proper incision location and surgical navigation guidance relative to only exposed patient anatomy. Accordingly, a further need exists for a way to provide real-time three-dimensional CT quality images of unexposed patient anatomy to assist with surgical navigation.

Attempts have been made to utilize both radiographic images and visually acquired positional data to assist with surgical navigation, such as that disclosed in US Patent Application Publication US20210169504A1, however, such system is not capable of creating a three-dimensional volume of CT quality images useful for real time surgical navigation purposes. The difficulty in attempting to utilize visually acquired position information and radiographic images is the calibration of the camera's coordinate system with that of the X-ray imaging system. This problem is further compounded when trying to align the position of a surgical instrument as defined within the coordinate system of the patient or camera within the coordinate system of a three dimensional volume of radiographic images, such as CT images.

Accordingly, a need exists for a system and method which is capable of accurately creating a 3D volume of the patient anatomy in an efficient, near real-time manner from relatively few radiographic images and which is further capable of aligning the detected position of a surgical instrument in the patient coordinate space with the created three dimensional volume of CT quality images of the patients anatomy, to facilitate accurate navigational guidance of instruments relative to both exposed and non-exposed patient anatomy.

As noted, medical imaging technologies, including fluoroscopic imaging are widely used in medical diagnostics and interventional procedures to obtain real-time images of the internal structures of a patient. Traditional fluoroscopic systems, however, do not automatically record detailed data on the position and orientation of each image with respect to the patient and the imaging device. This limitation can hinder the accurate reconstruction of three-dimensional volumes from the fluoroscopic images, needed for advanced diagnostic and therapeutic applications. This problem is relevant to surgical procedure involving the spine. The human spine comprises multiple bony vertebral bodies that can move relative to one another. Tracking each vertebral body during a spinal surgical procedure would be cumbersome, computationally intensive and time-consuming.

Intraoperative imaging plays a pivotal role in modern surgical navigation, enabling surgeons to make informed decisions based on real-time anatomical information. Traditional computed tomography (CT) scanners, while providing detailed 3D images, are often impractical in an operating room due to their size, cost, and the time required for scanning. Accordingly, a need exists for portable imaging solutions that can provide high-quality 3D reconstructions with minimal equipment and radiation exposure.

The challenge lies in reconstructing a 3D volume from limited two-dimensional (2D) projection data. The limited-angle problem in tomography states that accurate reconstruction is fundamentally challenging when projection data is insufficient or confined to a restricted angular range. This limitation poses significant hurdles in scenarios where acquiring multiple projections is impractical.

The reconstruction of three-dimensional (3D) volumes from two-dimensional (2D) projections is a fundamental problem in tomographic imaging. The foundational mathematical work by Alan Cormack in the 1960s laid the groundwork for computed tomography (CT) by developing the theoretical framework for reconstructing an object from its projections. His pioneering contributions, for which he was awarded the Nobel Prize in Physiology or Medicine in 1979, utilized the Radon transform to relate projection data to the internal structure of an object.

Classical reconstruction algorithms, such as filtered back projection, rely on the availability of projection data over a wide range of angles to produce accurate reconstructions. However, in practical scenarios, especially in medical imaging during surgery, acquiring projections over a full angular range can be impractical due to time constraints, patient movement, or the need to minimize radiation exposure.

The limited angle problem is a well-known issue in computed tomography, stating that accurate reconstruction is fundamentally impossible when projection data is missing or limited to a restricted angular range. Eric Todd Quinto, a mathematician at Tufts University, has extensively studied the limited angle problem and its implications for CT. His work has shown that certain features of an object, especially those aligned with the missing projection angles, cannot be accurately reconstructed, leading to artifacts and incomplete images. Traditional methods struggle to compensate for the missing information, resulting in degraded image quality.

Accordingly, a need exists for a system and technique for accurate reconstruction of a 3D volume from limited 2D projection data.

Accordingly, a need exists for a way to provide three-dimensional CT quality images in real-time to assist with surgical navigation.

SUMMARY OF THE INVENTION

Disclosed is a system and methods for combining optical and radiographic data to enhance imaging capabilities. Specifically, the disclosed system and method combine both visually obtained patient pose position information and radiographic image information to facilitate calibrated surgical navigation. The process involves a data acquisition phase, a system calibration phase, a volume reconstruction phase, and a surgical navigation phase, all resulting in the alignment of instrument coordinates with the patient and reconstructed volume coordinates enabling tracking and navigation of surgical instruments within a reconstructed 3D volume of a patient anatomy, even if the such anatomy is not exposed during a procedure.

Disclosed is a system and technique of 3D imaging and medical diagnostics for providing surgical navigation, and, more particularly to tracking of surgical instruments within a reconstructed 3D volume, and aligning the systems. The disclosed system and method combine precise pose estimation via camera calibration with deep learning techniques to reconstruct 3D volumes from only two biplanar X-ray images. The system further computes a registration transform that allows tracking of surgical instruments within the reconstructed volume, and aligning the instrument coordinates with the patient and volume coordinate systems. Importantly, the same registration transform is used to define the center and orientation of the voxel grid for back projection, ensuring consistency between the navigation and imaging components of the system.

One aspect of the disclosure is the automatic registration of surgical instruments surgical navigation. By enabling automatic registration, the system facilitates minimally invasive procedures where the patient's anatomy does not need to be exposed for registration purposes. Furthermore, the surgical instrument does not need a reference array. Tracking may be done by object recognition of the surgical instrument by the optical cameras and employing 3D localization algorithms to determine the instruments' poses relative to the patient reference marker.

An additional significant contribution is the correction of non-linear distortions in the X-ray images. The markers in the calibration target attached to the C-arm are utilized not only for pose estimation but also to determine non-linear distortions typically caused by X-ray image intensifier systems, such as pincushion and S-distortions. Accounting for these distortions is essential when back projecting the voxel grid onto the 2D X-ray images.

The grid used in the reconstruction is centered at the computed point of intersection of the X-ray projection vectors and aligned along basis vectors derived from these vectors, ensuring that the volume is in the patient's coordinate frame. Each voxel coordinate is projected onto the biplanar images using the calibration matrices, establishing a direct connection between the generalized Radon transform and the reconstructed volume. An additional motivation for centering the grid at the point of intersection and aligning it with the basis vectors is to ensure that when projected onto the two X-ray images, the grid points will generally fall within the field of view of the X-ray images. If the grid is not centered appropriately and oriented with the basis vectors, the projected grid points may fall outside the biplanar X-ray fields of view, rendering the volume less useful when passing the concatenated back projected volumes through the trained U-Net.

Disclosed is a registration transform process that allows for the precise alignment of a reconstructed 3D volume with the patient's actual anatomy, ensuring that surgical tools and procedures can be accurately guided based on the reconstructed images. The ability to generate this registration transform directly from the radiographic images used for 3D volume reconstruction streamlines the process, making it more efficient and reducing the need for additional imaging or calibration steps typically required in surgical navigation.

The disclosed system can be integrated into existing surgical navigation systems, enhancing accuracy and reliability. By providing a direct method to obtain a transformation matrix, e.g. 4×4, that encompasses both positional and rotational information, the system significantly aids in the precise orientation of surgical instruments and navigation within the surgical field.

In accordance with another aspect of the disclosure, a system and technique is disclosed for generation of a registration transform for surgical navigation by leveraging the central rays of the X-ray images. The central ray, defined as the ray that extends from the X-ray source to the detector, plays a pivotal role in this process. The disclosed technique is a shelf grounded in the geometric properties of the central rays and their interactions within the 3D volume. The method addresses key challenges in traditional calibration approaches, offering improved accuracy, robustness, and integration with 3D reconstruction workflows.

Disclosed is an imaging system that reconstructs three-dimensional (3D) computed tomography (CT) volumes from two biplanar X-ray images captured using a mobile X-ray C-arm equipped with optical tracking. The system utilizes an external optical camera to detect reference markers attached to both the patient and a calibration target mounted on the X-ray C-arm. The calibration target contains radiopaque markers with known spatial coordinates, visible in the X-ray images. During each X-ray capture, the optical camera records the six degrees of freedom (6-DoF) poses (rotation and translation) of the reference markers. The X-ray images are processed to detect the calibration markers, which are then used in a camera calibration algorithm to compute the intrinsic and extrinsic parameters of the X-ray system. These parameters provide the precise poses of the two independent X-ray projections, serving as inputs to a deep learning algorithm that reconstructs 3D CT volumes from the biplanar X-rays using the generalized Radon transform and a trained 3D U-Net.

Further disclosed is a method for tracking surgical instruments within the reconstructed volume by computing a registration transform that aligns the instrument coordinates with the patient and volume coordinate systems. The registration transform is also used to define the center and orientation of the voxel grid for back projection and reconstruction, ensuring consistency between the navigation and imaging components of the system. Automatic registration of the surgical instruments is a needed aspect of surgical navigation, especially in minimally invasive procedures where the patient's anatomy does not need to be exposed for registration. This capability enhances the practicality and safety of such procedures. Additionally, the surgical instruments may or may not require a reference array; one tracking approach utilizes object recognition by the optical cameras and 3D localization algorithms to determine the instruments' poses relative to the patient reference marker.

One aspect of the disclosed technique is the correction of non-linear distortions in the X-ray images. The radiopaque markers in the calibration target attached to the C-arm are also used to determine non-linear distortions typically caused by X-ray image intensifier systems, such as pincushion and S-distortions. Accounting for these distortions is essential when back projecting the voxel grid onto the 2D X-ray images. This step may not be necessary for flat panel X-ray detectors, which generally do not exhibit these types of distortions.

The reconstruction process is centered at the point of intersection of the X-ray projection vectors, and the volume is aligned along basis vectors derived from these vectors, ensuring that the voxel grid is defined in the patient's coordinate system. Each voxel coordinate is projected onto the biplanar images using the calibration matrices, connecting the generalized Radon transform to the reconstructed volume. This integration allows for precise instrument navigation within the patient's anatomy using the generated registration transform. An additional motivation for centering the grid at the point of intersection and aligning it with the basis vectors is to ensure that when projected onto the two X-ray images, the grid points will generally fall within the field of view of the X-ray images. If the grid is not centered appropriately and oriented with the basis vectors, the projected grid points may fall outside the biplanar X-ray fields of view, rendering the volume less useful when passing the concatenated back projected volumes through the trained U-Net. Disclosed is an in-depth mathematical description of the system components, marker detection, camera calibration, CT reconstruction, and instrument tracking processes, highlighting the motivations and challenges addressed in each section.

The calibration of X-ray images is a two-fold process involving both intrinsic and extrinsic parameters. Intrinsic calibration focuses on the internal characteristics of the X-ray imager, such as the lens distortions, focal length, and principal point.

Extrinsic calibration, on the other hand, deals with the spatial positioning and orientation of the X-ray imaging device. Extrinsic calibration involves determining the relative 3D poses of the X-ray images. This is accomplished either through encoders integrated within the X-ray imaging system or via an external navigation system. The external system records the precise pose positions of the imaging device during the image capture process. These pose positions are then used to accurately back-project the encoded images into the common coordinate system.

The combination of intrinsic and extrinsic calibrations ensures that each X-ray image is precisely aligned in terms of both its internal geometry and its spatial orientation. This dual calibration approach is essential for accurate back-projection and reconstruction of the 3D volume. It addresses and overcomes the traditional challenges faced in 3D imaging, particularly in scenarios where only a limited number of images and a restricted range of angles are available. The resulting 3D volume is not only complete but also exhibits high resolution and accuracy, marking a significant improvement over conventional methods.

The system uses a model capable of accurately reconstructing 3D volumes from a limited set of X-ray images. This model is achieved through a detailed and comprehensive training regime, enabling the accurate reconstruction of 3D volumes from X-ray images. The model training involves a sophisticated interplay between encoding X-rays, back-projecting them into a 3D volume, decoding this volume, and refining the system through iterative learning.

According to still another aspect of the disclosure, a method for generating a registration transform for surgical navigation systems, comprises: a) capturing a set of at least two radiographic images and generating, for each of the respective images, a central ray representing a path from a radiation source to a radiographic image detector; b) identifying an intersection point of the central rays; c) generating a registration transform based on the intersection point and orientation of the central rays and generating a 3D volume reconstruction from the at least two radiographic images, and d) integrating the registration transform with a surgical navigation system to align surgical tools with the reconstructed 3D volume. In embodiments c) comprises generating the registration transform as part of a process of generating a 3D volume reconstruction from the radiographic images. In embodiments, the registration transform includes positional information (x, y, z) and rotational information (yaw, pitch, roll) relative to a reference marker on one of a subject or the radiographic image detector.

According to yet another aspect of the disclosure, a system for surgical navigation, comprises: a) an image processing module for reconstructing a 3D volume from at least X-ray images and for identifying an intersection point of computed central rays of each of the X-ray images; b) a transform generation module for creating a registration transform based on the intersection point and orientation of the central rays each of the X-ray images, wherein the registration transform defines the positional and rotational relationship of a 3D volume relative to a physical reference marker on a subject; and c) a navigation interface utilizing the registration transform to visually align surgical instruments with the 3D volume. In embodiments, the system further comprises a physical reference marker on a subject.

According to still yet another aspect of the disclosure, a non-transitory computer-readable medium storing instructions that, when executed by a processor, cause a system to perform the method comprising: a) capturing a set of at least two radiographic images and generating, for each of the respective images, a central ray representing a path from a radiation source to a radiographic image detector; b) identifying an intersection point of the central rays; c) generating a registration transform based on the intersection point and orientation of the central rays and generating a 3D volume reconstruction from the at least two radiographic images, and d) integrating the registration transform with a surgical navigation system to align surgical tools with the reconstructed 3D volume. In embodiments c) comprises generating the registration transform as part of a process of generating a 3D volume reconstruction from the radiographic images. In embodiments, the registration transform includes positional information (x, y, z) and rotational information (yaw, pitch, roll) relative to a reference marker on one of a subject or the radiographic image detector.

According to a further aspect of the disclosure, a method for tracking surgical instruments comprises: A) detecting a position of an instrument in a subject coordinate system; B) constructing a registration transform defining a center and orientation of a voxel grid usable for back projection and reconstruction of a 3D volume; C) reconstructing a 3D volume from two biplanar images of the subject using the registration transform; and D) aligning the position of the instrument in the subject coordinate system with the reconstructed 3D volume. In embodiment, the method further comprises: E) overlaying the aligned instrument position onto the reconstructed 3D volume. In embodiment, the registration transform includes positional (x, y, z) and rotational (yaw, pitch, roll) data relative to reference marker in the subject coordinate system.

According to still a further aspect of the disclosure, a method for marker-less surgical instrument tracking comprises: A) detecting a position of an instrument in a subject coordinate system using object recognition; and B) aligning coordinates of the instrument position with the subject coordinate system and coordinates of a volume, wherein aligning coordinates of the instrument position with the subject coordinate system and coordinates of a volume is done without a reference array associated with the instrument.

According to still a further aspect of the disclosure, a method of synchronizing coordinate systems in a surgical navigation system comprises: A) detecting a pose of a subject in a subject coordinate system; B) generating reconstructed 3D volume from two biplanar X-ray images of the subject pose; C) detecting a position of a instrument in the subject coordinate system; D) aligning the position of the instrument with the reconstructed volume through use of a shared registration transform; and E) overlaying the translated instrument position onto the reconstructed 3D volume.

According to yet a further aspect of the disclosure, a method of synchronizing coordinate systems in a surgical navigation system comprising: A) detecting pose information of a subject in a subject coordinate system; B) generating reconstructed 3D volume from at least two biplanar radiographic images of the subject pose; C) detecting pose information of a surgical instrument in the subject coordinate system; and D) aligning a position of the surgical instrument within the reconstructed volume through use of a generated shared registration transform. In embodiments, the method further comprises: E) overlaying the aligned instrument position onto the reconstructed 3D volume. In embodiments, the shared registration transform comprises both positional and rotational information and is at least partially derived from both the pose information. In embodiments, the shared registration transform is at least partially derived from both the pose information and the at least two biplanar radiographic images.

According to still a further aspect of the disclosure, a method of synchronizing coordinate systems in a surgical navigation system comprises: A) acquiring a pair of biplanar images; B) generating a projection vector from each of the biplanar images; C) deriving a registration transform function from parameters of the projection vectors; D) defining point of intersection of the projection vectors in a first three-dimensional space as a center of a voxel grid; E) back-projecting the voxel grid to create a three-dimensional volume of the biplanar images; F) detecting a position of an instrument within a patient coordinate system; G) aligning the instrument position with the three-dimensional volume; and H) projecting an image of the aligned instrument position overlayed over the three-dimensional volume.

According to another aspect of the disclosure, disclosed is a system and method for reconstructing three-dimensional (3D) computed tomography (CT) volumes from biplanar X-ray projections using deep learning techniques. Traditional tomographic methods are fundamentally limited by the limited angle problem, which asserts that accurate reconstruction is impossible when projection data is insufficient or limited in angular range. The disclosed technique addresses this challenge by employing a deep learning model that leverages the statistical properties of the data to learn the mapping from limited angle projections to full 3D volumes. Starting with the mathematical notation for X-ray projections at arbitrary poses using a generalized Radon transform, these X-rays projections are back projected into two separate volumes and the volumes then concatenated. The concatenated volume is passed through a 3D U-Net to decode the concatenated volume into a single 3D volume. With sufficient training data comprising biplanar X-rays and their associated real CT scans, the trained model can approximate the true CT scan for any new set of biplanar X-rays not seen during training. This method effectively overcomes the limitations imposed by the limited angle theorem through the power of deep learning.

According to yet a further aspect of the disclosure, a method for reconstructing a three-dimensional volume from biplanar x-ray projections comprises: A) obtaining first and second biplanar X-ray projections; B) back projecting the first and second X-ray projections into corresponding first and second three-dimensional volumes, respectively; C) concatenating the first and second volumes into a combined volume along a new dimension; and D) mapping the combined volume to a three-dimensional volume using a pretrained neural network.

According to yet a further aspect of the disclosure, a method for reconstructing a three-dimensional volume from biplanar x-ray projections, the method comprising: A) back-projecting each of two separate X-ray projections into a respective separate first and second 3D volumes; B) concatenating the first and second 3D volumes along a new channel dimension to form a multichannel input; and C) providing the concatenated volume as input into a pretrained 3D deep learning model, which outputs a reconstructed 3D volume.

According to yet a further aspect of the disclosure, a method for training a deep learning network model to create a three-dimensional volume from at least two projections derived from two dimensional biplanar images, and a true CT volume, the method comprising: A) initializing network parameters of the model before a starting training process; B) iterating through the network model with the training process over a number of epochs; C) for each training sample: C1) back-projecting each projections into a separate respective volume, concatenating the separate volumes into a combined volume along a new dimension, and computing a network model output, C2) calculating a loss between the network model output and the true CT volume, C3) computing gradients of the calculated loss with respect to the network parameters, and C4) updating the network parameters using an optimization algorithm; and D) defining the optimized network parameters following iteration through the each training sample and epoch as a trained network model.

According to yet a further aspect of the disclosure, a method for constructing a three-dimensional (3D) volume from a set of two or more medical images, the method comprising: A) acquiring two or more biplanar radiographic images; B) calibrating each of the biplanar radiographic images both intrinsically and extrinsically in relation to a common coordinate system; C) encoding the calibrated images using a machine learning or deep learning algorithm; D) back-projecting the encoded images into the common coordinate system based on known relative 3D poses; and E) decoding the back-projected images to reconstruct the 3D volume. In some implementations, machine learning or deep learning algorithm is trained on a dataset comprising CT scans and corresponding X-ray images. In some implementations, the method further comprises: F) iteratively refining the encoding and decoding algorithms using a training process by comparing reconstructed 3D volume with pre-existing corresponding computed tomography (CT) scans. In some implementations, the medical images comprise x-ray images. In some implementations, the intrinsic calibration includes determining lens distortions, focal length, and principal point of the X-ray imager. In some implementations, the extrinsic calibration includes determining the spatial positioning and orientation of the X-ray imaging device using either integrated encoders or an external navigation system.

According to still a further aspect of the disclosure, a method for constructing a three-dimensional (3D) volume from a set of two or more medical images, the method comprising: A) acquiring two or more biplanar radiographic images; B) calibrating each of the biplanar radiographic images both intrinsically and extrinsically in relation to a common coordinate system; C) encoding the calibrated images using a machine learning or deep learning algorithm; D) back-projecting the encoded images into the common coordinate system based on known relative 3D poses; and E) decoding the back-projected images to reconstruct the 3D volume. In some implementations, machine learning or deep learning algorithm is trained on a dataset comprising CT scans and corresponding X-ray images.

According to still a further aspect of the disclosure, a system for reconstructing a 3D volume from a set of two or more medical images comprises: A) a calibration target attachable to a radiographic image acquisition system for collecting radiographic images; B) a calibration module for performing intrinsic and extrinsic calibrations of acquired radiographic images; C) an encoding module utilizing a machine learning or deep learning algorithm for encoding the acquired images; D) a back-projection module for aligning the encoded images within a common coordinate system; and E) a decoding module for reconstructing the 3D volume from the back-projected images. In some implementations, the medical images comprise x-ray images. In some implementations, the system further comprises a training module for iteratively refining the encoding and decoding algorithms based on comparisons with corresponding CT scans.

According to yet a further aspect of the disclosure, a computer program product comprising a non-transitory computer-readable medium storing instruction that, when executed by a processor, cause the processor to perform a method for constructing a three-dimensional (3D) volume from a set of two or more medical images, the method comprising: A) acquiring two or more biplanar radiographic images; B) calibrating each of the biplanar radiographic images both intrinsically and extrinsically in relation to a common coordinate system; C) encoding the calibrated images using a machine learning or deep learning algorithm; D) back-projecting the encoded images into the common coordinate system based on known relative 3D poses; and E) decoding the back-projected images to reconstruct the 3D volume. In some implementations, machine learning or deep learning algorithm is trained on a dataset comprising CT scans and corresponding X-ray images. In some implementations, the method further comprises: F) iteratively refining the encoding and decoding algorithms using a training process by comparing reconstructed 3D volume with pre-existing corresponding computed tomography (CT) scans. In some implementations, the medical images comprise x-ray images. In some implementations, the intrinsic calibration includes determining lens distortions, focal length, and principal point of the X-ray imager. In some implementations, the extrinsic calibration includes determining the spatial positioning and orientation of the X-ray imaging device using either integrated encoders or an external navigation system.

BRIEF DESCRIPTION OF THE DRAWINGS

The accompanying drawings, which are incorporated in and constitute a part of the specification, illustrate various example methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. Furthermore, elements may not be drawn to scale.

DETAILED DESCRIPTION

Disclosed is a system and methods for combining optical and radiographic data to enhance imaging capabilities. Specifically, the disclosed system and method combine both visually obtained patient pose position information and radiographic image information to facilitate calibrated surgical navigation. The process involves a data acquisition phase, a system calibration phase, a volume reconstruction phase, and a surgical navigation phase, all resulting in the alignment of instrument coordinates with the patient and reconstructed volume coordinates enabling tracking and navigation of surgical instruments within a reconstructed 3D volume of a patient anatomy, even if the such anatomy is not exposed during a procedure.

Figure 1:
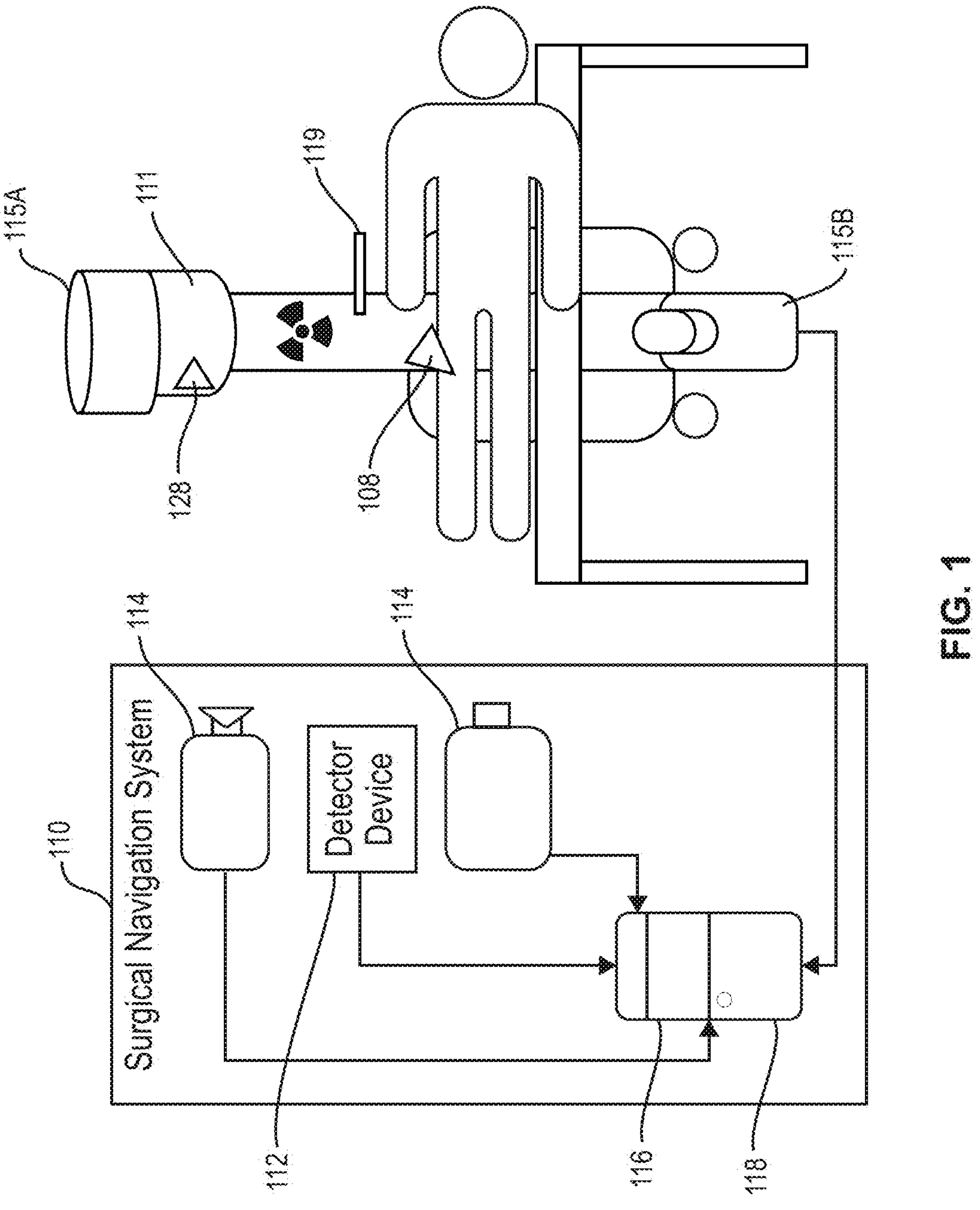
FIG. 1 is a conceptual illustration of a surgical navigation system in accordance with the disclosure.

FIG. 1 illustrates conceptually a surgical navigation system 110 suitable for use with the reference markers and anchors described herein. The surgical navigation system 110 may be used with a traditional fluoroscopy machine, e.g. a C-arm, having a source of radiation 115B disposed beneath the patient and a radiographic image detector 115A disposed on the opposite side of the patient.

In embodiments, surgical navigation system 110 comprises reference markers 108 or 128, a radiation detector 112, a calibration target 111, cameras 114, computer 116, and a display interface 118 used with an radiation source 115B and radiographic image detector 115A, device 115A. In embodiments, the components of surgical navigation system 110 may be contained within a single housing which is easily positionable along three axes within the surgical procedure space. Alternatively, one or more the components of surgical navigation system 110 may be located remotely from other components but interoperable therewith through suitable network infrastructure. The surgical system 110, and particularly cameras 114, track the reference marker 108 or 128 within the camera coordinate system, e.g. the patient coordinate system, and forward the positional information of the reference markers onto computer 116 for further processing.

One or more external optical camera 114 may be positioned to capture the operating area, as illustrated, and detect optical reference marker 8 attached to the patient and the reference marker 128 attached to the calibration target 111. External optical camera 14 provides real-time tracking of the 6-DoF poses (rotation and translation) of the markers108 and 128. In embodiments, camera 114 may be implemented using one or more visible light cameras to capture real-time images of the surgical field including the patient and X-ray imaging system, e.g. a fluoroscope. A camera suitable for use as camera 114 is the Polaris product line of optical navigation products, commercially available from Northern Digital, Waterloo, Ontario, Canada. External camera 114 may be in communication with one or both of synchronizing device 112 and a processing unit 116. When the imaging systems X-ray is triggered, synchronizing device 112 identifies X-ray emissions relative to a predefined threshold level and signals computer 116 and/or external camera 114 and to capture pose information of the patient and imaging system itself via reference markers 108 and 128, respectively.

Reference markers 108 and 128 are fiducial markers that are easily detectable by the optical camera 114 and are attached to the patient and the calibration target 111, respectively, and serve as points of reference for coordinate transformations. The implementation of reference markers 108 and 128 is set forth in greater detail in co-pending U.S. patent application Ser. No. 18/974,434, entitled "Omni-View Unique Tracking Marker".

Figure 8:
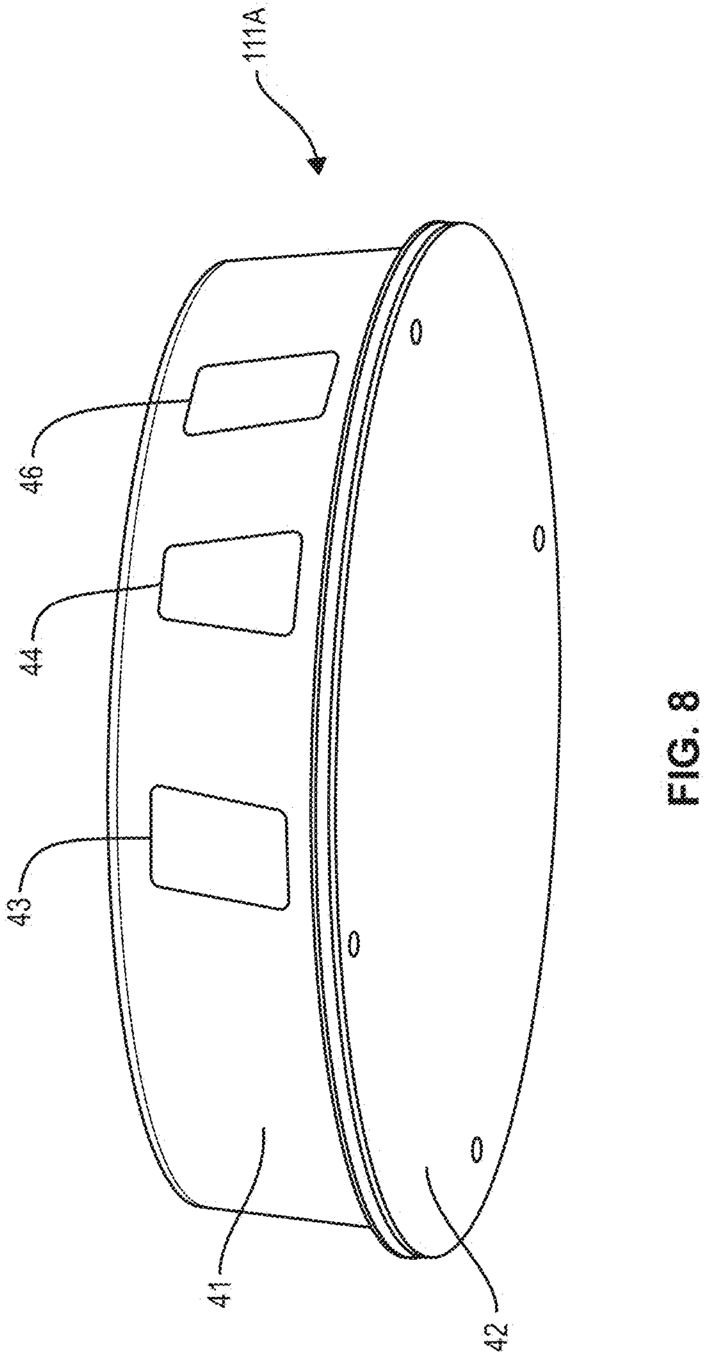
FIG. 8 is a conceptual perspective illustration of a calibration target apparatus in accordance with the disclosure.

Calibration target 111A, attachable to the radiographic image detector 115A, may be implemented with radiopaque wire markers embedded within the calibration target, as further described herein and in co-pending U.S. patent application Ser. No. 18/974,359, entitled "Wire-Based Calibration Apparatus for X-ray Imaging Systems". In embodiments, the calibration target may have the exterior body configuration of target 111A of FIG. 8A. Calibration target 111A comprises a target body 41 having a substantially circular shape which is attachable directly to the radiation detector housing of an imaging system. A cover 42 is attached to target body 41 and made of a material that is essentially transparent to radiation incident thereon so as not to block such radiation from reaching the radiation detector. In embodiments, multiple reference elements 43, 44 and 46 are attached to or embedded into a sidewall or surface of target body 41. Each of elements 43, 44 and 46 may have a similar or different shape relative to the other of the elements, but each element 43, 44 and 46 has a unique position relative to the target body 41. In this manner, when viewed by a color or visible light camera, the unique geometry and surface texture of markers 43, 44, and 46 enables the target 111A to be easily distinguished from its surroundings, regardless of a camera angle(s), to enable precise tracking of the position and orientation of target 111A and the radiation detector 115B in a three-dimensional space.

Figure 9:
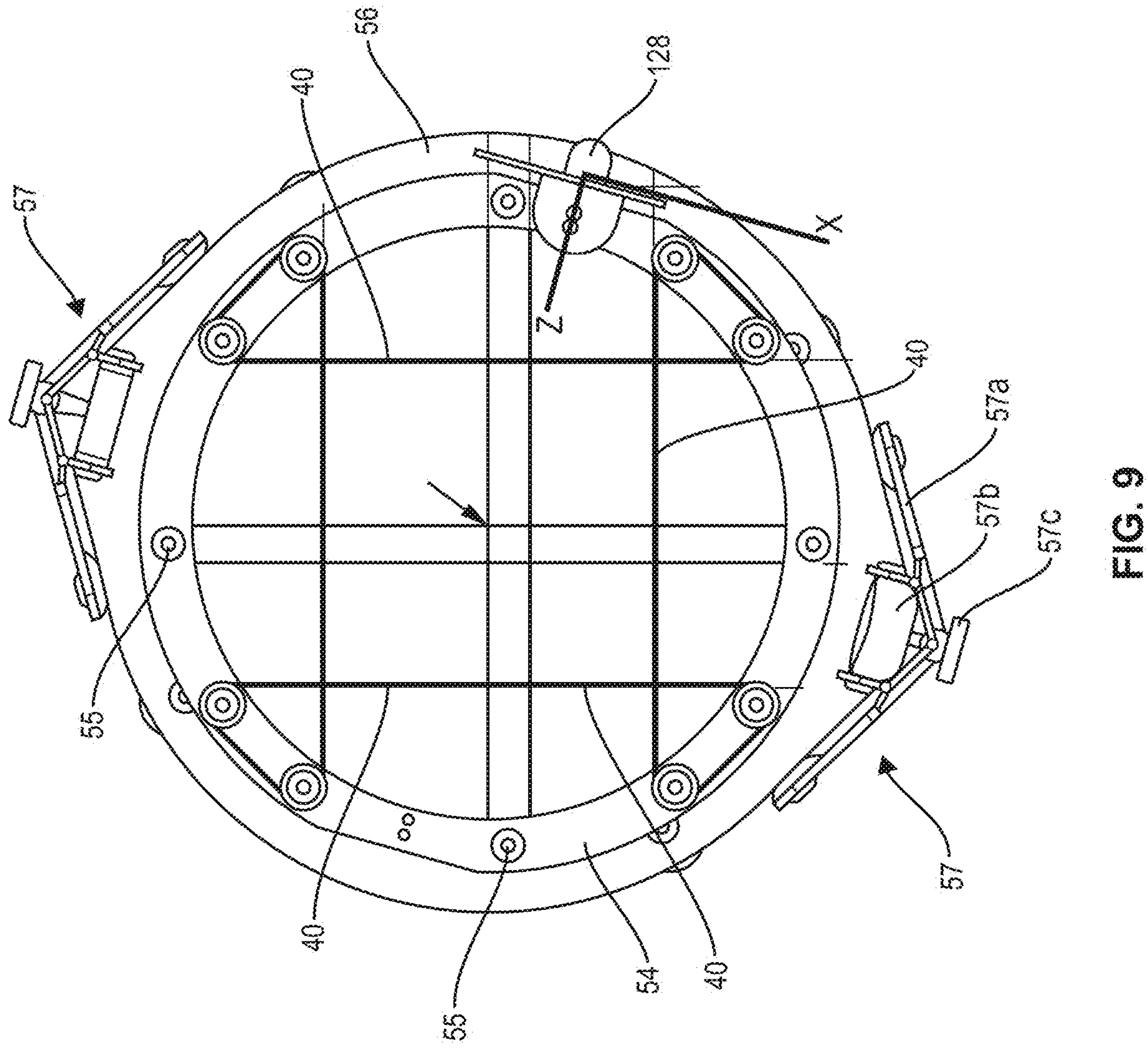
FIG. 9 is a top view illustration of a calibration target apparatus in accordance with an the disclosure.

FIG. 9 is a top view illustration of a calibration target comprising a target body 52, a mounting mechanism 57, and a plurality of linear calibration markers 40 arranged in a known geometric pattern. Target body 52 comprises a pair of ring-shaped frames 54 and 56 coupled together but spaced apart by posts 55. A plurality of pads or suction cups (not shown) are disposed on the side of ring 56 which will be positioned adjacent a radiation detector to help secure the calibration target 111A thereagainst.

The mounting mechanism 57 comprises a pair of brackets are attached to opposing sides of frames 56, each with an clamping block 18 and tightening screw 59 to allow manual tightening of brackets 17*a-b* to the radiation detector. In this manner, mounting mechanism 57 facilitate removably securing calibration target 111A to the radiation detector of an imaging system.

In embodiments, target body 52 may be made from a substantially rigid or semirigid material and may have a circular exterior shape, as illustrated, for attachment to the radiation detector of a C-arm X-ray machine, or, may have other shapes adapted to be secured within the path of radiation incident on the radiation detector of an imaging system.

In embodiments, calibration markers 40 may be implemented with wires that may be made of all or partially radiopaque material (e.g., tungsten or steel) to ensure visibility in X-ray images. The wires 40 may be arranged at different known depths relative to the plane or face of the radiation detector to provide 3D spatial information. In embodiments, the wires may be positioned such that they are generally parallel to the face of the radiation detector, simplifying the projection geometry. In embodiments, the diameter of the wires is optimized to be large enough to be visible in the detected radiation images but small enough to occupy minimal pixel area to facilitate digital subtraction.

In embodiments, wires 40 may be implemented with Tungsten wires with diameter 0.5 mm, although other diameters may be used. In embodiments, wires 40 may be implemented with round wound or flat wound wires. Wires 40 may be placed at depths between z=0 mm and z=−50 mm relative to the calibration target origin. Wires 40 may be arranged in a grid pattern with known spacing, intersecting at known crossover points, as illustrated, although other intersecting wire patterns may be used.

The wires 40, as illustrated in FIG. 9 have known 3D spatial coordinates relative to reference marker 128 or reference elements 43, 44, and 46 attached to the calibration target 111A. Such wires are visible in the captured radiographic images 5 and 15 and used for calibrating the radiographic imaging system, including intrinsic correction of non-linear distortions. With of calibration target 111A and 111B, illustrated herein, there is no need for second reference marker 128, as previously described, to determine the position of the imaging system to which the calibration target is attached, since the reference elements 43, 44, and 46 collectively are detectable from the exterior of calibration target 111A.

Surgical Instrument(s) 119 may be equipped with optical markers or tracked using object recognition and 3D localization algorithms, as described further herein, and allow for real-time tracking and alignment within a 3D volume of CT quality images reconstruct from two radiographic image, e.g. X-rays.

Display interface 118 is operably coupled to computer 116 and provides real-time visual feedback to the surgical team, showing the precise positioning and movement of the patient, imaging system itself, and any instruments. A display interface 118 suitable for use is the 13" iPad Air, commercially available from Apple Computer, Inc. Cupertino, CA, USA, however, other commercially available surgical monitor may be used. As noted previously, the display interface may be located remotely from the computer 116 to facilitate more convenient positioning of the display interface 118 for the surgeon during the procedure.

Method of Operation

Figure 2A:
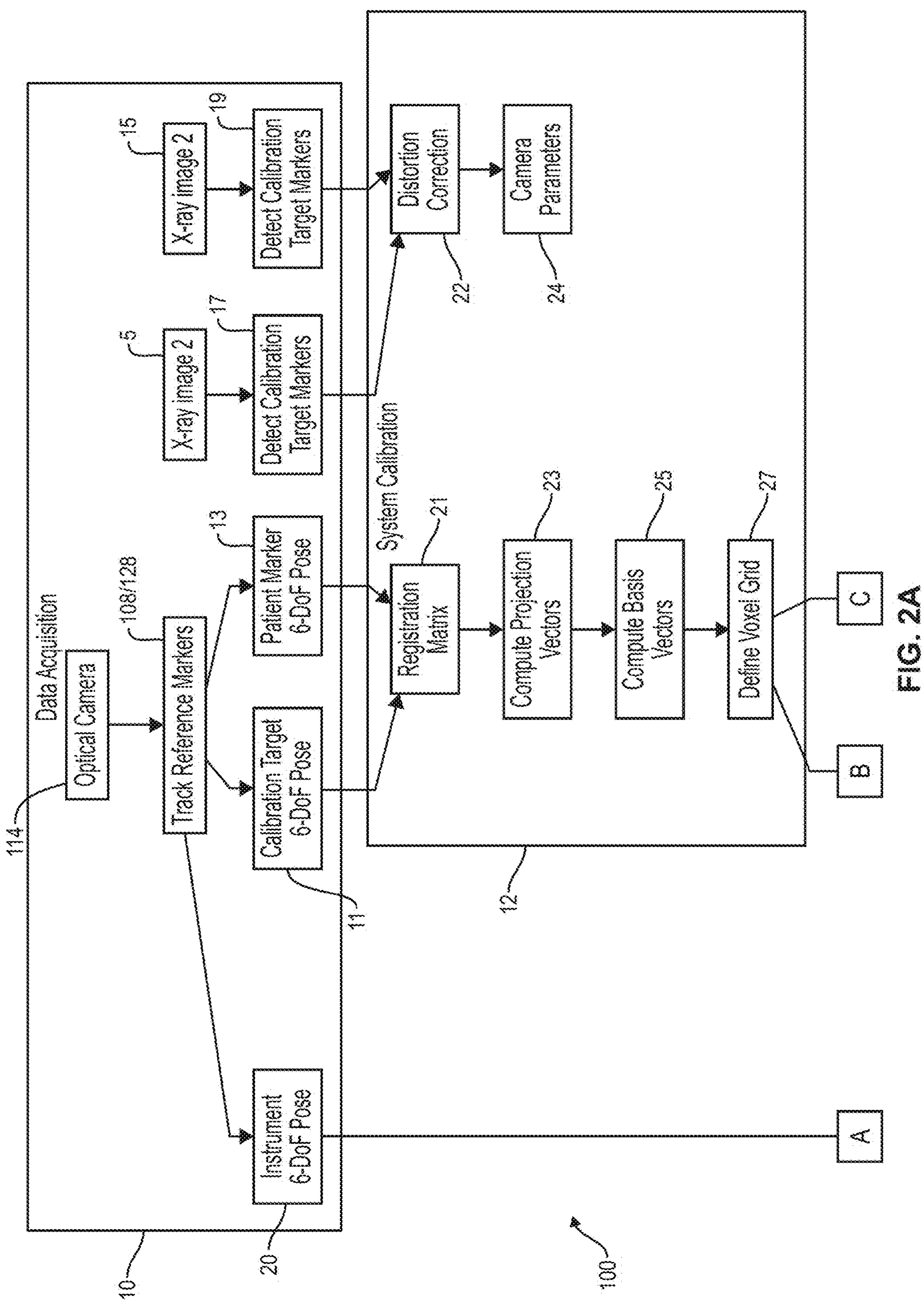
FIGS. 2A-B conceptually illustrate a more detailed process flow of the overall methods performed by the surgical navigation system in accordance with the disclosure.
Figure 2B:
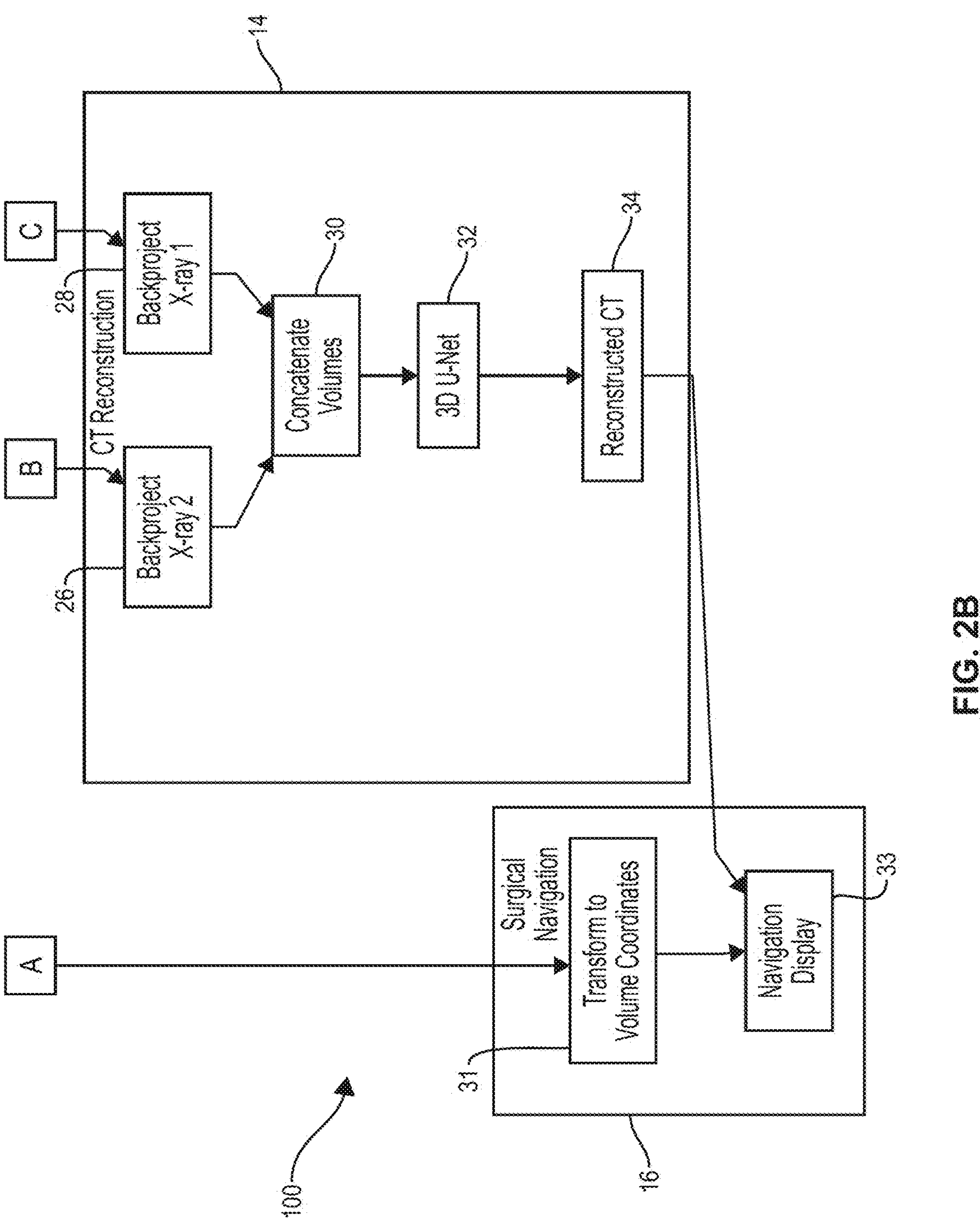

FIGS. 2A-B collectively illustrates a conceptual process flow 100 of the overall methods performed by the surgical navigation system 110 in accordance with the disclosure. Process flow 100 comprises a data acquisition phase 10, a system calibration phase 12, a CT volume reconstruction phase 14, and a surgical navigation phase 16. In initial setup, the camera 114 along with integrated radiation detection device 112 are positioned in the operating room within the surgical field. Reference marker 108 is disposed on or near the patient anatomy. Reference marker 128 is disposed on calibration target 111 which is attached to radiographic image detector 115A.

In the data acquisition phase 10, optical tracking of data for registration purposes is performed. Camera(s) 114 continuously capture images of the surgical field, including reference markers 108 and 128. Detection device 112 monitors levels of radiographic signals in the surgical field. When radiation source 115B is triggered, the radiation detection device 112 identifies radiation emissions as over a predetermined threshold and signals computer 116 to start capturing patient and calibration target pose information from the video streams cameras 114. Simultaneously, radiographic image detector 115A captures image 5, e.g. an X-ray. When the radiation detection device 112 indicates that the radiation emission has ended, computer 116 stops capturing pose information. Object recognition software applications within computer 116 recognize the reference markers 108 and 128 within the captured video data, as illustrated by process blocks 11 and 13, respectively, and records for each of the six degrees of freedom reference markers 108 and 128. At substantially the same time, radiographic image detector 115A generates X-ray image 5 which is provided to computer 116. Software algorithms within computer 116 recognizes calibration markers 40 within the X-ray image 5, as illustrated by process block 17. A similar process occur for X-ray image 15, as illustrated by process block 19.

Figure 14:
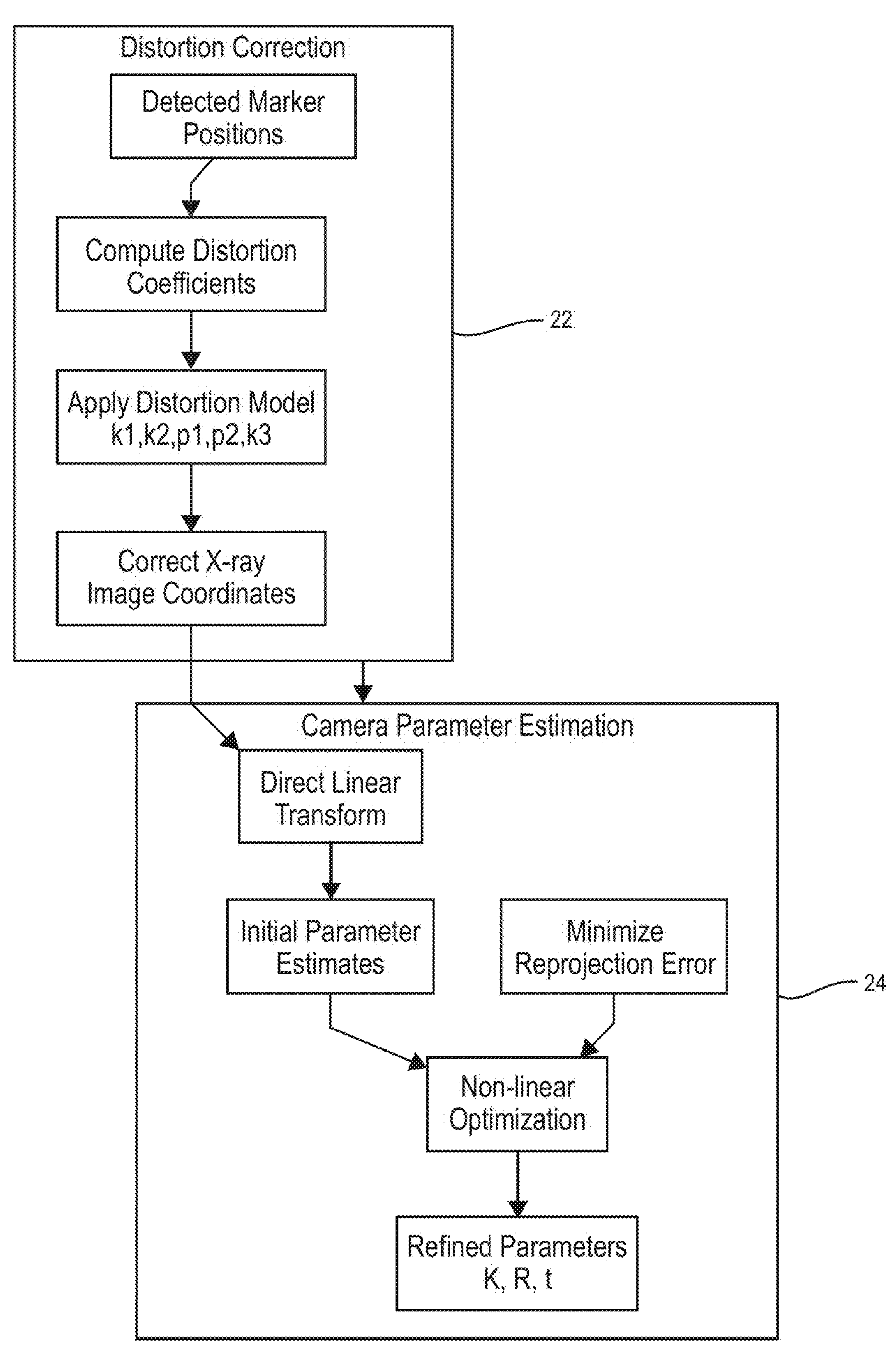
FIG. 14 is a conceptual sub-flow diagram of the distortion correlation and the camera parameter estimation processes of FIG. 2A in accordance with the disclosure.

Process blocks 21, 22, 23, 24, 25, 27 of FIG. 2A illustrate conceptually the process acts involved in system calibration and grid alignment according to the disclosure. FIG. 14 is a conceptual sub-flow diagram of the distortion correlation and the camera parameter estimation processes of FIG. 2A. As illustrated in FIG. 14, process block 22 illustrates the process for distortion correction including the sub processes of detecting marker positions, computing distortion coefficients, applying the distortion model, and correcting x-ray image coordinates. Further, process block 24 illustrates the process for camera parameter estimation as including the sub processes of direct linear transformation, initial parameter estimates, minimizing reprojection error, non-linear optimization and refining parameters, as illustrated in FIG. 14.

Figure 15:
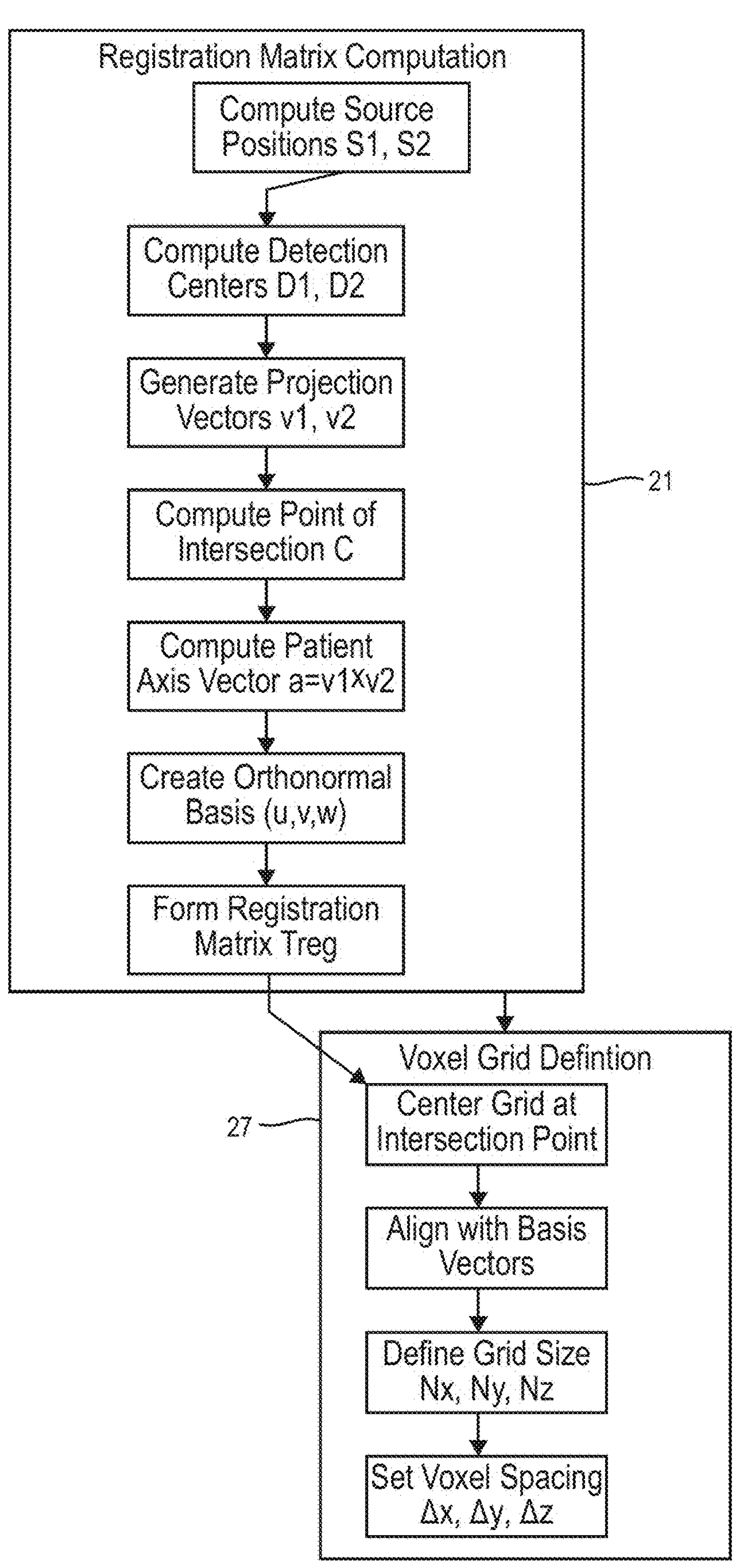
FIG. 15 is conceptual sub-flow diagram of the registration transform calculation and the voxel grid definition processes of FIG. 2A in accordance with the disclosure.

FIG. 15 is conceptual sub-flow diagram of the registration transform calculation and the voxel grid definition processes of FIG. 2A. The process acts and mathematical basis for the computer executable algorithms represented by process blocks 11,13, 27,19, 22 and 24 are explained in greater detail with reference to process flow 105 of FIG. 3. As illustrated in FIG. 15, process block 21 illustrates the process for registration transform computation as including the sub processes of computing source positions S1 and S2, computing detector centers D1 and D2, generating projection vectors V1 and V2, computing a point of intersection C, a patient access vector as a=V1×V2, creating an orthogonal basis (u,v,w), and forming registration transform Treg. Further, process block 27 illustrates the process for camera parameter voxel grid definition as including the sub processes of defining the center of the grid as the intersection point of the vectors, aligning the grid center with the basis vectors, grid size (Nx, Ny, Nz), setting voxel spacings as the individual deltas of (x, y, z), as illustrated in FIG. 15.

The process acts and mathematical basis for the computer executable algorithms represented by process blocks of FIGS. 2A-B are explained in greater detail with reference to process flows of FIGS. 3, 12-16.

Object recognition software, such as Ultralytics YOLO, version 8 or higher, commercially available from www.Ultralytics.com, is used to capture positional information of a surgical instrument 119 relative to the processed pose information of the patient, as illustrated by process block 20. In the surgical navigation phase 16, as described in greater detail herein, the display interface 118 displays the real-time position and movement of surgical instruments relative to the patient, allowing the surgical team to make precise adjustments, without further capturing of patient pose information.

Figure 16:
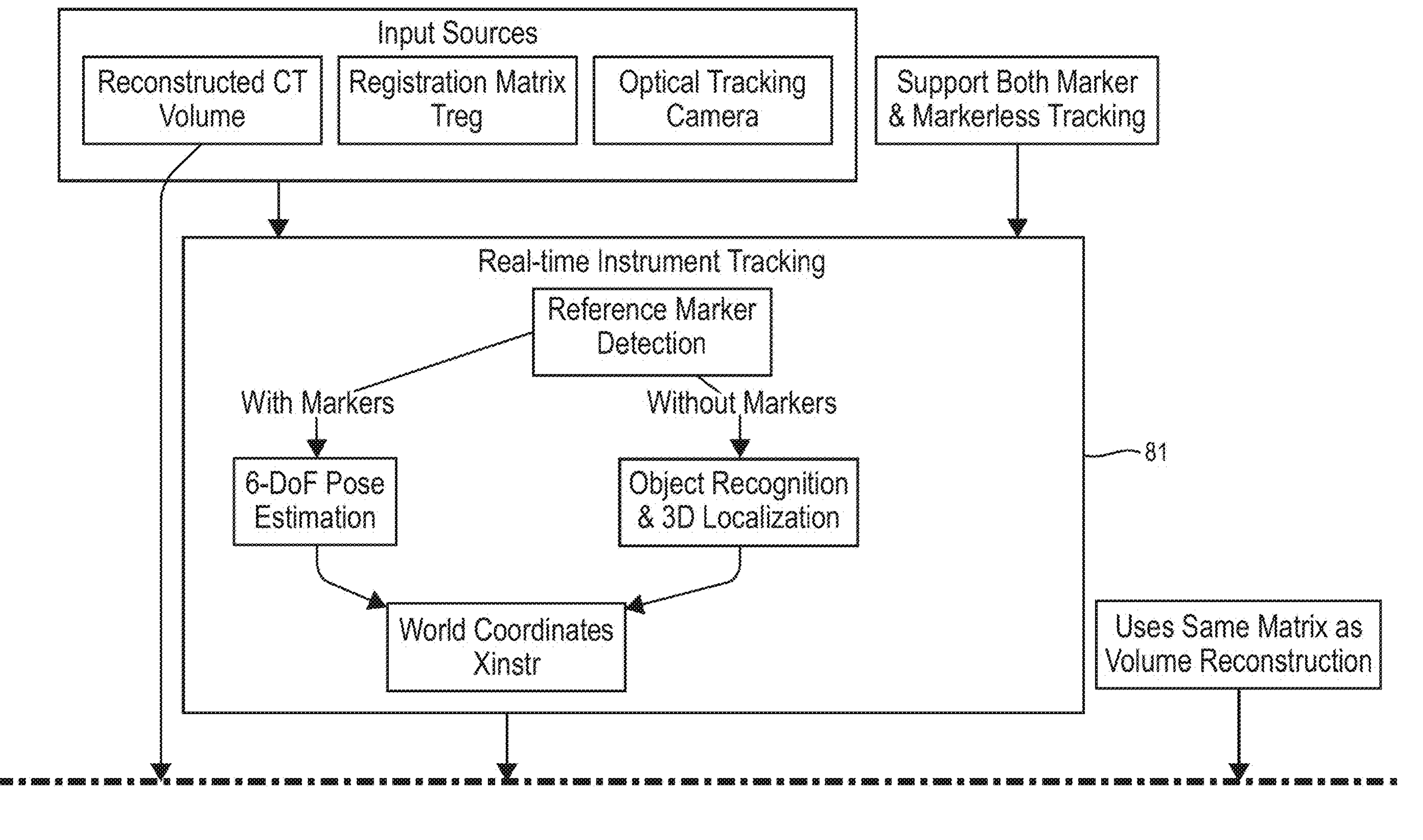
FIG. 16 is conceptual sub-flow diagram of the surgical navigation process processes of FIGS. 2A-B in accordance with the disclosure.
Figure 16:
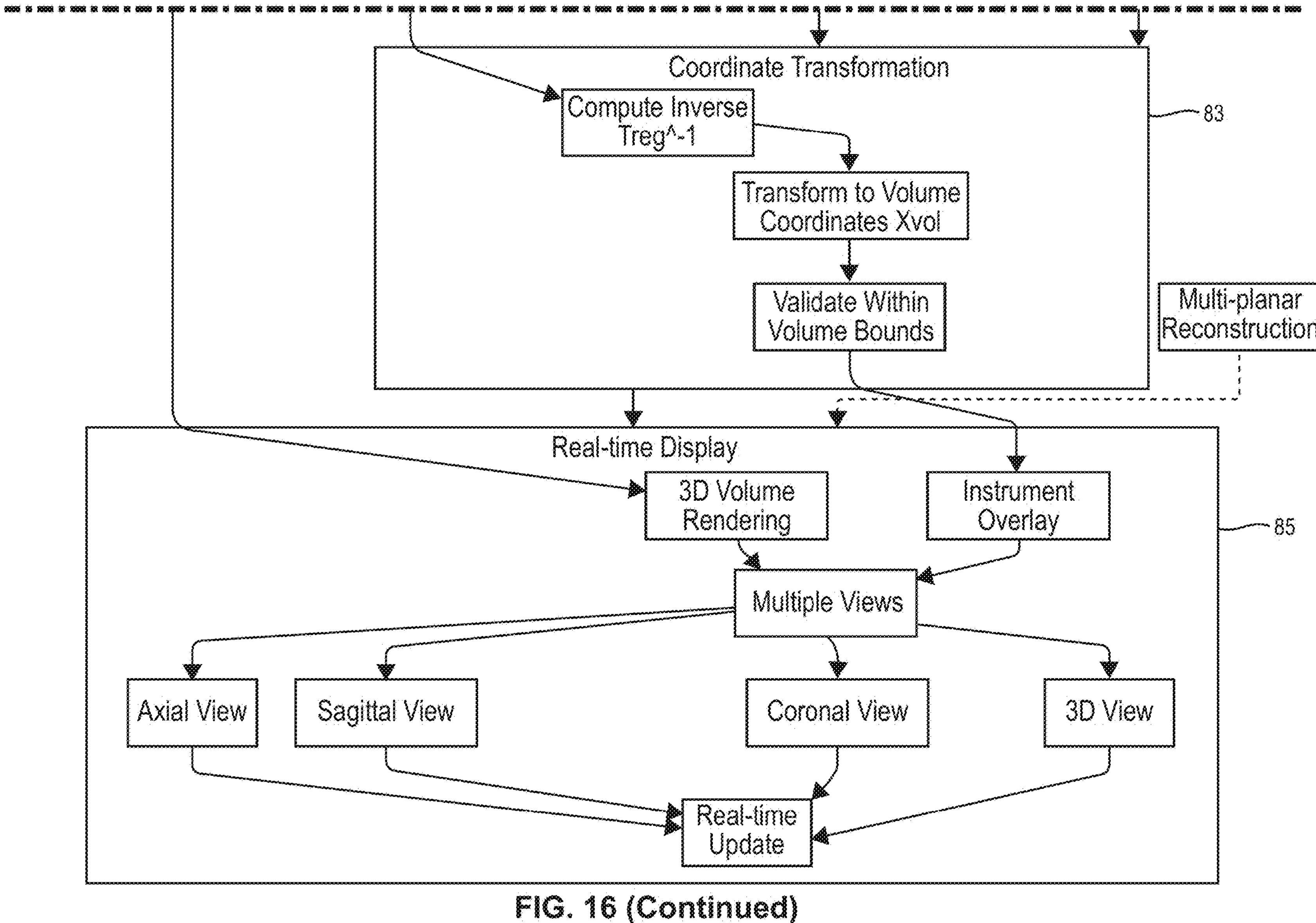

The process acts and mathematical basis for the computer executable algorithms represented by process blocks 11,13, 17,19, 22 and 24 are explained in greater detail with reference to process flow 105 of FIG. 3 which illustrates a process flow for automated reconstruction of a 3D CT volume from 2D X-ray images and display of real-time position and movement of surgical instruments and patient according to the present disclosure. The various acts of process flow 105 may be performed by execution of the computer program instructions 228 stored in the memory 224 and/or storage 227 and controlled by the processor 120 of computer 116, as illustrated in FIG. 16.

Figure 3:
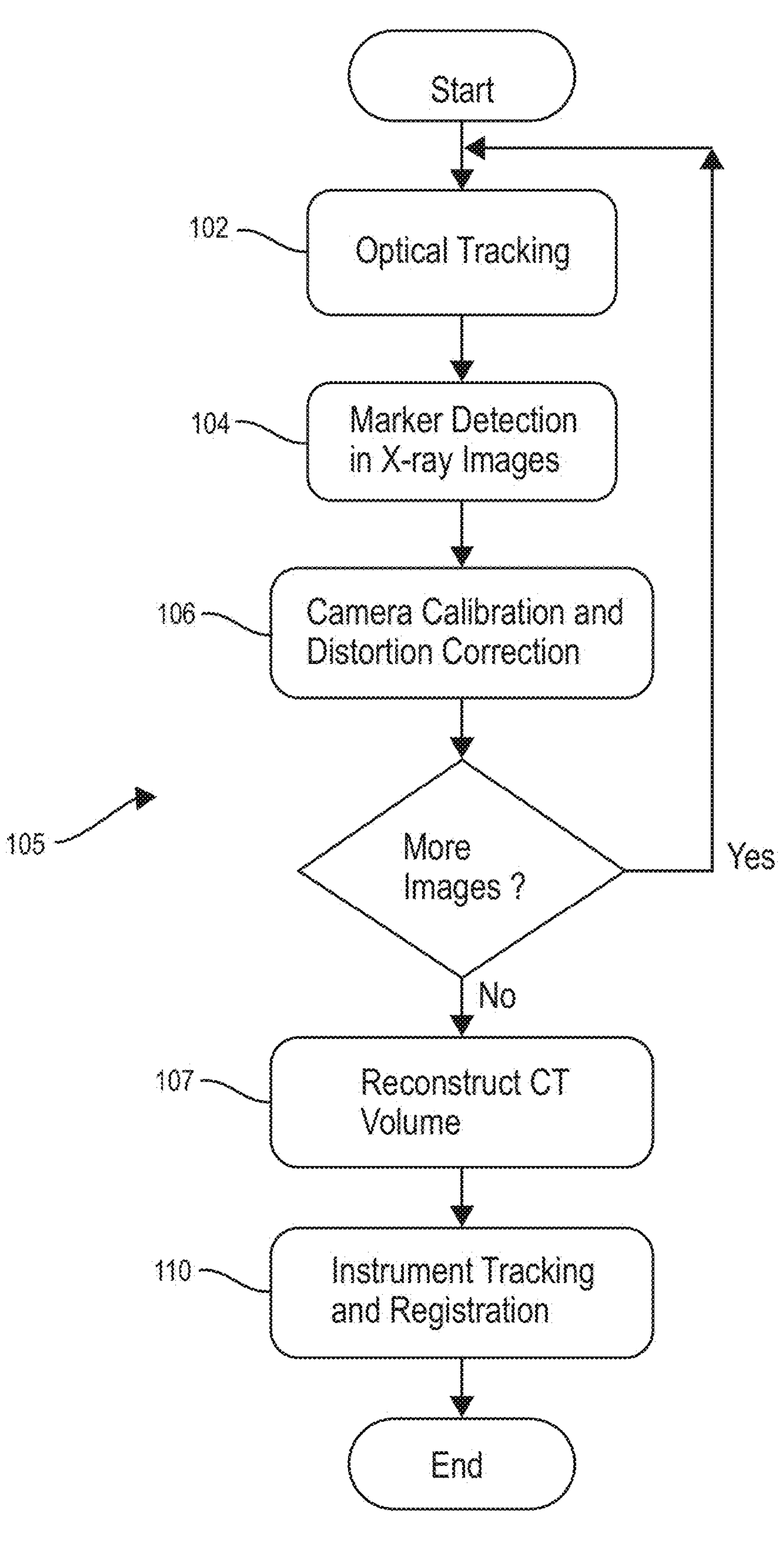
FIG. 3 conceptually illustrates a process flow of the overall methods performed by the surgical navigation system in accordance with the disclosure.
Figure 4:
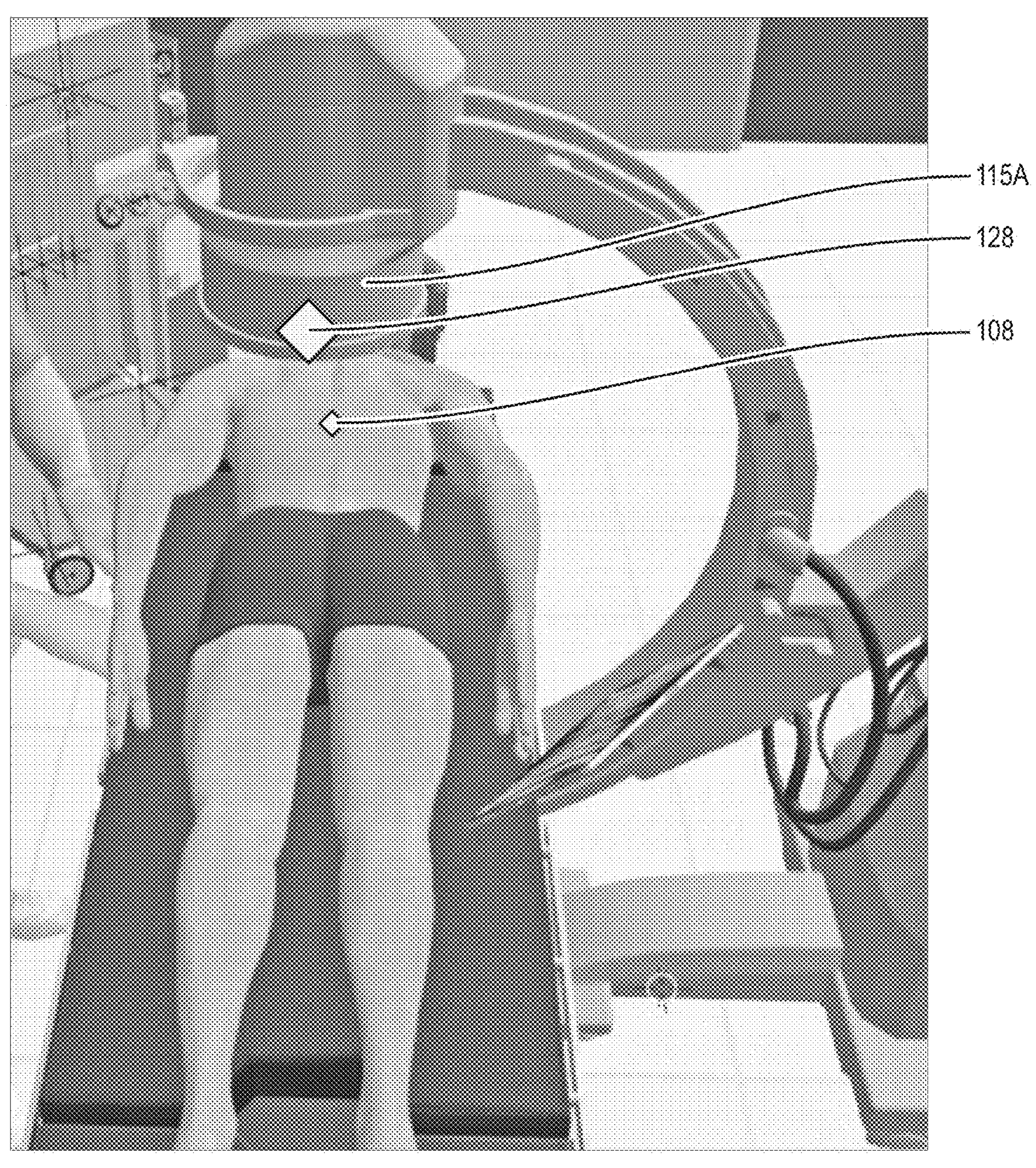
FIG. 4 is a conceptual illustration of the operating environment in which the X-ray C-arm of is posed in an Anterior/Posterior "AP" position in accordance with an illustrative embodiment.
Figure 5:
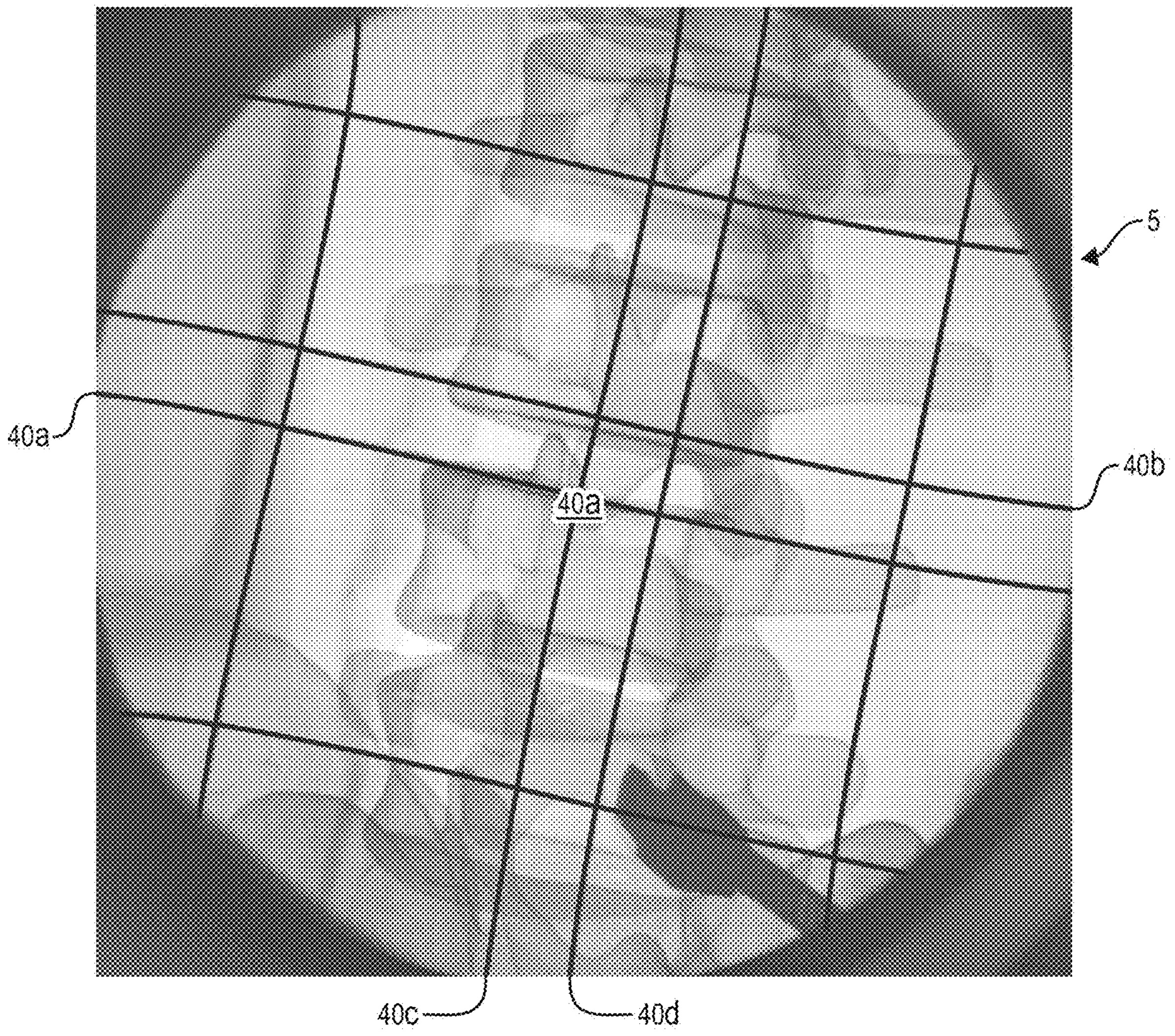
FIG. 5 is a typical "AP" X-ray image generated by a X-ray C-arm in the position of FIG. 4 when used in conjunction with a calibration target having linear markers in accordance with the disclosure.
Figure 6:
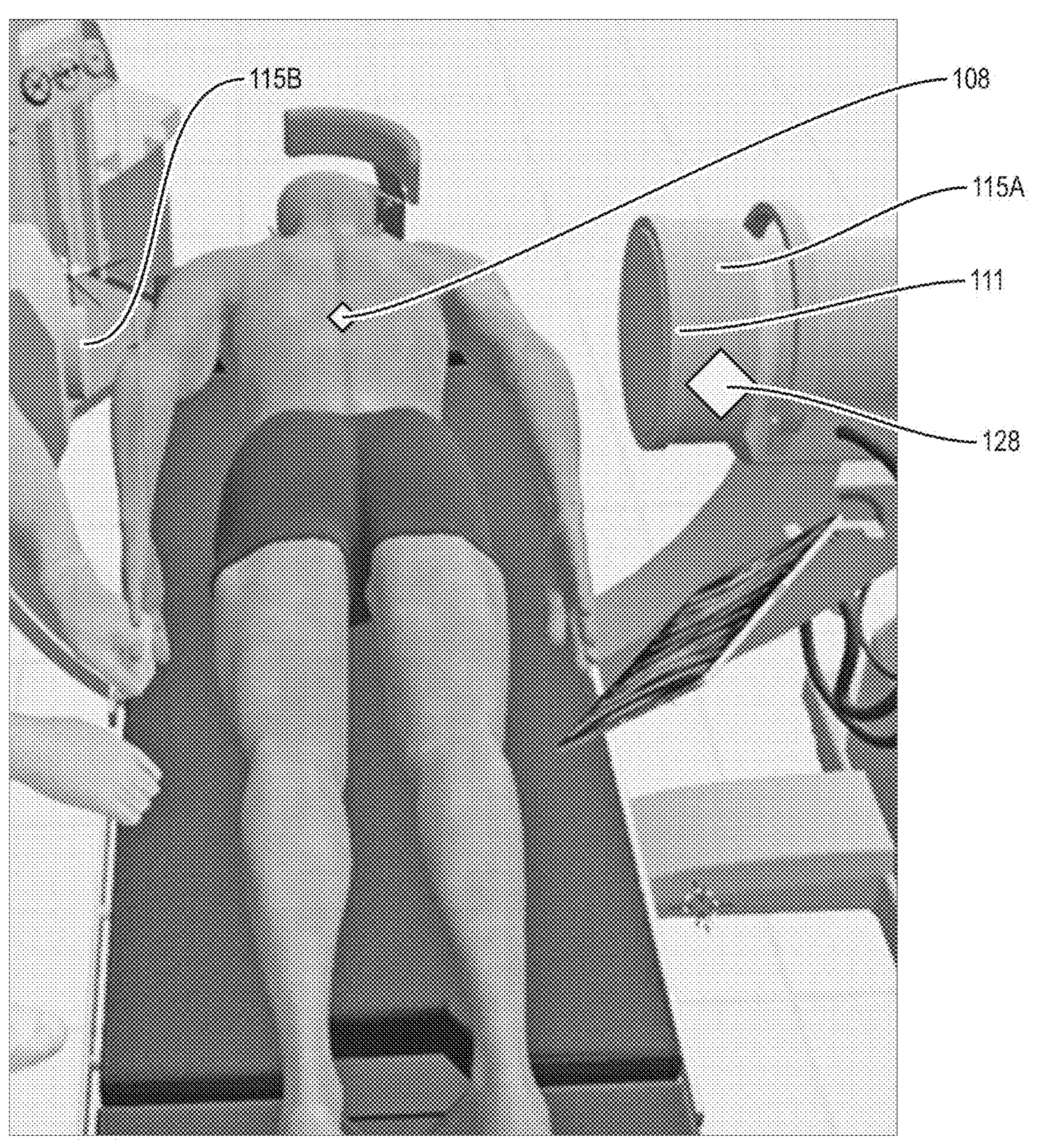
FIG. 6 is a conceptual illustration of the operating environment in which the X-ray C-arm is posed in a "Lateral" position in accordance with with the disclosure.
Figure 7:
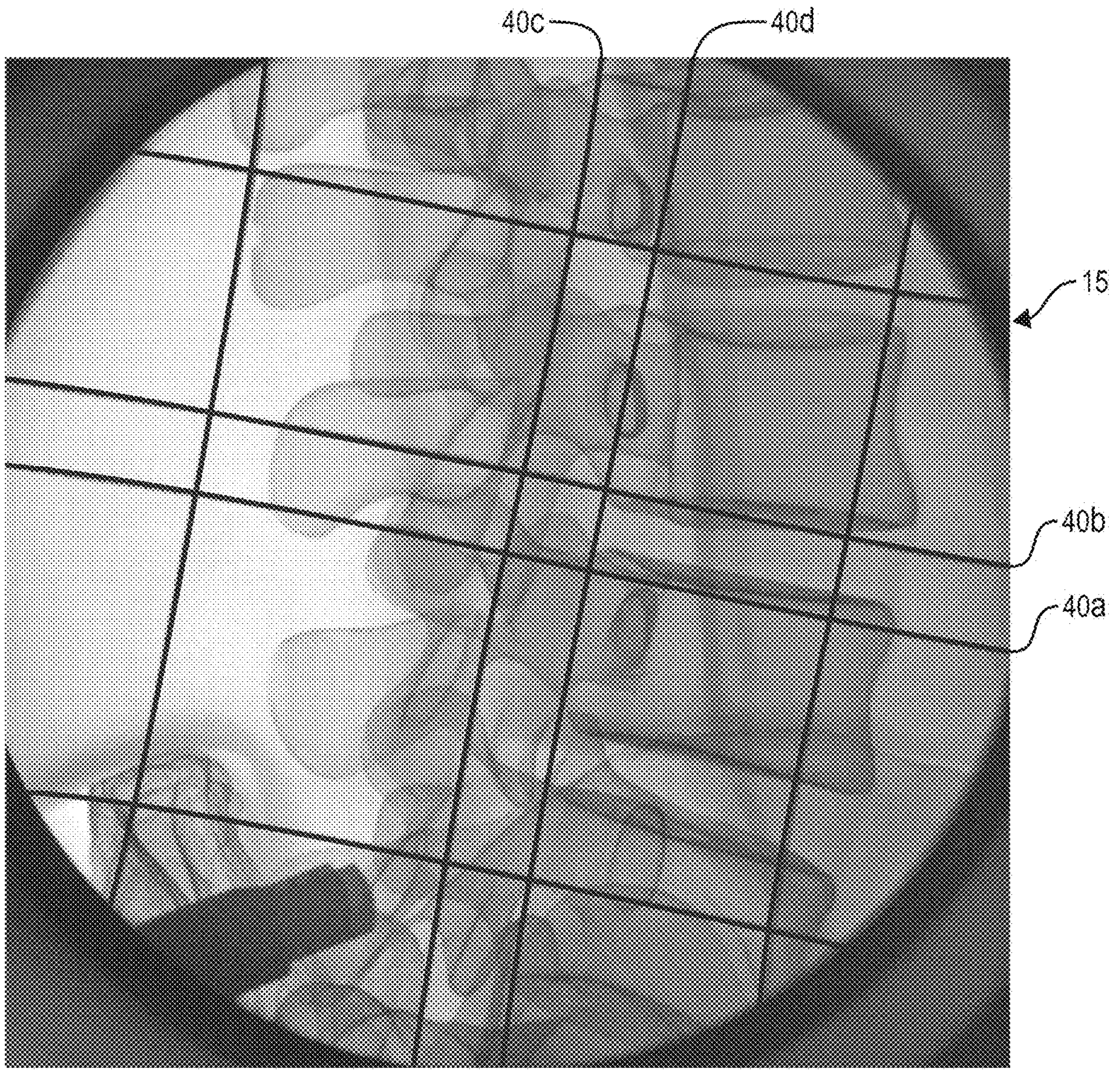
FIG. 7 is a typical "Lateral" X-ray image generated by a X-ray C-arm in the position of FIG. 6 when used in conjunction with a calibration target having linear markers in accordance with the disclosure.

The method of FIG. 3 requires only two 2D X-ray images to perform the reconstruction of the 3D CT volume, but the disclosed method is not limited thereto. The 2D X-ray images 5 and 15 can be obtained using a stand-alone X-ray scanner, a CT scanner, or a C-arm CT scanner. At the time of each 2D X-ray capture, the following process actions occur. At process block 102, optical tracking occurs, where the optical camera 114 detects the reference markers 108 and 128 and records the records the six degrees of freedom (6-DoF) ($R_p$, $t_p$) for the patient reference marker 108 and ($R_c$, $t_c$) for the calibration target marker 128. Optical camera 114 further tracks surgical instruments 119 either through markers attached to the instruments or using object recognition and 3D localization algorithms.

At process block 102, X-ray imaging occurs, with biplanar X-ray image 5 represented by $p_1(u, v)$. The calibration markers 40 within the calibration target 111A are visible in X-ray image 5. A similar process occurs for X-ray image 15 represented by $p_2(u, v)$. Images 5 and 15 captured from different orientations, typically at right angle to each. The calibration markers 40 within the calibration target 111A are also visible in X-ray image 15.

At process block 104, computer executable instructions detect the 2D positions $$x_{i,k}^{distorted}$$

of the intrinsic calibration markers wires 40 in each X-ray image 5 and 15. The positions of these wire 40 are associated with their known 3D coordinates $X_k$.

At process block 106, computer executable instructions perform camera calibration and distortion correction. Using the correspondences between $X_k$ and $$x_{i,k}^{distorted},$$

the intrinsic transform K, distortion parameters D, and extrinsic parameters ($R_i$, $t_i$) for each X-ray projection are computed. Non-linear distortions in the X-ray images are determined and corrected using the calibration wire markers 40, as further described in co-pending U.S. patent application Ser. No. 18/974,359, entitled "Wire-Based Calibration Apparatus for X-ray Imaging Systems", filed on an even date herewith.

At process block 110, computer executable instructions perform instrument tracking and registration occurs. The registration transform that transforms instrument coordinates into the volume coordinates is computed and the registration transform is used to track surgical instruments within the reconstructed 3D volume.

A detailed explanation of the mathematical relationships of the various metrics processed as represented by process blocks 102 to 110, as performed by computer instructions executing in computer 116, is provided below. To describe the mathematical relationships, the following notation is defined:

Coordinate Systems:
- world coordinate system is a fixed reference frame in which all other coordinate systems are defined.
- patient coordinate system is attached to the patient, defined by the patient reference marker 108.
- calibration target coordinate system is attached to the calibration target, defined by reference marker 128.
- camera coordinate system is attached to the optical camera(s); with multiple cameras, the output of each optical camera is transformed into a common camera coordinate system.
- detector coordinate system is attached to the radiographic image detector.
- volume coordinate system 70 is defined by the voxel grid 45 centered at the point of intersection 53 and aligned with basis vectors 50 and 51 derived from the image projection vectors 42 and 44.

Points and Projections:
- $X=[X, Y, Z, 1]^T$: homogeneous coordinates of a 3D point in space.
- $x=[u, v, 1]^T$: homogeneous coordinates of a 2D point in the image plane.

Matrices and Vectors:
- K: Intrinsic camera transform of the radiographic imaging system.

$K_{opt}$: Intrinsic camera transform of the optical camera.

D: Distortion coefficients for modeling non-linear distortions.

R, t: Rotation transform and translation vector (extrinsic parameters) relating world and camera coordinates.

P=K[R|t]: Projection transform mapping 3D points to 2D image points.

Functions:

$f(X)$: Object function representing the 3D volume to be reconstructed.

$p_i(u, v)$: X-ray projection image i.

Optical Camera System

The optical camera system of cameras 114 are modeled using a pinhole camera model, which provides a linear relationship between a 3D point and its projection onto the image plane. The projection equation is shown in Equation (1):

$$x \sim K_{opt}[R_{opt} \mid t_{opt}]X \tag{1}$$

Where:

$K_{opt}$ is the intrinsic transform of the optical camera, containing parameters such as focal length and principal point.

$R_{opt}$ and topt are the rotation transform and translation vector that transform points from the world coordinate system to the camera coordinate system.

The symbol ~indicates equality up to a scalar factor, accounting for the homogeneous coordinates.

Understanding the projection geometry of the optical camera is essential for accurately determining the poses of the reference markers and surgical instruments. By establishing this relationship, the disclosed system transforms points between coordinate systems and accurately track the positions and orientations of the patient, calibration target, and instruments.

Reference Markers and Coordinate Transformations

For the patient marker 108, let $X_p$ be the position of a point in the patient coordinate system 62. The optical camera(s) 114 capture the patient reference marker 108, providing its pose ($R_p$, $t_p$) relative to the camera coordinate system. For calibration target marker 128, let $X_c$ represents the position of a point in the calibration target coordinate system. The optical camera(s) 114 provide the pose ($R_c$, $t_c$) of the calibration target's reference marker 128 or reference marker on the sidewall of calibration target. For surgical instruments 119, the positions of surgical instruments $X_{instr}$ can be obtained either with reference arrays for instruments equipped with optical markers detectable by the camera(s) 114, providing poses ($R_{instr}$, $t_{instr}$), or without reference arrays using object recognition and 3D localization algorithms to estimate the instrument poses relative to the patient reference marker 108.

Transformation Between Coordinate Systems

To relate points in the calibration target coordinate systems and instrument coordinate systems to the patient coordinate system, the following transformations shown in Equations (2) and (3) are used:

$$X_p = R_{pc}X_c + t_{pc} \tag{2}$$

$$X_p = R_{pinstr}X_{instr} + t_{pinstr} \tag{3}$$

-continued

Where:

$$R_{pc} = R_p R_c^T,\ t_{pc} = t_p - R_{pc}t_c$$

$$R_{pinstr} = R_p R_{instr}^T,\ t_{pinstr} = t_p - R_{pinstr}t_{instr}$$

Note that since rotation matrices are orthogonal ($R^{-1}=R^T$), the inverse and transpose are equivalent.

Accurate transformation between coordinate systems facilitates aligning the calibration markers and surgical instruments with the patient's coordinate system. This alignment ensures that the computed poses of the X-ray projections and instruments are consistent with the patient's anatomy, enabling precise navigation.

Detection of Calibration Markers in X-Ray Images

In each X-ray image $p_i(u, v)$, image processing algorithms are employed to detect the 2D positions $$x^{distorted\ i,k}$$

calibration markers. These positions correspond to known 3D points $X_k$ in the calibration target's coordinate system. The relationship between the known 3D points and their image projections is given by:

$$x_{i,k} \sim K[R_i \mid t_i]X_k^{world} \tag{4}$$

Where $$X_k^{world}$$

are the calibration marker coordinates transformed into the world coordinate system:

$$X_k^{world} = R_c X_k + t_c \tag{5}$$

However, when accounting for non-linear distortions, the projection equation becomes:

$$x_{i,k}^{distorted} = Distort\big(K[R_i \mid t_i]X_k^{world},\ D\big) \tag{6}$$

Where:

D represents the distortion coefficients modeling radial and tangential distortions.

Distort(·) is a function that applies the distortion model to the projected points.

By establishing correspondences between the detected 2D positions and known 3D coordinates, and accounting for non-linear distortions, the intrinsic and extrinsic parameters of the radiographic imaging system, as well as the distortion coefficients, can be solved. This calibration enables accurately modeling the radiographic image vectors 50 and 51 and reconstructing the 3D volume 55, especially when image intensifier systems that introduce significant distortions are used with the radiographic image detector 115A.

Camera Calibration and Distortion Correction

The goal of camera calibration is to determine the intrinsic transform K, distortion coefficients D, and the extrinsic parameters ($R_i$, $t_i$) for each X-ray projection i. This process ensures that the system can accurately model the projection geometry, correct for non-linear distortions, and relate image points to points in 3D space.

The disclosed algorithm for calibration includes the following process acts:

Data Collection:

Collect a set of distorted image points $$\{x_{i,k}^{distorted}\}$$

corresponding to the detected calibration markers 40 in each X-ray image 5 and 15.

Ensure that a sufficient number of markers 40 are detected to provide a well-constrained system, covering the image plane to model distortions effectively.

Correspondence Establishment:

Transform the known 3D coordinates $X_k$ from the calibration target coordinate system to the world coordinate system using the pose ($R_c$, $t_c$):

$$X_k^{world} = R_c X_k + t_c$$

Establish correspondences between each distorted image point $x_{i,k}^{distorted}$ and its transformed 3D point $$X_k^{world}.$$

Initial Estimation Using Direct Linear Transformation (DLT):

Correct the distorted image points using an initial guess of the distortion coefficients to obtain undistorted points $x_{i,k}$.

Set up the projection equations for each correspondence:

$$x_{i,k} \sim K[R_i \mid t_i] X_k^{world}$$

Convert the equations into a linear system and solve for the parameters using singular value decomposition (SVD).

Obtain an initial estimate of K, D, $R_i$, and $t_i$.

Nonlinear Optimization (Refinement):

Define the reprojection error as:

$$E = \sum_{i,k} \left\| x_{i,k}^{distorted} - Distort\left(\pi\left(K, R_i, t_i, X_k^{world}\right), D\right) \right\|^2$$

Where π is the projection function mapping 3D points to 2D image points using the current estimates.

Use nonlinear optimization techniques, e.g., Levenberg-Marquardt algorithm,) to minimize the reprojection error E.

Update the estimates of K, D, $R_i$, and $t_i$ iteratively until convergence.

Validation:

Assess the accuracy of the calibration by projecting the 3D points using the calibrated parameters and comparing them to the detected distorted image points.

Compute statistical measures such as the mean reprojection error to quantify the calibration quality.

Intrinsic Parameters and Distortion Coefficients

Intrinsic Transform K:

$$K = \begin{bmatrix} f_x & 0 & c_x \\ 0 & f_y & c_y \\ 0 & 0 & 1 \end{bmatrix} \quad (7)$$

Where:

$f_x$, $f_y$ are the focal lengths in pixels along the x and y axes.

$c_x$, $c_y$ are the coordinates of the principal point.

Distortion Coefficients D:

$$D = [k_1, k_2, p_1, p_2, k_3] \quad (8)$$

Where:

$k_1$, $k_2$, $k_3$ are radial distortion coefficients.

$p_1$, $p_2$ are tangential distortion coefficients.

Precise calibration, including distortion correction, ensures that the geometric relationships between the 3D scene and the 2D images are accurately captured. Correcting non-linear distortions is essential when using X-ray image intensifier systems, as these distortions can significantly affect the accuracy of the back-projection and reconstruction processes.

Reconstruction of 3D CT Volumes from X-Ray Projections

FIGS. 10-13 illustrate a process for automated reconstruction of a 3D CT volume from 2D X-ray images and display of real-time position and movement of surgical instruments and patient according to the present disclosure. The various acts of process flow 130 may be performed by execution of the computer program instructions 228 stored in the memory 224 and/or storage 227 and controlled by the processor 120 of computer 116, as illustrated in FIG. 14.

Figure 10:
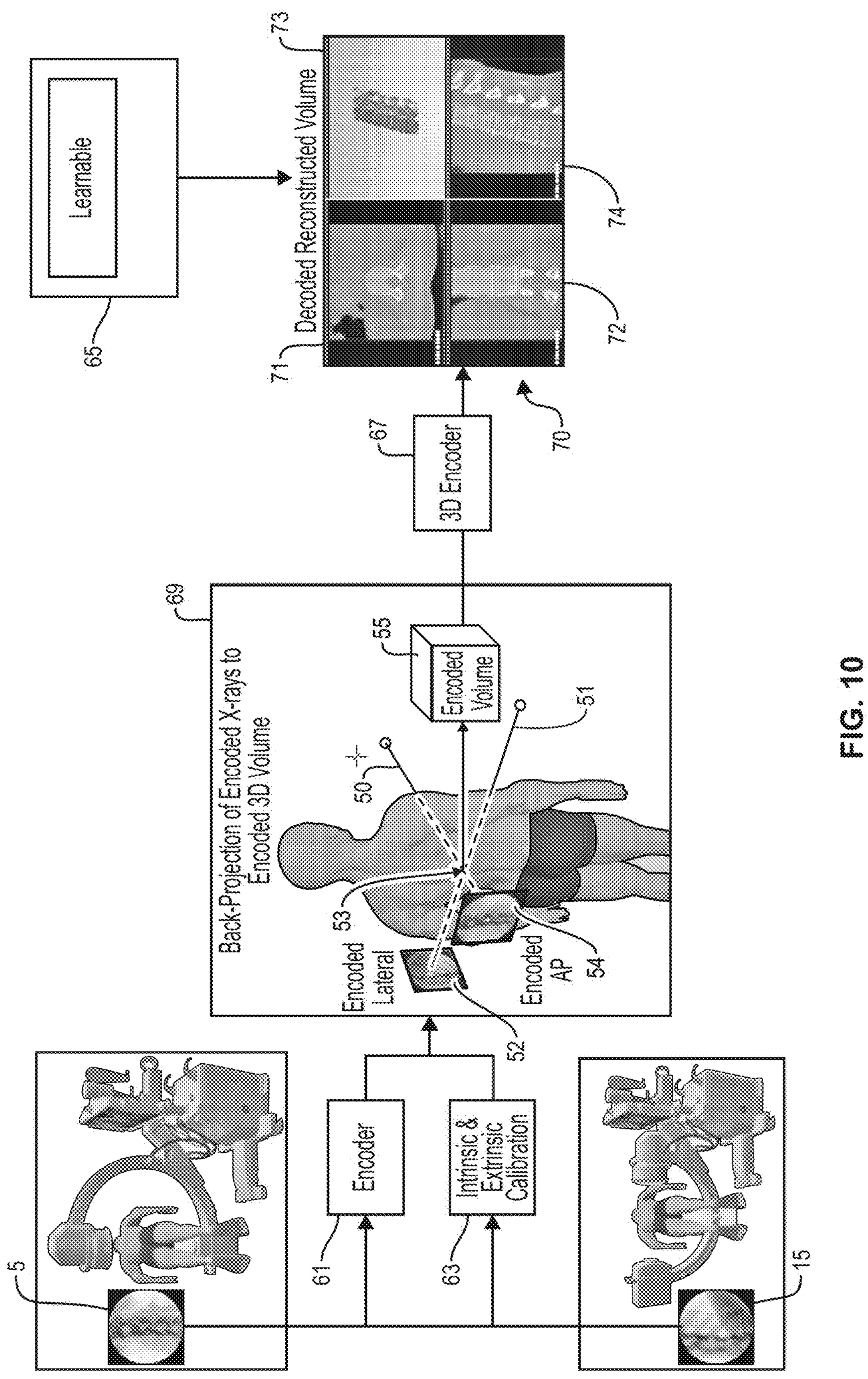
FIG. 10 is a conceptual flow diagram of the processes performed for reconstruction of 3D volumes from biplanar X-ray projections in accordance with an illustrative embodiment.
Figure 11A:
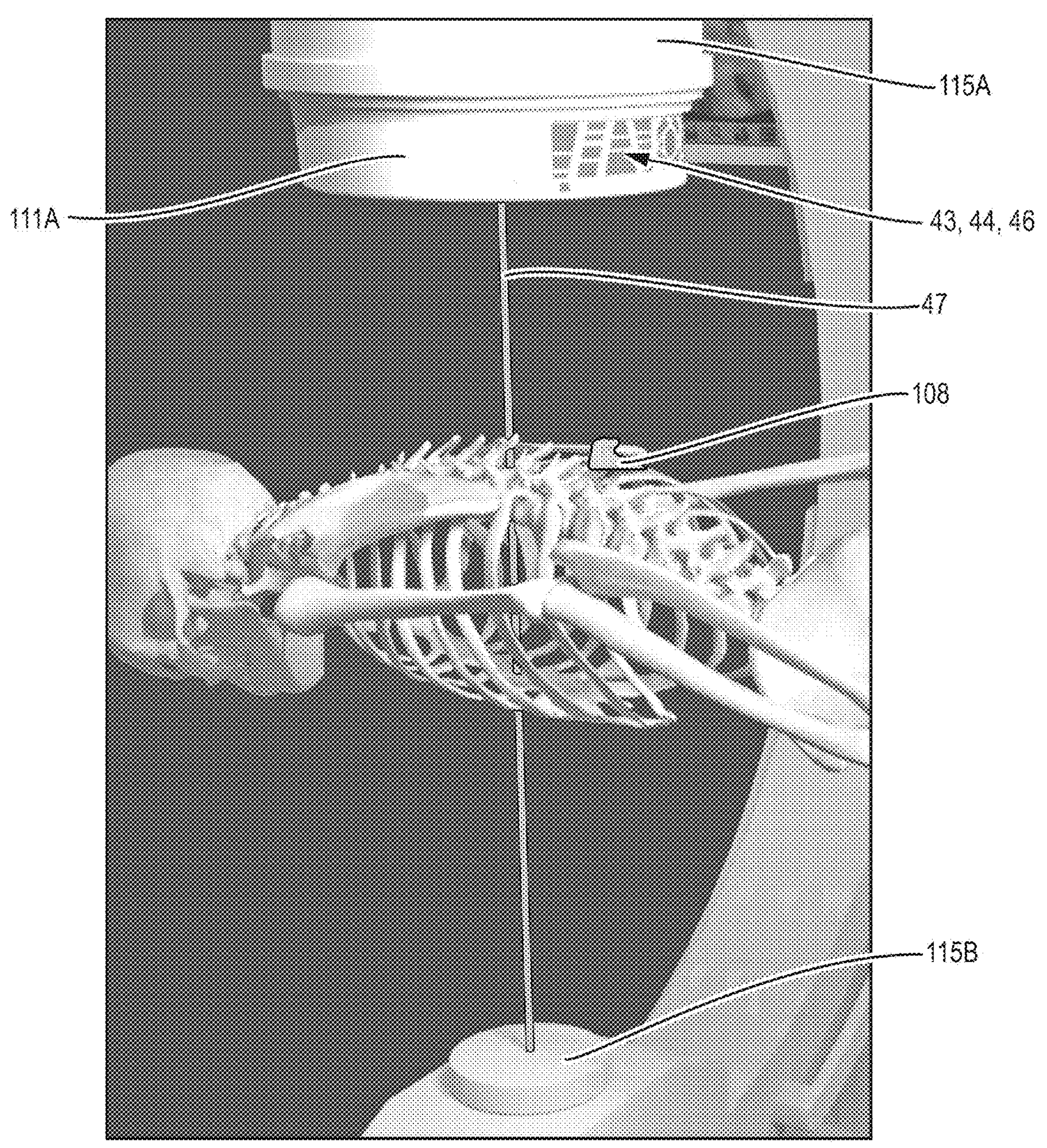
FIGS. 11A-C illustrates conceptually the relationship between computed central rays of by biplanar images and the voxel grid in accordance with the disclosure.
Figure 11B:
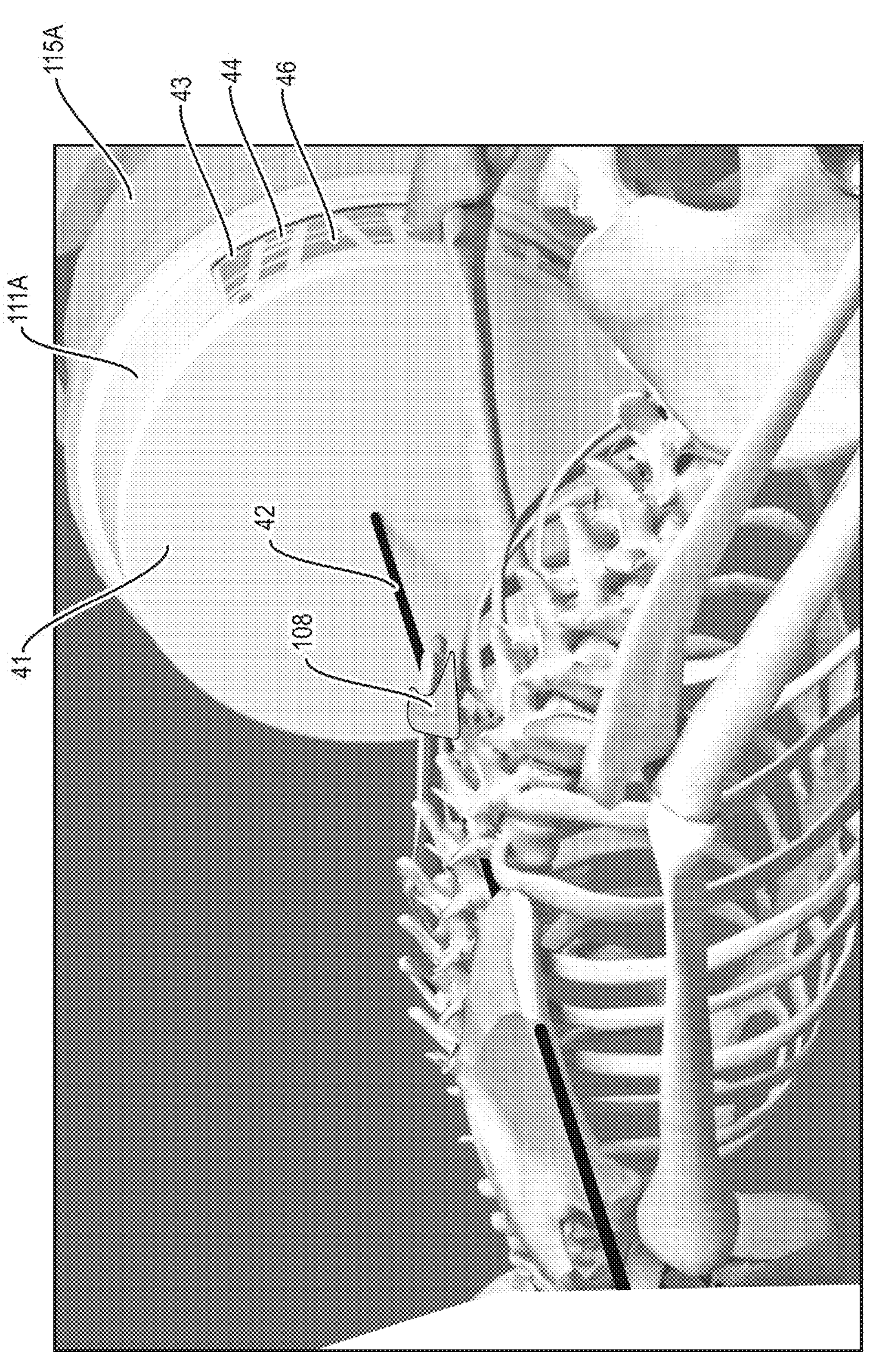
Figure 11C:
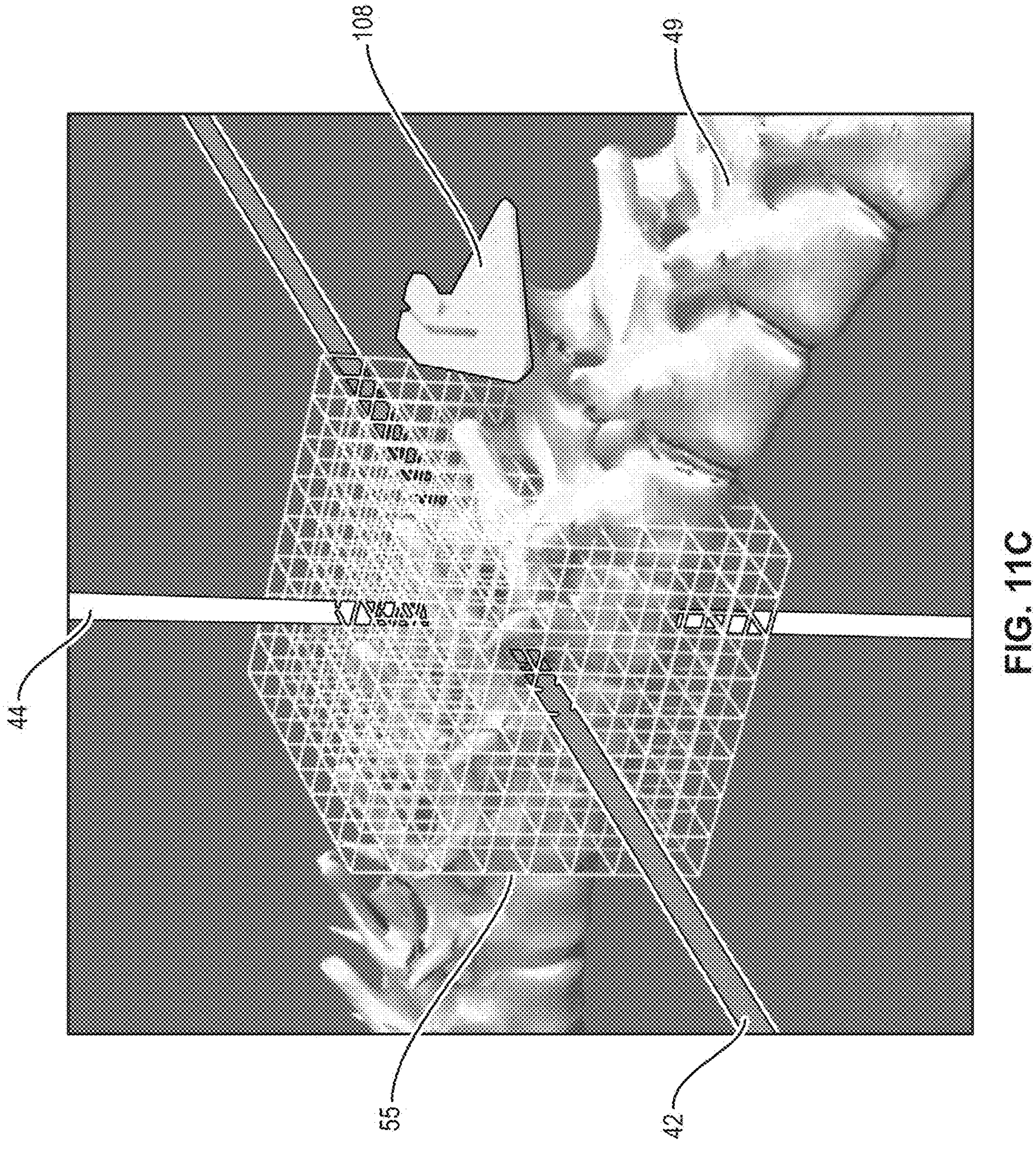

Once the X-ray images are captured, computer executable instructions perform reconstruction of a 3D CT volume 70. The calibrated poses ($R_i$, $t_i$) and intrinsic transform K are used to model X-ray projections using a generalized Radon transform, as further described herein. As illustrated in FIG. 10, a pair of radiographic images 5 and 15 are encoded as illustrated by encoder process block 61 and calibrated for intrinsic and extrinsic distortions, as illustrated by calibration process block 63. From the resulting pair of encoded radiographic images of 52 and 54, image projections are used to form basis vector 50 and 51, and their intersection at a central point 53 used for generating the registration transform, as illustrated by process block 69. The encoded radiographic images of 52 and 54 are back projected into a encoded volume 55 which is then decoded, as illustrated by process block 67, into a three-dimensional volume 70 capable of multiplanar views, including axial, sagittal, coronal, and 3D views of the three-dimensional volume. Back-projection and deep learning techniques may be used to reconstruct the 3D volume of CT quality images from the biplanar X-ray images 5 and 15. The three-dimensional volume 70 may be generated with the assistance of deep learning module 65, as illustrated. FIGS. 11A-C illustrate conceptually the relationship between computed central rays 42 and 47 of the radiation imaging system, the reference marker 108, the reference marking on the calibration target 111A, and the voxel grid 45 relative to a portion of patient anatomy 49.

Figure 12:
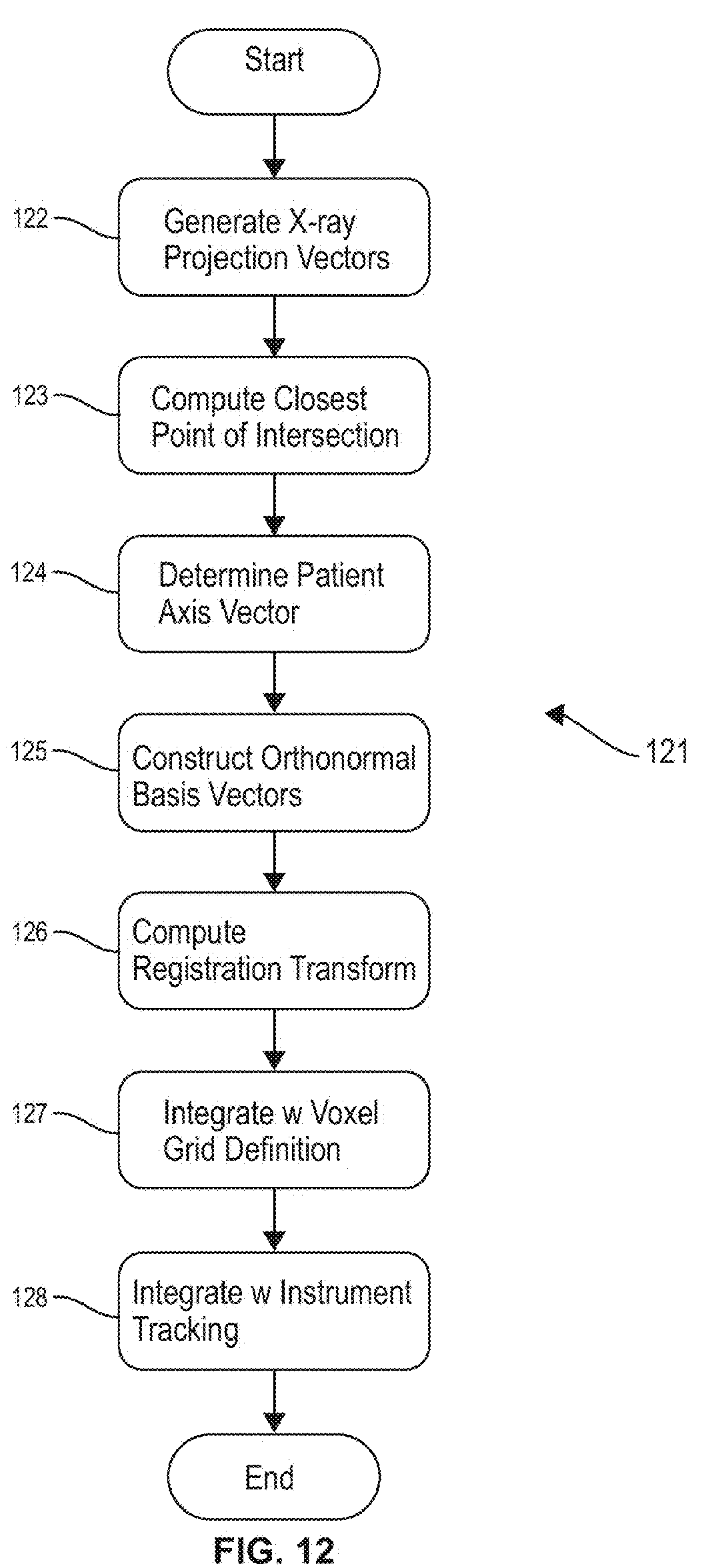
FIG. 12 is a flow diagram of the processes performed for generating a registration transform in accordance with the disclosure.
Figure 13:
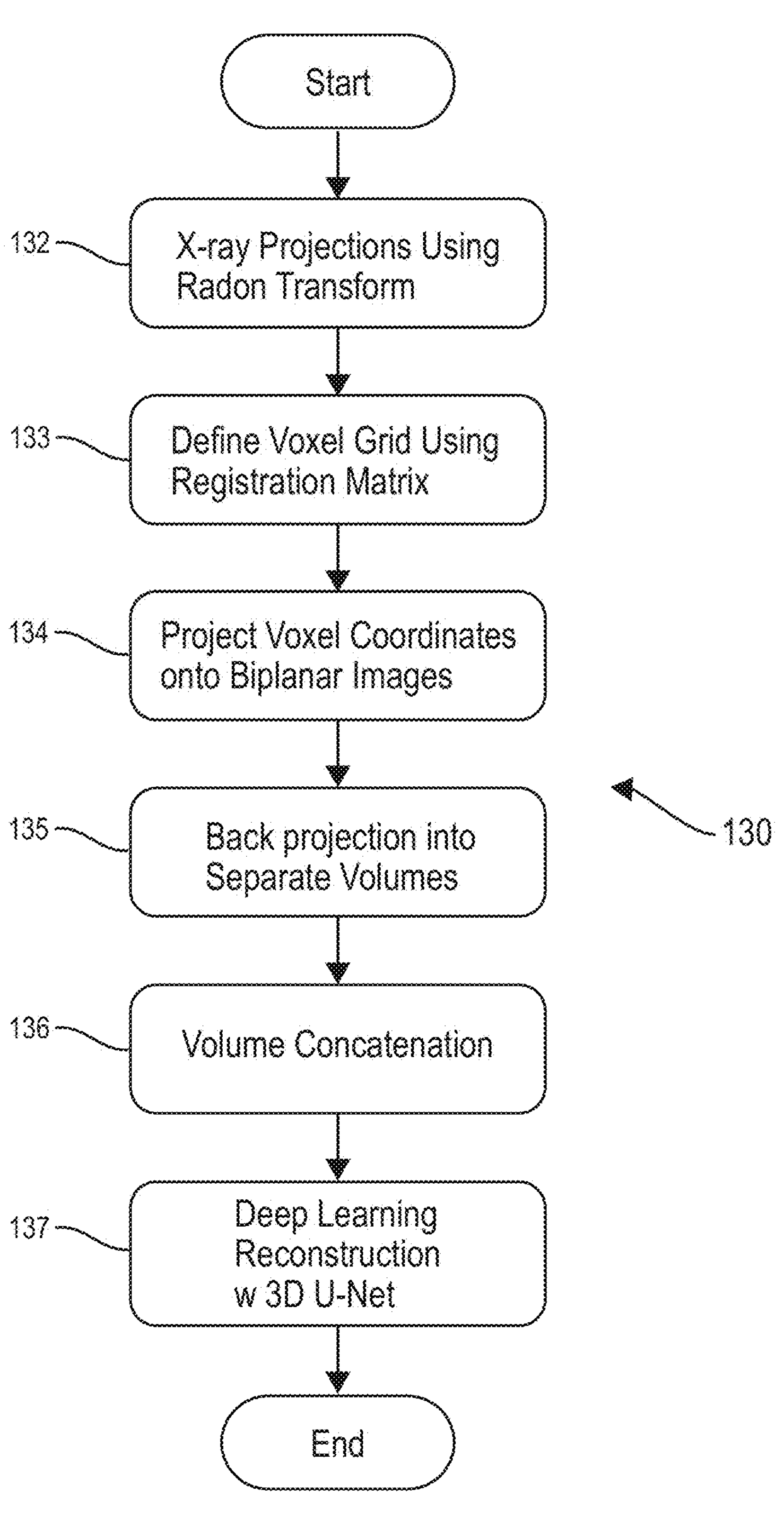
FIG. 13 illustrates conceptually the process for generation of volume of a subject's anatomical elements in accordance with the disclosure.

The algorithmic acts of reconstruction the 3D volume, as represented by process block 107 of FIG. 3, are described below in greater detail with reference to flowchart 121 of FIG. 12. With the calibrated poses ($R_i$, $t_i$), intrinsic transform K, and distortion coefficients D, the system can reconstruct the 3D CT volume $f_{out}(X_{vox})$ from the two X-ray projections $p_1(u, v)$ and $p_2(u, v)$. The reconstruction process of the 3D CT volume is as follows. At process block 132 computer executable instructions perform modeling of the X-ray projections using the generalized Radon Transform to represent the projections based on the object's attenuation properties. The X-ray projections are modeled by integrating the object function $f(X)$ along rays defined by the imaging geometry. For each projection i:

$$p_i(u, v) = \int_{l_{min}}^{l_{max}} f(S_i + l\, d_i(u, v))\, dl \tag{9}$$

Where:

$S_i$ is the position of the X-ray source for projection i.

$d_i(u, v)$ is the unit direction vector from the X-ray source to the detector pixel at (u, v).

$l_{min}$ and $l_{max}$ define the limits of integration along the ray, typically encompassing the region of interest.

The generalized Radon transform accounts for the arbitrary poses and geometries of the imaging system, which is essential when dealing with a mobile C-arm that can assume various orientations. Modeling such projections accurately facilitates greater fidelity of the reconstruction.

At process block 133 computer executable instructions perform definition of a 3D grid of voxel coordinates using the registration transform, centered at the point of intersection and aligned with the basis vectors. An essential step in the reconstruction process is the definition of a 3D grid of voxel coordinates that represents the volume to be reconstructed. The voxel grid is defined using the registration transform $T_{reg}$, ensuring consistency between the navigation and reconstruction components.

To define the Voxel Grid let $N_x$, $N_y$, $N_z$ be the number of voxels along each axis, and $\Delta x$, $\Delta y$, $\Delta z$ be the voxel sizes. The coordinates of each voxel $X_{vox}$ are computed as:

$$X_{vox}(i, j, k) = T_{reg}\begin{bmatrix} \left(i - \frac{N_x}{2}\right)\Delta x \\ \left(j - \frac{N_y}{2}\right)\Delta y \\ \left(k - \frac{N_z}{2}\right)\Delta z \\ 1 \end{bmatrix} \tag{10}$$

Where i=0, 1, . . . , $N_x-1$, and similarly for j and k.

This formulation ensures that the voxel grid is centered at the point C and aligned along the basis vectors (u, v, w) defined by the registration transform. An additional motivation for defining the voxel grid 45 using the registration transform 69 is to ensure consistency between the coordinate systems used for instrument tracking and volume reconstruction. This alignment guarantees that when projected onto the two X-ray images, the voxel grid points will generally fall within the field of view of the X-ray images 5 and 15.

At process block 134 computer executable instructions project each voxel coordinate onto the biplanar images using the calibration matrices, accounting for any corrected distortions. To back-project using these grid points, each voxel coordinate $X_{vox}$ is projected onto each of the biplanar images using their independent intrinsic and extrinsic calibration matrices, accounting for distortion correction:

$$x_i^{distorted} = Distort\left(K\left(R_i X_{vox}^{world} + t_i\right), D\right) \tag{11}$$

Where:

$$X_{vox}^{world}$$

is the voxel coordinate system, obtained by applying $T_{reg}$ to the grid indices.

The projection $$x_i^{distorted}$$

is then normalized to obtain pixel coordinates.

At process block 135 computer executable instructions perform back-projecting each projection into a separate 3D volume, taking into account the imaging geometry. The back-projection for each projection i is performed by accumulating the contributions from the X-ray image $p_i(u, v)$ to each voxel based on the projection of the voxel onto the image:

$$f_{BP_i}(X_{vox}) = p_i(u_i, v_i) w_i(X_{vox}) \tag{12}$$

Where:

$(u_i, v_i)$ are the pixel coordinates corresponding to the distorted projection $$x_i^{distorted}.$$

$w_i(X_{vox})$ is a weighting function accounting for factors such as the distance from the source to the voxel and the angle of incidence.

At process block 136 computer executable instructions perform volume concatenation. That is, combining the back-projected volumes to form a multichannel input. The two back-projected volumes are concatenated along a new dimension (channel axis) to form a multichannel volume $f_{concat}(X_{vox}, C)$:

$$f_{concat}(X_{vox}, c) = \begin{cases} f_{BP_1}(X_{vox}), & c = 1 \\ f_{BP_2}(X_{vox}), & c = 2 \end{cases} \tag{13}$$

At process block 137 computer executable instructions perform cause trained 3D U-Net model 66 to map the concatenated volume 67 to the final 3D volume 70. The disclosed method employs a 3D U-Net U to map the concatenated volume to the reconstructed CT volume:

$$f_{out}(X_{vox}) = U(f_{concat}(X_{vox}, c)) \quad (14)$$

In embodiments, the U-Net architecture is suitable due to its Encoder-Decoder structure comprising a contracting path (encoder) that captures context and an expansive path (decoder) that enables precise localization. The U-Net architecture utilizes skip connections wherein feature maps from the encoder are combined with corresponding decoder layers, preserving spatial information. Further, the U-Net architecture utilizes 3D convolutions wherein the network operates on volumetric data, using 3D convolutional layers to capture spatial relationships in all three dimensions.

Recent advances in deep learning have opened new avenues for solving inverse problems in imaging. Neural networks, particularly convolutional neural networks (CNNs), can learn complex mappings from input data to desired outputs by leveraging patterns learned from large datasets. By integrating optical tracking with advanced computational methods, the disclosed system overcomes traditional limitations and provide practical solutions for intraoperative imaging and instrument tracking. The U-Net architecture is well-suited for medical image reconstruction due to its ability to learn complex mappings from input data to output volumes while preserving spatial resolution. It has been successful in various biomedical imaging tasks, demonstrating robustness and effectiveness.

Integration of Voxel Grid Definition into the Reconstruction Process

By defining the voxel grid using the registration transform $T_{reg}$, the system 110 ensures that the reconstructed volume 70 is in the patient coordinate system 60 and consistent with the instrument tracking frame work. This alignment is needed for accurate navigation and ensures that the voxel grid and registration transform share the same center and basis vectors.

An additional motivation for defining the grid using $T_{reg}$ is to ensure that when projected onto the two X-ray images, the grid points will generally fall within the field of view of the X-ray images. The size of the 3D grid in each dimension is chosen accordingly to guarantee that the projected grid points are within the images.

The projection of voxel coordinates onto the biplanar images establishes a direct connection between the spatial domain of the volume and the image domain of the X-ray projections. This step integrates the generalized Radon transform into the reconstruction process, enabling the deep learning model to effectively learn the mapping from limited-angle projections to the full 3D volume.

Instrument Tracking and Registration

To enable real-time tracking of surgical instruments within the reconstructed volume, the disclosed system 110 computes a registration transform that transforms instrument coordinates (in the patient coordinate system) into the volume coordinates of the generated 3D volume 70. Such registration transform encompasses both positional and rotational information and used to define the center and orientation of the voxel grid 45 for back projection and reconstruction, ensuring consistency between navigation and imaging.

The disclosed system and method facilitates automatic registration of the surgical instruments 119, especially in minimally invasive procedures where the patient's anatomy does not need to be exposed for registration. The disclosed automatic process enhances surgical efficiency and reduces patient trauma.

The algorithmic acts of process block 110 of FIG. 2, are described below in greater detail with reference to flowchart 121 of FIG. 12 and also FIG. 16. At process block 122 execution of computer instructions causes generation of X-ray projection vectors. Specifically, for each X-ray projection i, define a vector $v_i$ from the X-ray source 15A position to the central point of the X-ray detector 15B. The position of the X-ray source $S_i$ in the patient coordinate system is given by:

$$S_i = R_{pc}\left(-R_i^T t_i\right) + t_{pc} \quad (15)$$

The central point of the X-ray detector D; in the patient coordinate system is computed using:

$$D_i = R_{pc}\left(-R_i^T t_i + R_i^T K^{-1} x_0\right) + t_{pc} \quad (16)$$

Where:

$x_0=[c_x, c_y, 1]^T$ is the principal point (center) of the detector in homogeneous coordinates.

The projection vector from the source to the detector center is:

$$v_i = D_i - S_i \quad (17)$$

At process block 123 execution of computer instructions causes computation of the closest point of intersection of the projection vectors. The two vectors $v_1$ and $v_2$ generally do not intersect due to slight misalignments and noise, a point C that minimizes the distance between the two lines defined by $(S_1, v_1)$ and $(S_2, v_2)$ is computed.

Using Scalars s and t that Minimize:

$$\|(S_1 + sv_1) - (S_2 + tv_2)\|^2 \quad (18)$$

Solving this system yields s and t, and the point of closest approach C is taken as the midpoint between $S_1+sv_1$ and $S_2+tv_2$:

$$C = \frac{(S_1 + sv_1) - (S_2 + tv_2)}{2} \quad (19)$$

At process block 124 execution of computer instructions causes determination of the patient axis vector. The patient axis vector a is determined by the cross product of the two projection vectors as in Equation (20):

$$a = v_1 \times v_2 \quad (20)$$

This vector is orthogonal to the plane formed by $v_1$ and $v_2$. At process block 125 computer executable instructions perform construction of orthonormal basis vectors. A set of orthonormal basis vectors (u, v, w) that define the rotation from the patient reference frame to the volume coordinate system are constructed, as set forth in Equations (21), (22) and (23) below.

First Basis Vector Normalize u:

$$u = \frac{v_1}{\|v_1\|} \quad (21)$$

Second Basis Vector Normalize w:

$$w = \frac{a}{\|a\|} \quad (22)$$

Third Basis Vector Compute:

$$v = w \times u \quad (23)$$

At process block 126 computer executable instructions perform computation of the registration transform. The registration transform $T_{reg}$ is a 4×4 homogeneous transformation transform defined as in Equation (24):

$$T_{reg} = \begin{bmatrix} u & v & w & C \\ 0 & 0 & 0 & 1 \end{bmatrix} \quad (24)$$

This transform transforms points from the volume coordinate system to the patient coordinate reg system. Its inverse $T_{reg}^{-1}$ is used to transform points from the patient coordinate system to the volume coordinate system.

At process block 127 computer executable instructions perform integration with voxel grid definition. The voxel grid $X_{vox}$ used in the reconstruction is defined using $T_{reg}$, ensuring that the grid's center and orientation match those used for instrument tracking.

$$X_{vox}^{world} = T_{reg} \begin{bmatrix} \left(i - \frac{N_x}{2}\right)\Delta x \\ \left(j - \frac{N_y}{2}\right)\Delta y \\ \left(k - \frac{N_z}{2}\right)\Delta z \\ 1 \end{bmatrix} \quad (25)$$

At process block 128 computer executable instructions perform integration with instrument tracking. Acquiring the pose of an instrument can be done in multiple ways. If instruments have reference arrays, positions $X_{instr}$ from optical tracking is obtained. If instruments are tracked without reference arrays, object recognition and 3D localization algorithms are used to estimate $X_{instr}$ relative to the patient marker. Also as part of process block 118 transformation to volume coordinates is performed with Equation (26) as follows:

$$X_{vol} = Treg^{-1} X_{instr} \quad (26)$$

where $X_{vol}$ is the position of the instrument in the volume coordinate system, aligning with the voxel grid. Thereafter, the transformed instrument positions can be overlaid onto the reconstructed 3D CT volume, providing surgeons with real-time visualization feedback.

By aligning the instrument positions with the reconstructed volume through the shared registration transform $T_{reg}$, surgeons can navigate instruments accurately relative to the patient's anatomy. The consistent use of $T_{reg}$ for both instrument tracking and voxel grid definition ensures that the coordinate systems are synchronized, enhancing the accuracy and reliability of the surgical navigation system.

The projection of voxel coordinates onto the biplanar images using the disclosed transforms bridges the spatial domain (voxel grid) and the projection domain (X-ray images). Such connection facilitates accurate back projection. By projecting voxel coordinates onto the images, the system accurately accounts for the contribution of each voxel to the projections, respecting the imaging geometry defined by the intrinsic and extrinsic parameters, and corrected for distortions. The voxel-wise correspondence between the spatial domain and the image domain provides the deep learning model 65 with structured input data that reflects the true geometry of the imaging system. This connection facilitates patient coordinate alignment. Since the voxel grid is defined using the registration transform derived from the projection vectors, the reconstructed volume inherently aligns with the patient's anatomy and the instrument tracking system, enabling direct navigation without additional transformations.

FIG. 16 is a further conceptual sub-flow diagram of the surgical navigation phase 16 of FIGS. 2A-B in accordance with the disclosure. In particular, the process acts for process blocks 31 and 33 are illustrated in greater detail in FIG. 16 with the described acts illustrated in process blocks 81, 83 and 85 thereof. Specifically, given the input sources of a reconstructed 3D volume, the computed registration transform and output of the optical tracking cameras process, block 81 represents the steps necessary for real-time instrument tracking for both instruments with marker arrays and without markers. Specifically, process block 81 encompasses the acts of detecting any reference markers on the instruments, and, if markers are detected, determining the six degrees of freedom pose of the instrument. If no markers are detected, object recognition software and 3D localization algorithms are utilized to recognize the instrument pose. The output of either of these instrument positions is transformed into the world coordinate system. Process block 83 illustrates the a subprocesses for coordinate transformation, including computing an inverse of the registration transform, transforming the instrument position to volume coordinates and validating that the transformed instrument coordinates are within the bounds of the 3D volume. Such transformations use the same registration transform as used for the 3D volume reconstruction.

Next, the multi-planar reconstruction is utilized to provide real-time display as illustrated by process block 85. In particular, 3D volume renderings from the reconstructed CT volume and the instrument overlay generated in process block 83 are combined to provide multiples views of the patient anatomy including axle, sagittal, coronal, and 3D views updated in real time as illustrated.

Reconstruction of 3D CT Volumes from Biplanar X-Ray Projections

Disclosed is a mathematical framework and implementation of a system and methods for reconstructing 3D CT volumes from biplanar X-ray projections using deep learning. By concatenating the back projected volumes from two projections and passing them through a neural network, the projections can be encoded into a single 3D volume. The advantages of using the U-Net architecture, including its encoder-decoder structure with skip connections, multi-scale feature extraction, and proven effectiveness in medical imaging, make the U-Net architecture a suitable choice for such task.

By incorporating the Radon transform into the disclosed formulation [of the projections] and utilizing existing tomographic methods for back projection, the gap between traditional reconstruction techniques and modern deep learning approaches is bridged. With sufficient training data, the deep learning model can approximate the true CT reconstruction function, effectively overcoming the limited angle problem.

To accommodate X-ray projections of arbitrary poses using the Radon transform, let f (r) represent the 3D object function, where r=(x, y, z) denotes spatial coordinates in the patient's reference frame, then consider two X-ray projections taken at arbitrary poses, characterized by rotation and translation transformations corresponding to the positions and orientations of the X-ray source and detector, as would be the case with an X-ray C-arm system. For each projection i (with i=1, 2), the 2D projection pi(u, v) is given by the generalized Radon transform, which integrates the object function over lines determined by the imaging geometry:

$$p_i(u, v) = \int_{-\infty}^{\infty} f\left(R_i^{-1}(s_i(u, v) + ld_i) - t_i\right) dl$$

Where:

- Ri is the rotation matrix representing the orientation of the imaging system for pro-jection i.
- ti is the translation vector representing the position of the imaging system for projec-tion i.
- si(u, v) represents the position on the detector plane in the detector's coordinate sys-tem.
- di is the unit direction vector from the X-ray source to the point (u, v) on the detector.
- l is the parameter along the line (ray) from the source to the detector point.

The above formulation generalizes the Radon transform to account for arbitrary poses and geometries of the object image as captured by camera 114. In cases where the geometry simplifies (e.g., parallel beam), the generalized formulation reduces to the classical Radon transform.

Each projection $p_i(u, v)$ can be back projected into a separate 3D volume $f_{BP_i}(x, y, z)$ using existing tomographic back projection methods adapted to the imaging geometry. The back-projection operator integrates the projection data along the paths defined by the imaging system's geometry:

$$f_{BP_i}(x, y, z) = r \text{ Detector } p_i(u, v) w_i(u, v, x, y, z)\, du\, dv$$

Where:

- $w_i(u, v, x, y, z)$ is a weighting function that accounts for factors such as the distance from the source to each voxel and the angle of incidence, as determined by the imaging geometry.

By employing existing tomographic methods, such as filtered back projection reconstruction algorithms adapted to the specific geometry, we can perform the back projection into the two separate volumes that will be concatenated.

After back-projecting each projection into separate volumes, concatenate of the two volumes is done along a new dimension to form a combined volume $f_{concat}(x, y, z, c)$:

$$f_{BP_i}(x, y, z) = \int_{Detector} p_i(u, v) w_i(u, v, x, y, z)\, du\, dv$$

Here, c is the channel index indicating the concatenation of the two volumes.

Concatenating the two back projected volumes before passing them through the deep learning network is used instead of averaging or combining them into a single-channel volume due for a number of advantageous reasons. First, concatenating the two backprojected volumes preserves distinct information. Each projection captures unique structural information from different angles. Concatenation preserves the distinct features present in each volume, allowing the network to access all the raw information. Second, concatenating the two back projected volumes enhances feature extraction. The network can learn to extract and combine features from both volumes in a nonlinear fashion, leveraging the complementary information to improve reconstruction quality. Third, concatenating the two back projected volumes avoids information loss. Averaging or combining the volumes can lead to the loss of critical features or contrasts that are only visible in one projection. Concatenating ensures that no information is discarded prematurely. Fourth, concatenating the two back projected volumes allows for greater flexibility during training of the network. By providing separate channels for each volume, the network has the flexibility to assign different weights and processing strategies to each projection during training. Fifth, concatenating the two back projected volumes improves representation learning. Multichannel input allows the network to learn complex interdependencies between the projections, facilitating a more robust and accurate reconstruction. Sixth, concatenating the two back projected volumes reduces artifacts. Concatenation can help mitigate artifacts that may arise from directly combining incompatible or misaligned features through averaging. Seventh, by concatenating the volumes, the amount of useful information available to the network is maximized, enhancing its ability to learn the mapping from limited projections to the full 3D volume.

Passing Through a 3D U-Net

A 3D U-Net U that maps the concatenated volume to a reconstructed 3D volume can be defined as:

$$f_{out}(x, y, z) = U(f_{concat}(x, y, z, c))$$

The U-Net architecture is particularly well-suited for the reconstruction task due for a number of reasons. First, the U-Net employs an encoder-decoder architecture with symmetric skip connections that allow the network to capture both high-level abstract features and low-level spatial details. Such structure facilitates reconstructing fine anatomical structures in medical images. Second, the U-Net architecture has Multi-Scale Feature Extraction. The U-Net architecture's use of convolutional layers at multiple scales enables the network to learn features across different resolutions, capturing both global context and local details. Third, the U-Net architecture helps to preserve special information. Skip connections help preserve spatial information during the down sampling and ups ampling processes, which is crucial for accurate localization in image reconstruction tasks. Fourth, the U-Net architecture has established proven effectiveness in medical imaging. U-Net has been extensively used and validated in various medical imaging applications, including segmentation and reconstruction tasks, demonstrating its robustness and effectiveness. Fifth, the U-Net architecture is efficient in training with limited data. Due to its design, U-Net can be trained efficiently even with a relatively small amount of training data, which is often a limitation in medical imaging datasets.

Overcoming the Limited Angle Problem with Deep Learning

The limited angle theorem asserts that accurate reconstruction is impossible when projection data is insufficient or limited in angular range. Using only biplanar X-rays (two projections), traditional reconstruction methods would produce incomplete and artifact-laden images due to missing spatial frequency information. A deep learning approach is used to address the Limited Angle Problem. Specifically, by training on a large dataset of biplanar X-rays and their corresponding full CT scans, the deep learning model learns the statistical relationships between limited angle projections and complete 3D volumes. In addition, the neural network implicitly captures prior information about the structure and features of the objects being imaged (e.g., anatomical structures in medical images). Finally, deep learning model can approximate complex, nonlinear mappings that traditional linear reconstruction algorithms cannot, allowing it to infer missing information from the limited projections. By leveraging these capabilities, the deep learning model effectively mitigates the issues posed by the limited angle problem, producing high-quality reconstructions from minimal projection data.

Below is a theoretical justification that, with sufficient training data, the trained model can approximate the true CT reconstruction function for any new set of biplanar X-rays not seen during training.

Problem Setup

Input Space (X): The set of concatenated biplanar X-ray volumes.

Output Space (Y): The set of true CT volumes.

True Mapping ($f$): $f$: X→Y, the (possibly stochastic) function mapping inputs to outputs.

Model ($\hat{f}$): The neural network trained to approximate $f$.

The problem of reconstructing a 3D CT volume from only two X-ray projections is inherntly ill-posed: there are infinitely many 3D volumes that can produce the same biplanar projections. Therefore, traditional reconstruction methods cannot recover the true CT volume uniquely.

However, the following assumptions are made:

Statistical Regularities: The objects being imaged (e.g., human anatomy) exhibit statistical regularities that can be learned from data.

Representativeness of Data: The training data is sufficiently large and representative of the true data distribution.

Model Capacity: The neural network has sufficient capacity to learn the mapping from X to Y.

Given a supervised learning setup where with a training dataset $$\{(x_i, y_i)\}^N,\ i = 1$$

$x_i \in X$ and $y_i \in Y$ are drawn from a joint distribution $P_{X,Y}$, the goal is to learn a function $\hat{f}$ that minimizes the expected loss:

$$R(\hat{f}) = \mathbb{E}_{(X,Y)\sim P_{X,Y}}\left[L\left(\hat{f}(X), Y\right)\right]$$

where L is a suitable loss function (e.g., mean squared error).

The universal approximation theorem states that neural networks with sufficient capacity can approximate any measurable function arbitrarily well on compact subsets of R". However, due to the problem being ill-posed, regularization through data priors is important. By training on a large dataset, the neural network learns the statistical priors inherent in the data, effectively incorporating prior knowledge about the typical structures in Y.

Under the assumption that the training samples are independently and identically distributed (i.i.d.) and the model has sufficient capacity, the empirical risk minimization leads to convergence of the empirical risk $\hat{R}_N(\hat{f})$ to the expected risk $R(\hat{f})$ as $N\to\infty$:

$$\hat{R}_N(\hat{f}) = \frac{1}{N}\sum_{i=1}^{N} L\left(\hat{f}(x_i), y_i\right) \xrightarrow{P} R(\hat{f}) \text{ as } N \to \infty$$

This implies that the model's performance on unseen data approaches its performance on the training data.

Given that the model minimizes the expected loss and has sufficient capacity, it can approximate the true mapping $f$ in the sense that:

$$\lim_{N\to\infty} \mathbb{E}_{X\sim P_X}\left[L\left(\hat{f}(X), f(X)\right)\right] \to 0$$

This convergence is contingent on the model's ability to capture the complexities of $f$ and the richness of the training data.

The disclosed system and method leverages the statistical properties of data to learn a mapping that approximates the true CT reconstruction function. With sufficient and representative training data, a pretrained deep learning model generalizes well to new; unseen biplanar X-rays, effectively overcoming the limitations imposed by the limited angle problem.

Deep Learning Model Training

A deep learning model, e.g., a 3D U-Net, is employed to process the back projected data to enhance reconstruction quality and address limited-angle tomography challenges by learning from prior data. The accuracy of the calibration directly impacts the quality of the 3D reconstruction. Errors in calibration can lead to misalignment of projections and artifacts in the reconstructed volume.

The training process of this system is comprehensive and robust, involving multiple stages of encoding, back-projection, decoding, and iterative refinement. The use of diverse training data ensures that the system is well-equipped to accurately reconstruct 3D volumes in a clinical setting, providing a valuable tool for medical diagnostics and treatment planning.

In embodiments, the deep learning model XX may be trained using a dataset size of 1000 X-ray images with ground truth labels and training parameters having a batch size=16, epochs=50, learning rate=$1\times10^{-4}$. Augmentation may be random rotations (±10°), scaling (±5%), Gaussian noise.

The disclosed method for training creating a reconstructed 3D volume includes the following process flow: A) back-projection wherein each of the two X-ray projections is back-projected into a separate 3D volume using existing tomographic methods adapted to the specific imaging geometry: B) concatenation wherein the two back-projected volumes are concatenated along a new channel dimension to form a multichannel input: and C) deep learning reconstruction wherein the concatenated volume is input into a pre-trained 3D deep learning model, which outputs the reconstructed 3D volume.

The process for training the 3D U-Net model may include the following process flow:

A) Initialization: Network parameters are initialized before training begins.

B) Epoch Loop: The training process iterates over a number of epochs.

C) Sample Loop: For each training sample:

C1) Forward Pass: Backproject the projections, concatenate the volumes, and compute the network's output.

C2) Loss Computation: Calculate the loss between the network's output and the true CT volume.

C3) Backward Pass: Compute the gradients of the loss with respect to the network parameters.

C4) Parameter Update: Update the network parameters using an optimization algorithm (e.g., stochastic gradient descent).

D) Output: After training, the optimized network parameters define the trained model Uθ.

Figure 25A:
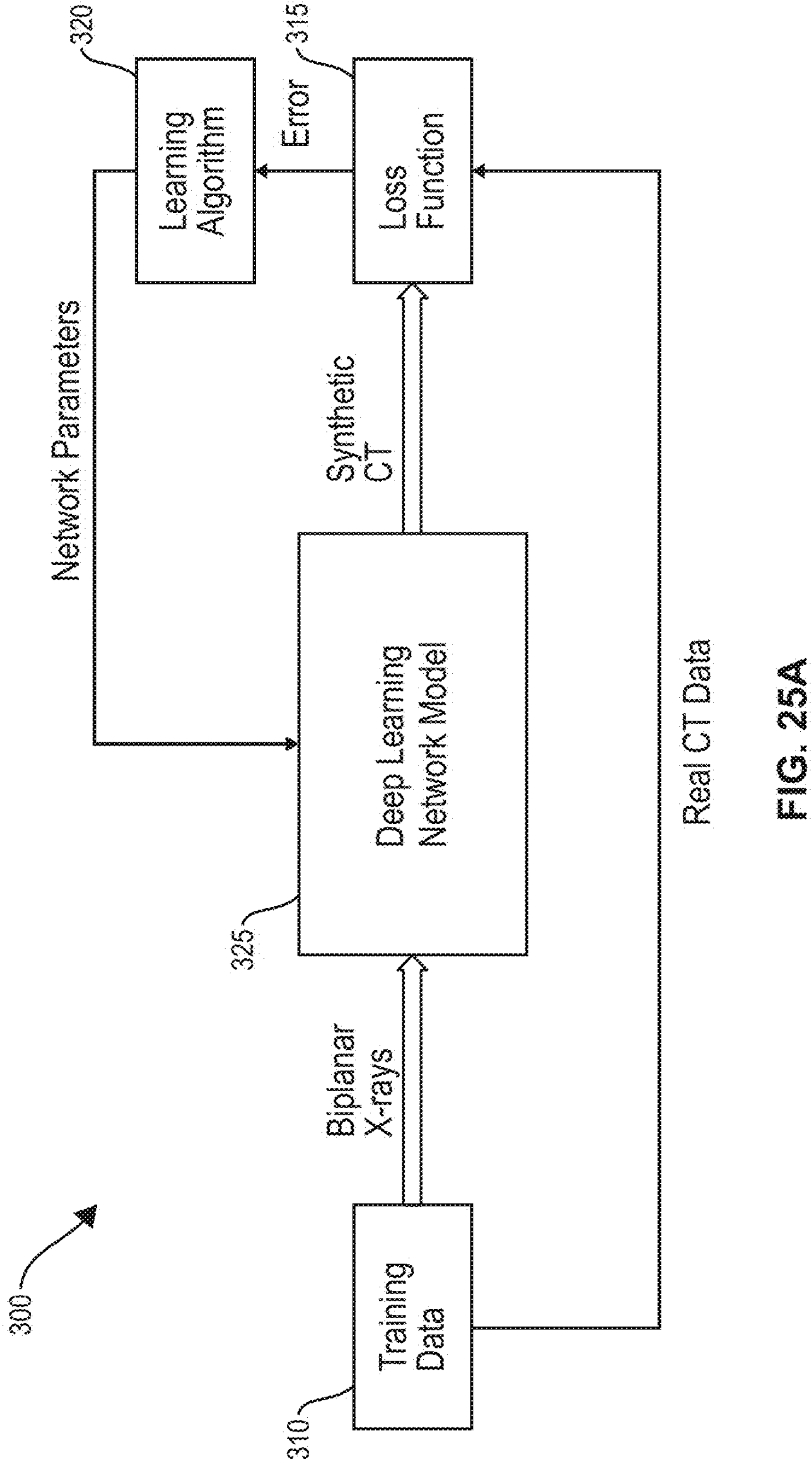
FIG. 25A is a conceptual illustration of a computer system suitable for training of a deep learning network model in accordance with the disclosure.

FIG. 25A is a conceptual illustration of a computer system 300 suitable for training of a deep learning network model 325 in accordance with the disclosure. Specifically training data 310 is provided to a deep learning model 300 and simultaneously provided to at loss function module 315. The training data 310 may be in the form of real CT images and scans as provided to loss function module 315 or biplanar x-rays as provided to deep learning network 325. The output of the deep learning network 325 is synthetic CT images which are provided to the loss function module 310. The output of loss function module 310 is an value representing the magnitude of an error which is provided to a learning algorithm module 320. The output of learning algorithm module 320 in the form of network parameters, e.g. weight values or coefficients, are provided back to the deep learning module 325 for further refinement of the model.

Training involves comparing the decoded 3D volume with an original CT scan of the same patient. The CT scan serves as a ground truth or reference for the 3D structure that the system aims to reconstruct. By comparing the decoded volume with the CT scan, the system can identify discrepancies and errors in the reconstruction.

The system employs loss functions to quantify the differences between the reconstructed volume and the reference CT scan. These loss functions are crucial in guiding the training process, providing a metric for the system to understand and minimize errors. Gradient computation is then performed based on these loss functions, allowing the system to adjust and refine the encoder and decoder models.

The training process is iterative. The system repeatedly encodes, back-projects, decodes, and compares the results to the reference CT scans, each time adjusting the models based on the computed gradients. This iterative process continues until the encoder and decoder have sufficiently learned how to accurately generate the 3D volume from the X-ray images.

For the system to learn effectively and generalize well to new cases, it is important to train on a large and varied dataset of CT scans and their associated X-rays. Such dataset should include a wide range of cases, covering different anatomical regions, patient demographics, and pathological conditions. The diversity in the training data ensures that the system can handle a variety of real-world scenarios and reconstruct accurate 3D volumes across different patient cases.

The proposed framework is flexible and can incorporate different deep learning architectures based on the specific requirements of the task. The framework allows for the substitution of the neural network component without altering the overall pipeline, facilitating experimentation with various architectures, i.e. modularity. Hyperparameters and architectural components can be customized to balance trade-offs between computational efficiency and reconstruction accuracy, i.e. customization. The disclosed system can be scaled to incorporate additional projections or channels, accommodating more complex models if more data becomes available, i.e. scalability.

In embodiments, the U-Net architecture is suitable due to its Encoder-Decoder structure comprising a contracting path (encoder) that captures context and an expansive path (decoder) that enables precise localization. The U-Net architecture utilizes skip connections wherein feature maps from the encoder are combined with corresponding decoder layers, preserving spatial information. Further, the U-Net architecture utilizes 3D convolutions wherein the network operates on volumetric data, using 3D convolutional layers to capture spatial relationships in all three dimensions.

Figure 17:
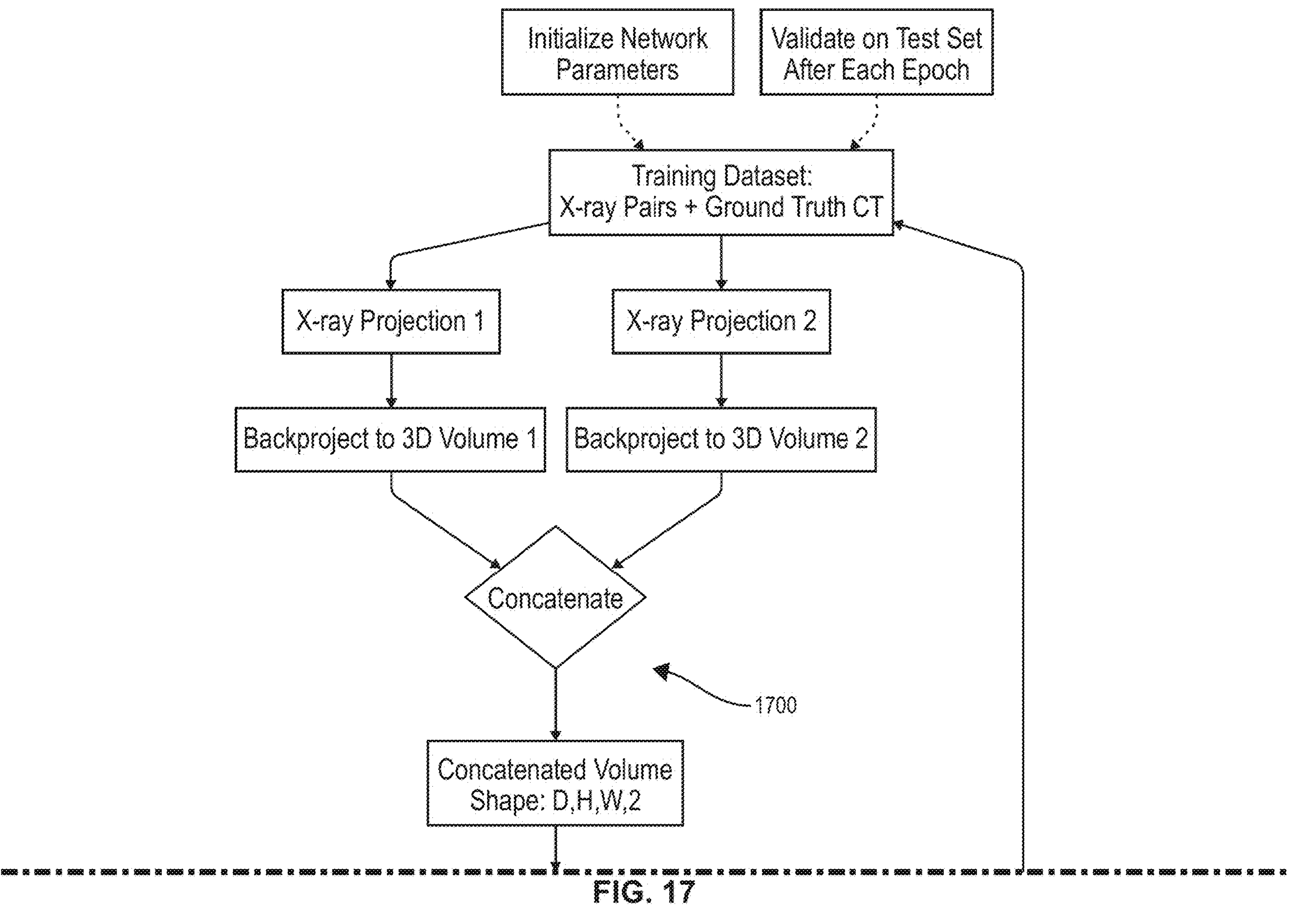
FIG. 17 conceptually illustrates a 3D U-Net training process in accordance with the disclosure.
Figure 17:
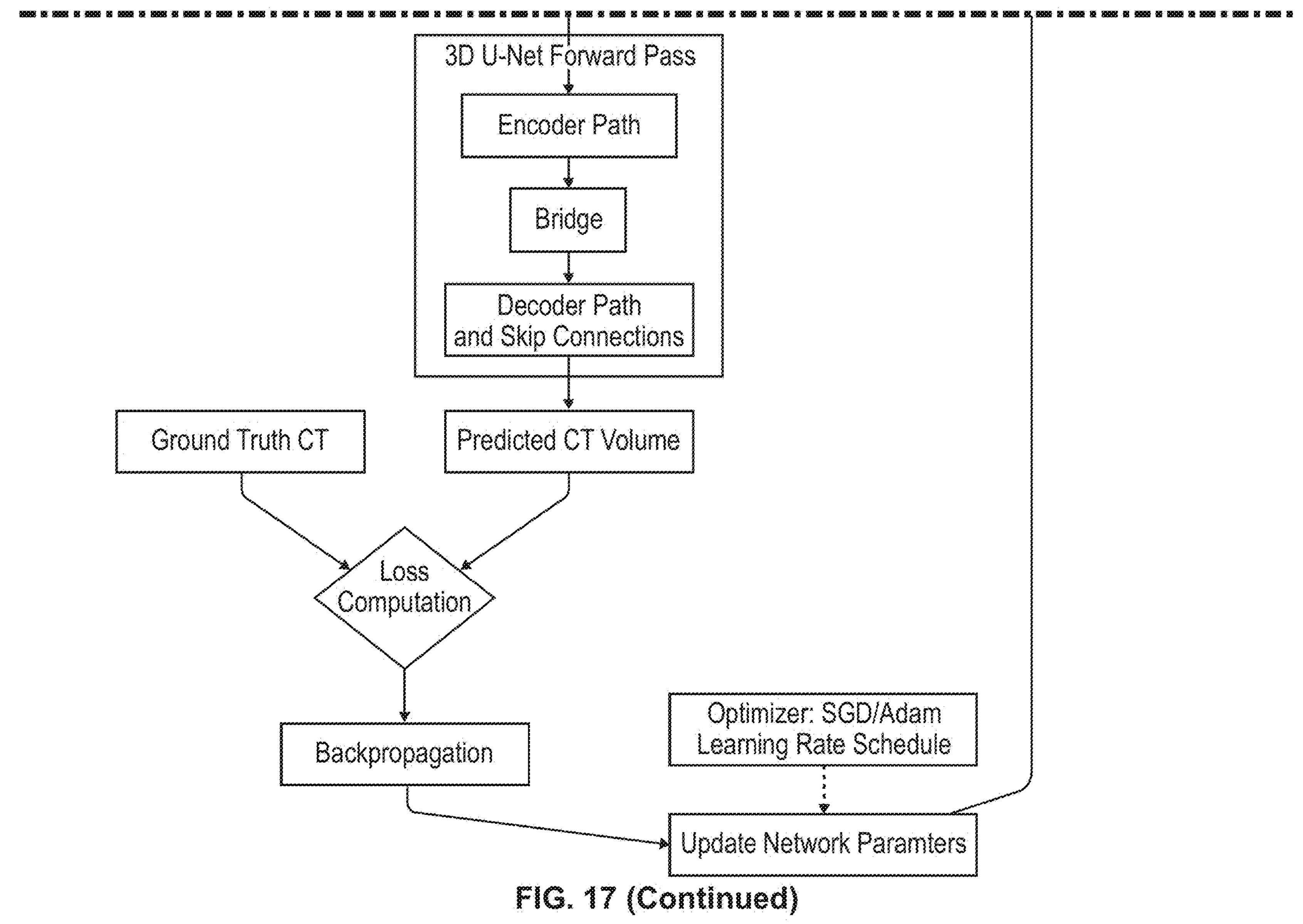

FIGS. 17-24B illustrate variations of process flows, particularly with regard to the encoder-decoder functions and dimensions of the respective data, for reconstruction a 3D volume in accordance with the disclosure. FIG. 17 conceptually illustrate a training process flow 1700 of a 3D U-Net forward pass training process where encoding and decoding occur after the X-ray images are back projected and concatenated into a 3D Volume. In this process flow the ground truth CD and volume output from the 3D U-Net are used to perform a loss computation prior to final back projection.

Figure 18:
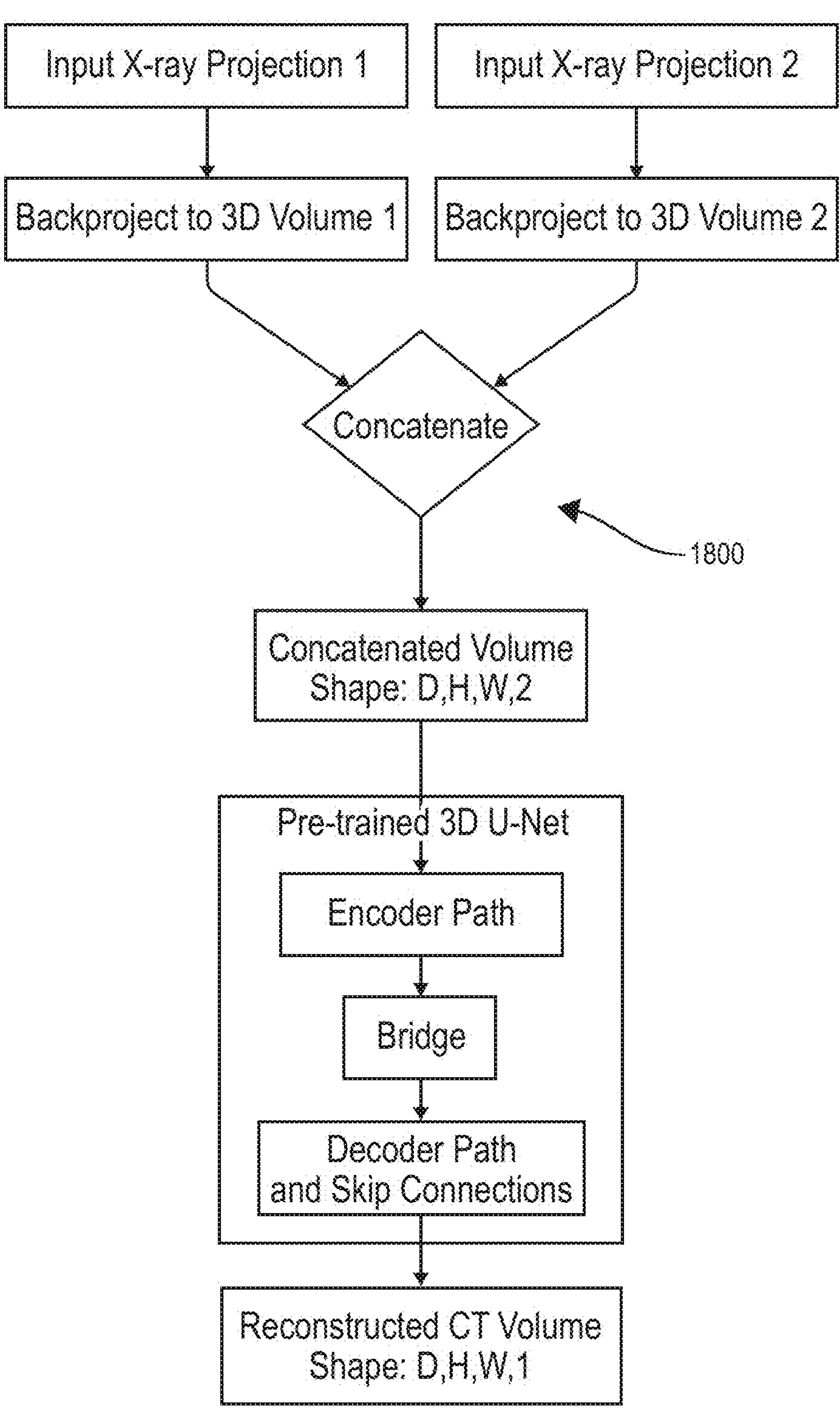
FIG. 18 conceptually illustrates a 3D U-Net interference process in accordance with the disclosure.
Figure 19:
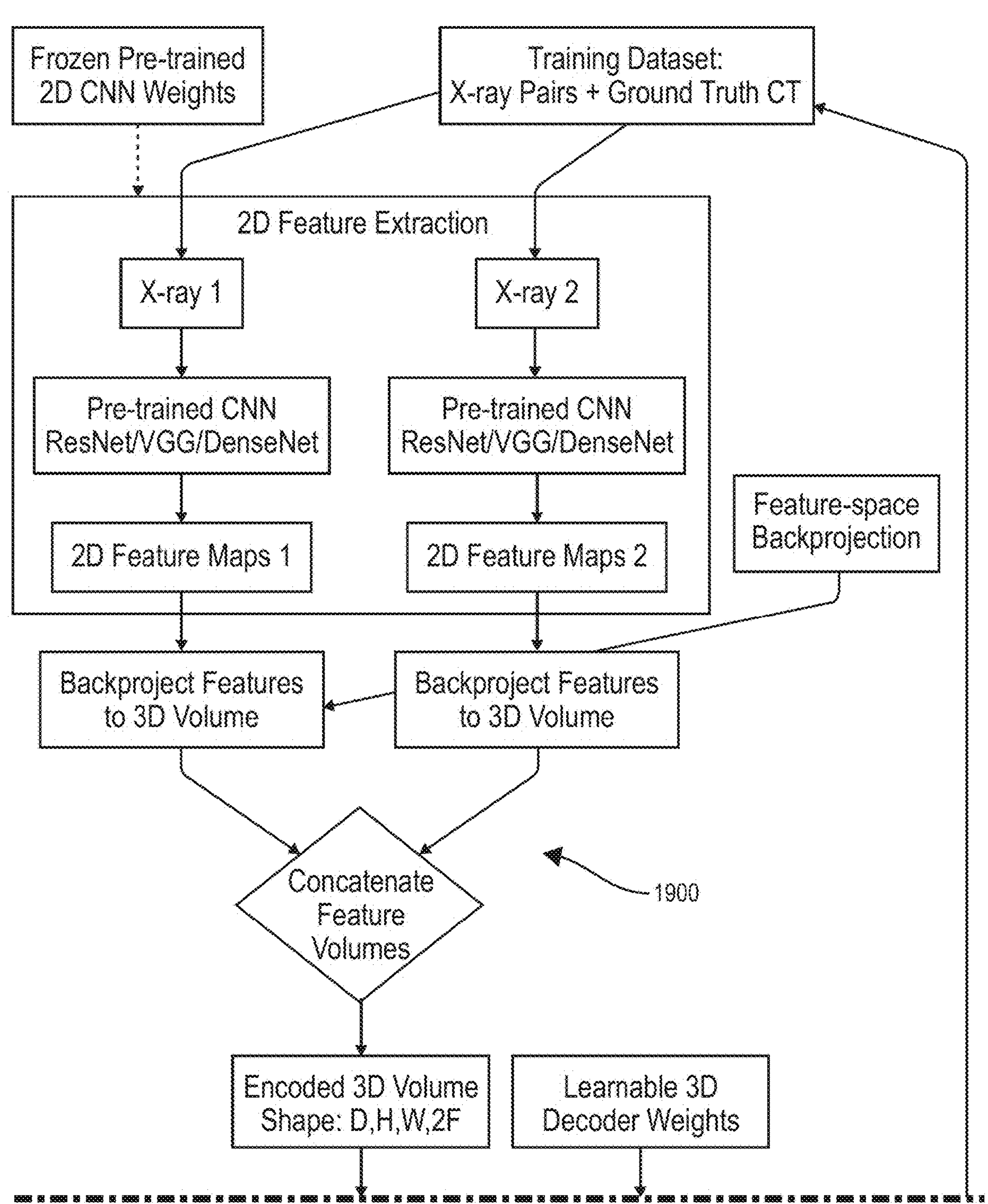
FIG. 19 conceptually illustrates a 2D encoding and 3D decoding training process in accordance with the disclosure.
Figure 19:
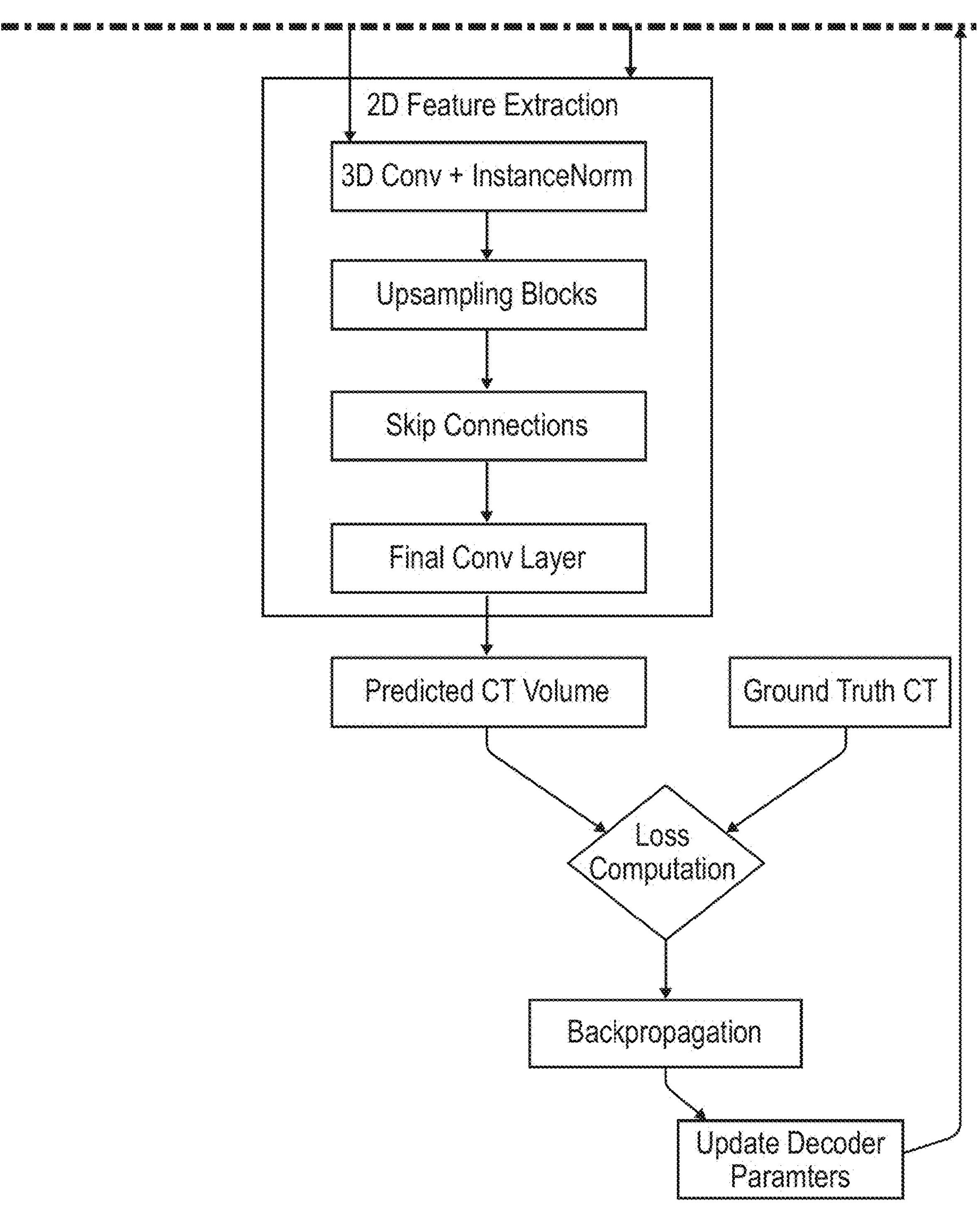

FIG. 18 conceptually illustrates an inference process flow 1800 similar to process flow 1700. As illustrated in FIG. 18, input x-ray projection 1 and input x-ray projection 2 are back projected to 3D Volumes 1 and 2, respectively, and concatenated into a combined volume. There after the output of the combined volume is provided to a pretrained 3D U-Net, the output of which functions as the reconstructed 3D CT volume.

FIGS. 19A-B conceptually illustrate a training process flow 1900 having 2D encoding and 3D decoding where 2D encoding on each X-ray is followed by, back projection into two 3D encoded volumes, concatenation of the encoded volumes, and 3D decoding into final CT. This process flow uses a 2D feature extractor on the X-ray images with the extracted feature(s) then back projected into a concatenated 3D volume for subsequent 3D decoding and loss computation.

Figure 20:
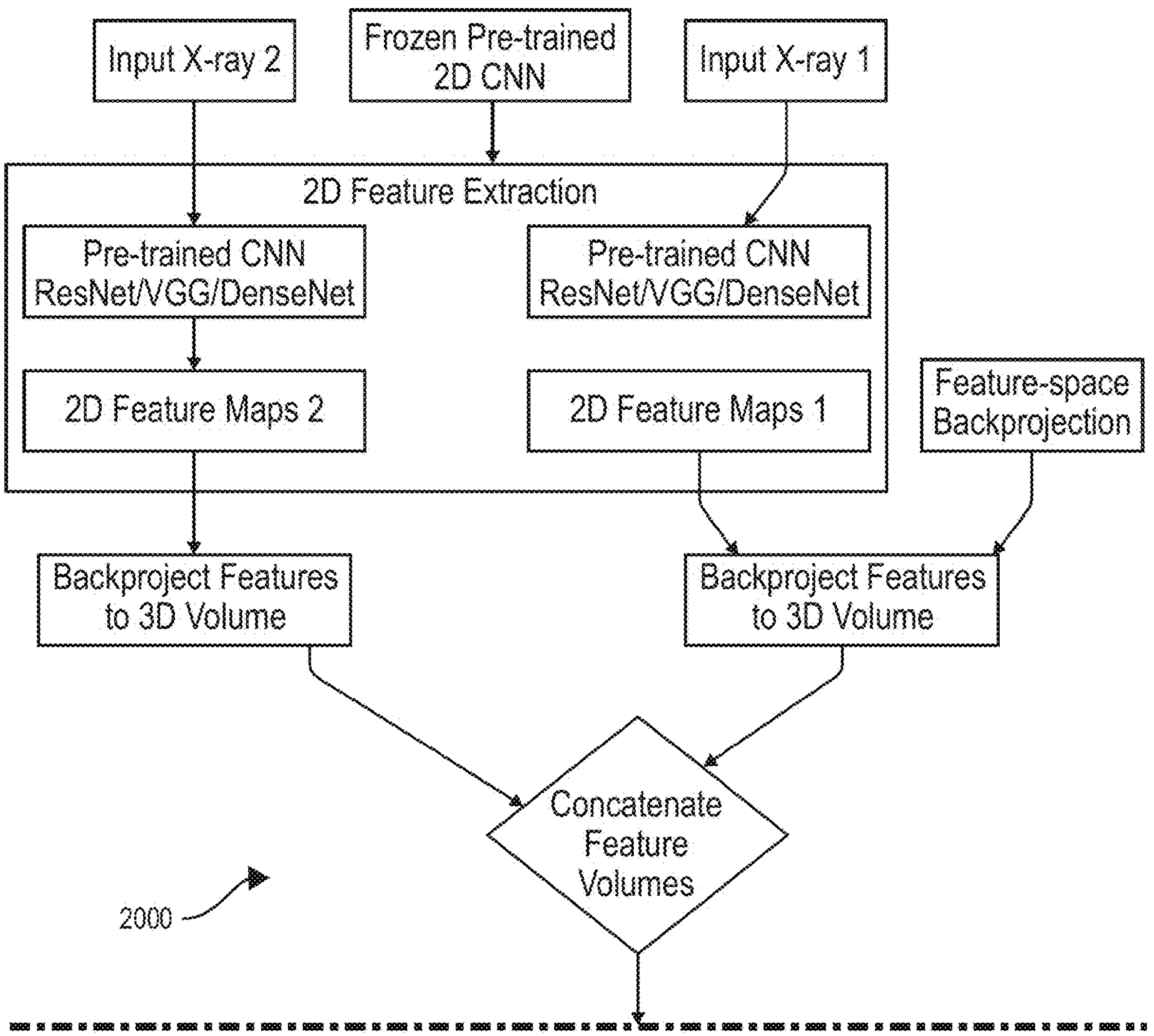
FIG. 20 conceptually illustrates a 2D encoding and 3D decoding training process in accordance with the disclosure.
Figure 20:
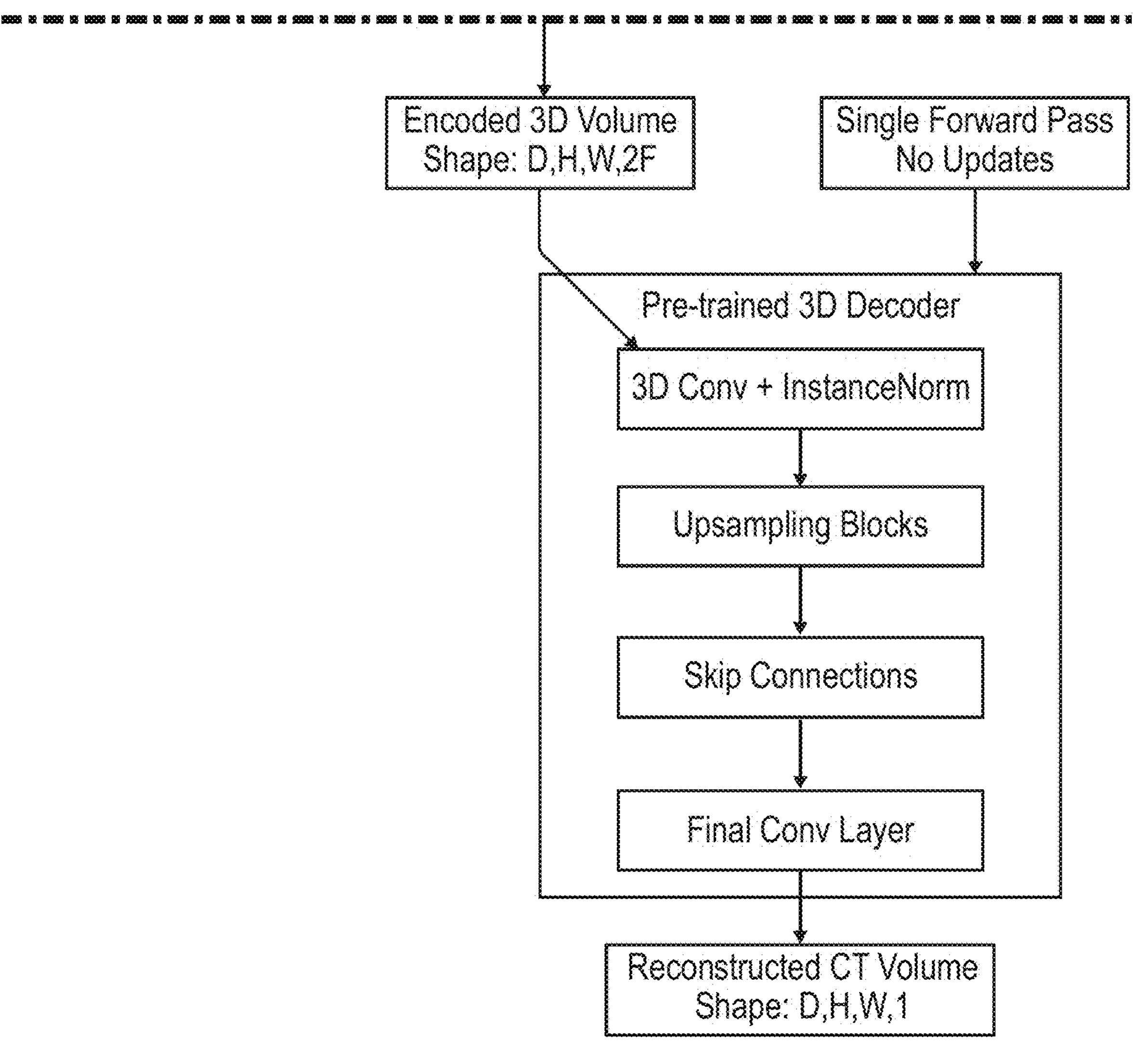

FIG. 20 conceptually illustrates an inference process flow 2000 similar to process flow 1900, except that un addition to input from X-rays 1 and X-ray 2, Frozen pre-trained 2D convolution Network outputs are provided to a 2D feature extraction process, the output of which is used to back project features to first and second respective 3D volumes, which thereafter are concatenated into a 3D volume.

Figure 21:
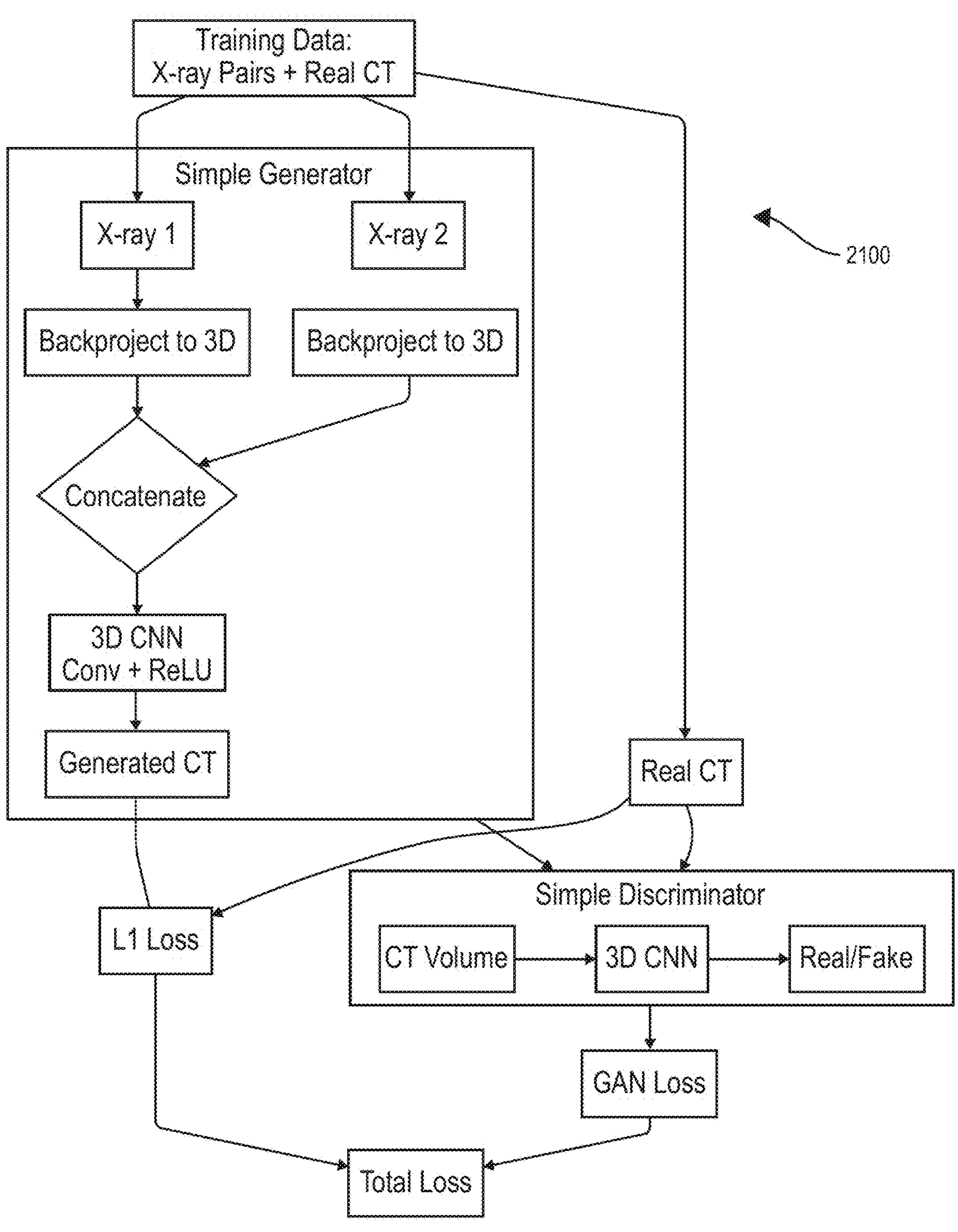
FIG. 21 conceptually illustrates a Generative Adversarial Network (GAN) training process in accordance with the disclosure.

FIG. 21 conceptually illustrates a training process flow 2100 of a Generative Adversarial Network (GAN) where a GAN version of training implements Method 1 for generator and a separate 3D discriminator then a comparison. As illustrated in FIG. 21, training data is provided to both a simple generator and a simple discriminator. In addition, the simple generator is provided with both X-rays 1 and 2, which are projected into separate 3D volumes and concatenated into a 3D convolution network volume which generates a CT synthetic CT volume. The synthetic CT volume output is provided to the simple discriminator along with the real CT scans. The output of the simple discriminator is a gain loss value which when combined with the loss from the simple generator determines a total loss.

Figure 22:
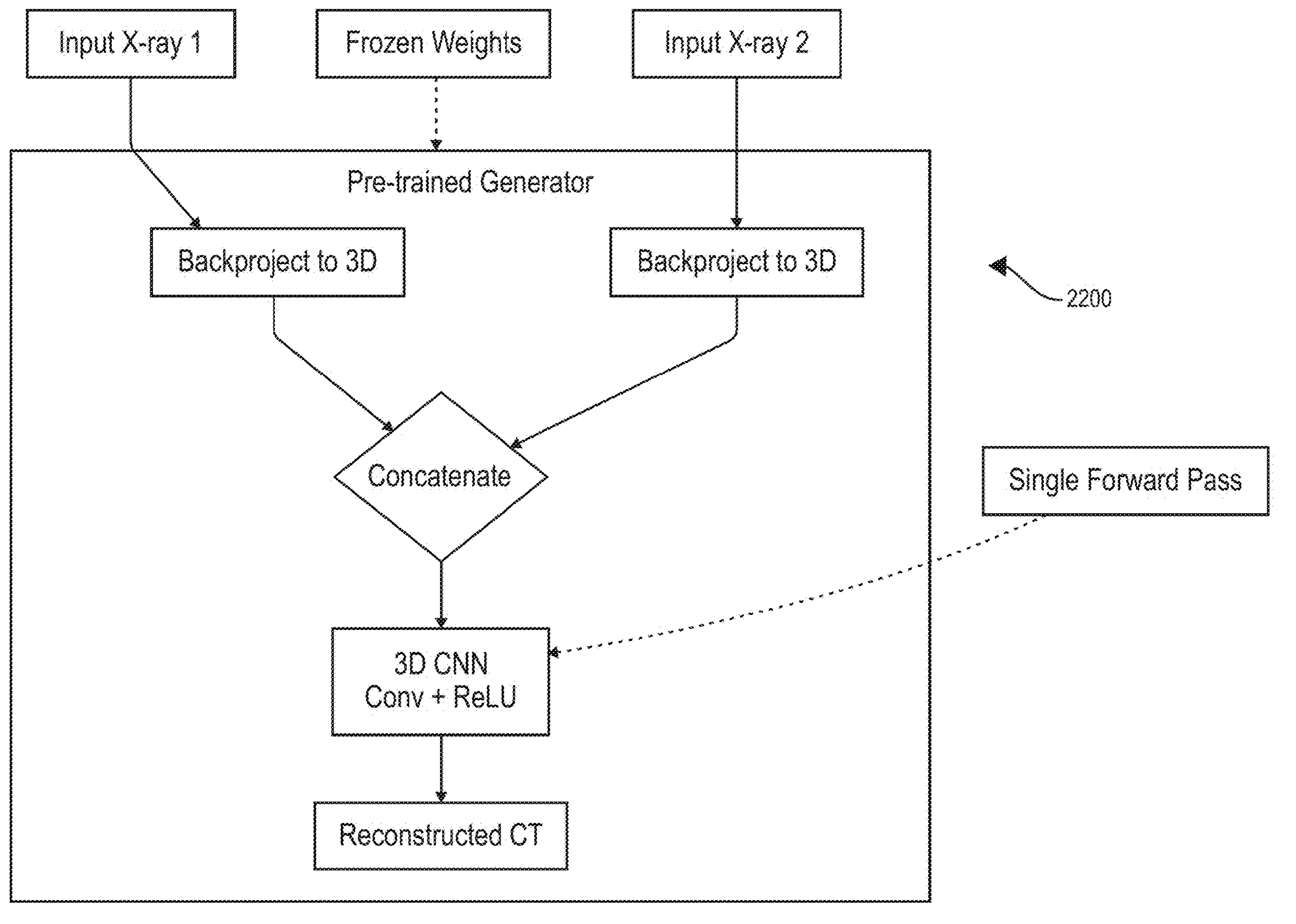
FIG. 22 conceptually illustrates a Generative Adversarial Network inference process in accordance with the disclosure.

FIG. 22 conceptually illustrates an inference process flow 2200 similar to the process flow 2100. As illustrated in FIG. 22, input X-ray 1, input X-ray 2 and frozen weights are provided to a pre-trained generator. The X-ray inputs are back projected to separate 3D volumes which are then concatenated into a combined volume and provided to a 3D Convolutional Neural Networks, the output which comprises a restructured 3D CT volume.

Figure 23A:
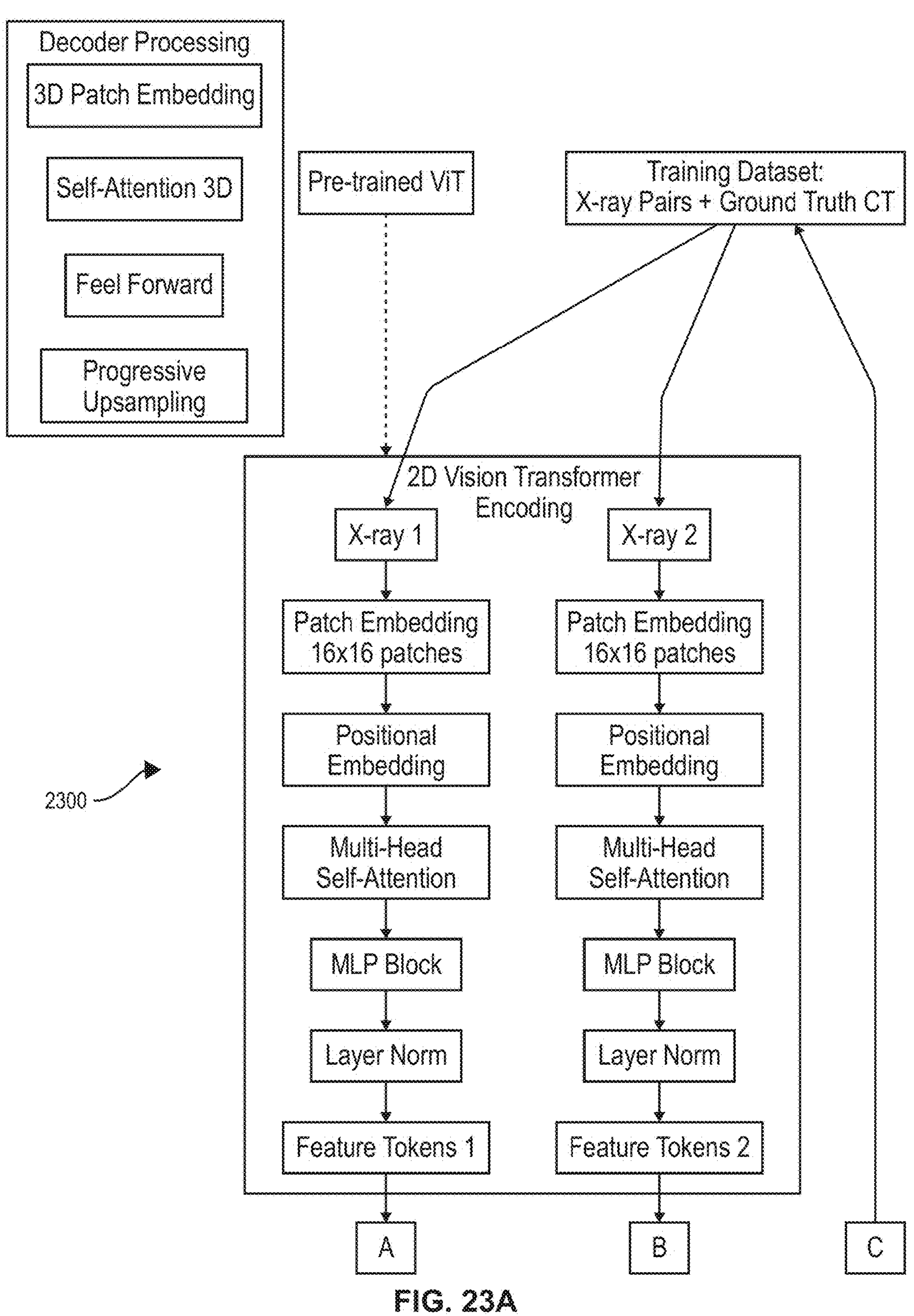
FIGS. 23A-B conceptually illustrate a 2D and 3D Vision Transformer (ViT) training process in accordance with the disclosure.
Figure 23B:
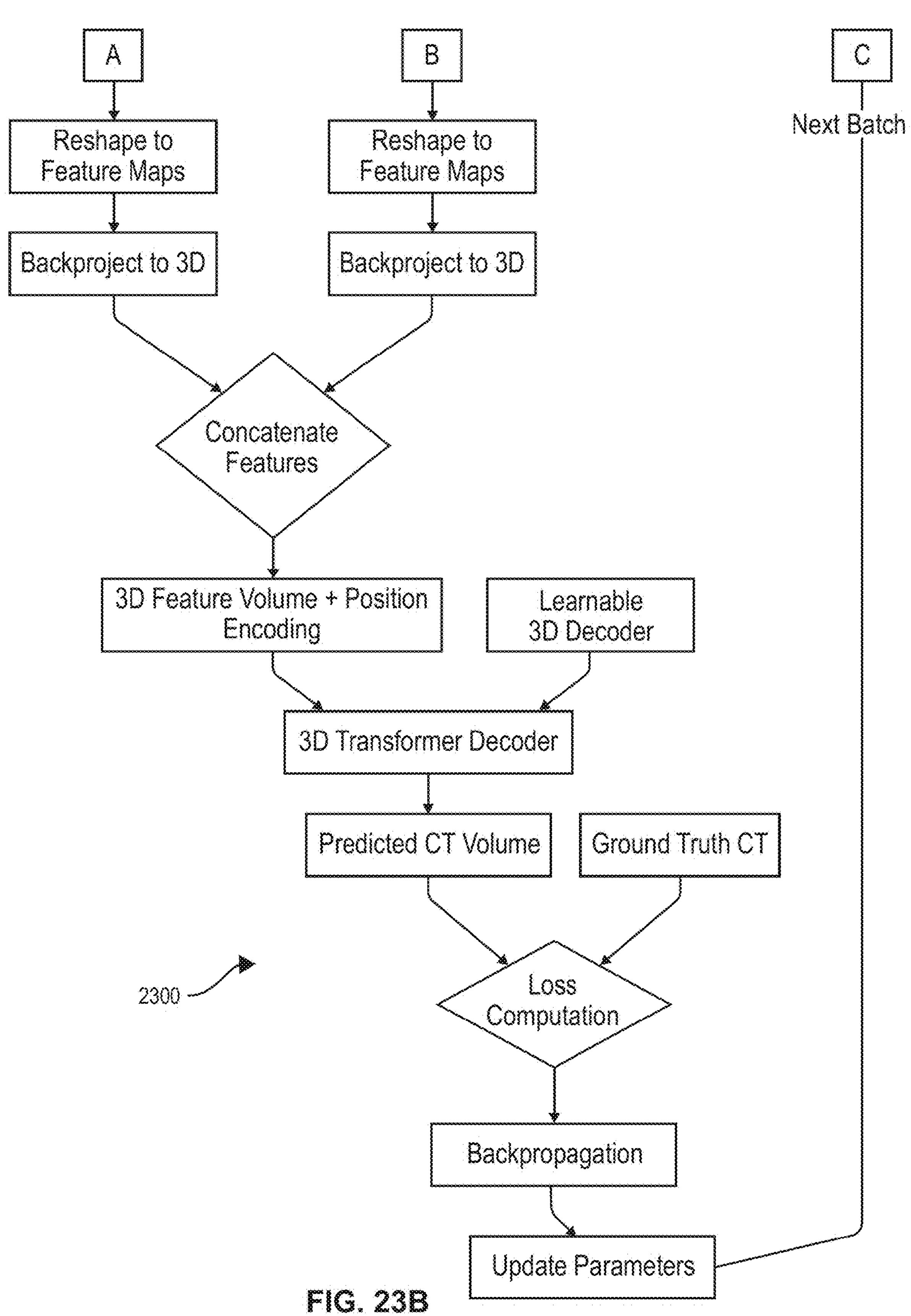
Figure 24A:
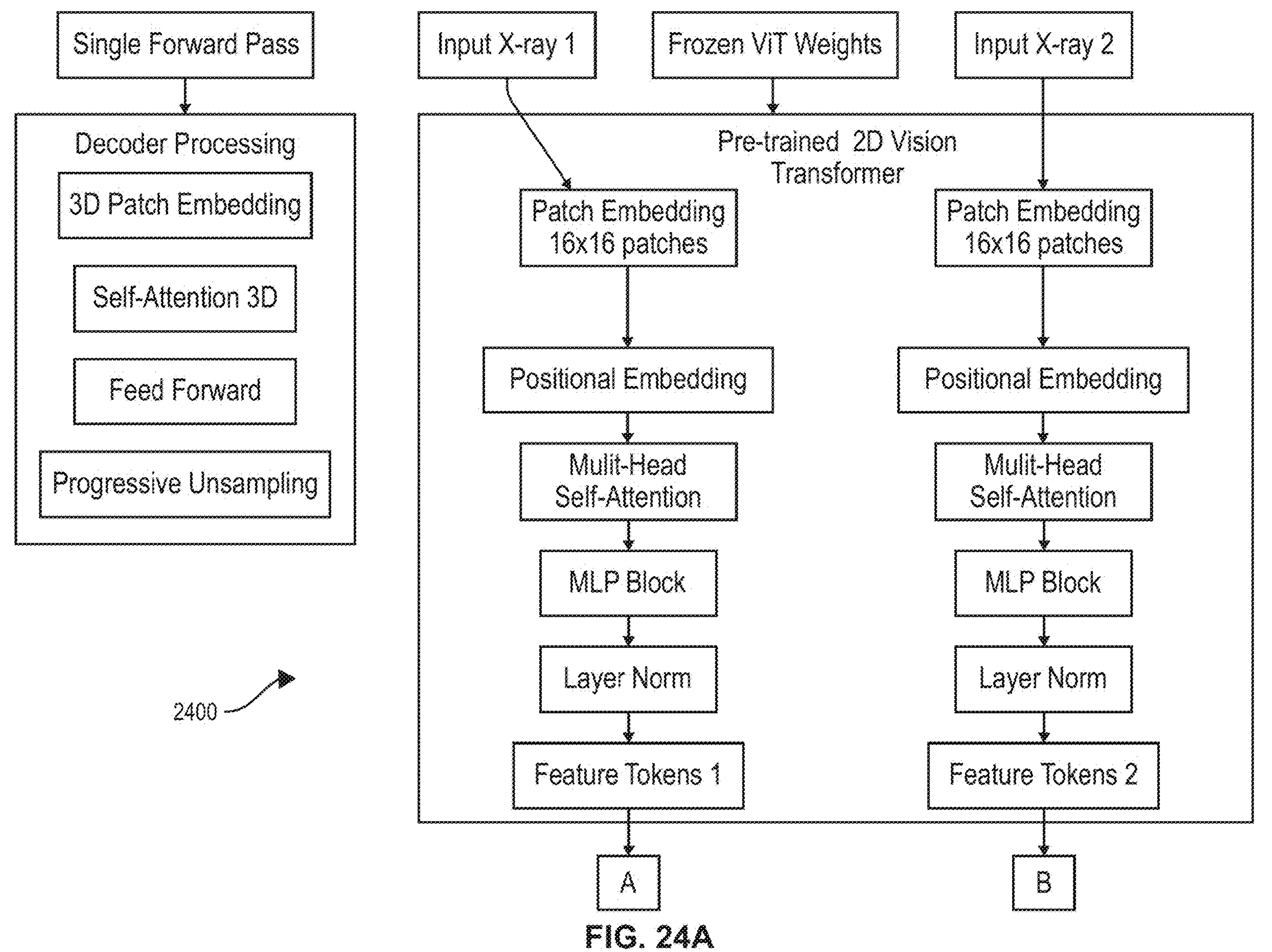
FIGS. 24A-B conceptually illustrate a 2D and 3D Vision Transformer Inference process in accordance with the disclosure.
Figure 24B:
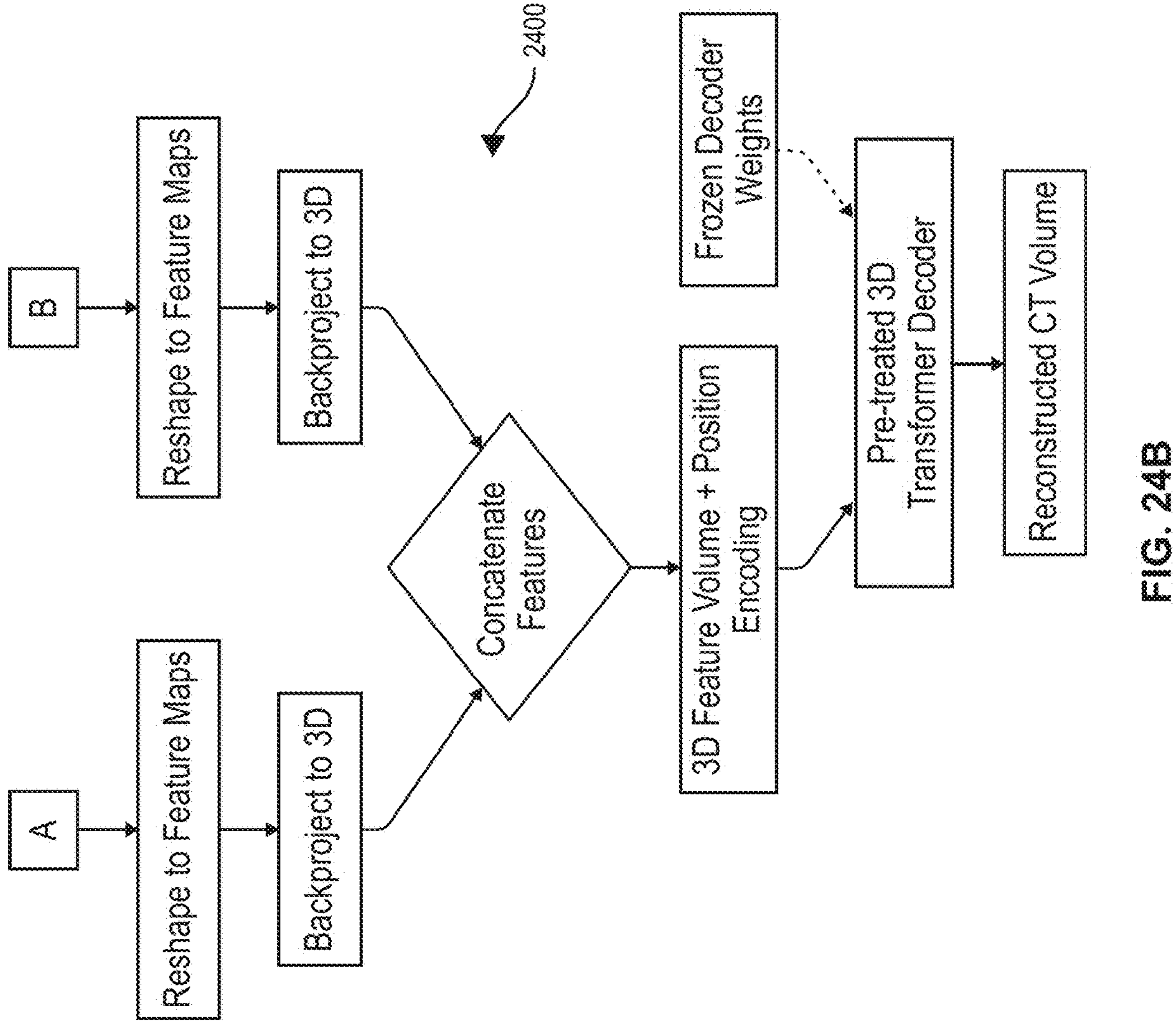

FIGS. 23A-B conceptually illustrate a training process flow 2300 of 2D and 3D Vision Transformer (ViT) that implements a Method 2 using vision transformers rather than Convolutional Neural Networks (CNNs). FIGS. 24A-B conceptually illustrate a transformer inference process flow 2400 similar to the process flow 2300 with a 2D and 3D Vision Transformer Inference.

Although the exemplary embodiment disclosed herein employs the U-Net architecture in this study, other deep learning network architectures such as DenseNet, V-Net, and U-Nets with attention mechanisms, may also be utilized to train the model. These architectures may offer advantages in terms of feature extraction, model depth, and attention to relevant regions, potentially improving reconstruction quality. By learning from a large dataset of biplanar X-rays and their corresponding CT scans, the model effectively overcomes the limitations imposed by the limited angle theorem. Given sufficient training data, the learned model can approximate the true CT reconstruction function, even for biplanar X-rays not seen during training. This demonstrates the potential of deep learning to transcend classical limitations in tomographic reconstruction imposed by insufficient projection data.

Figure 25B:
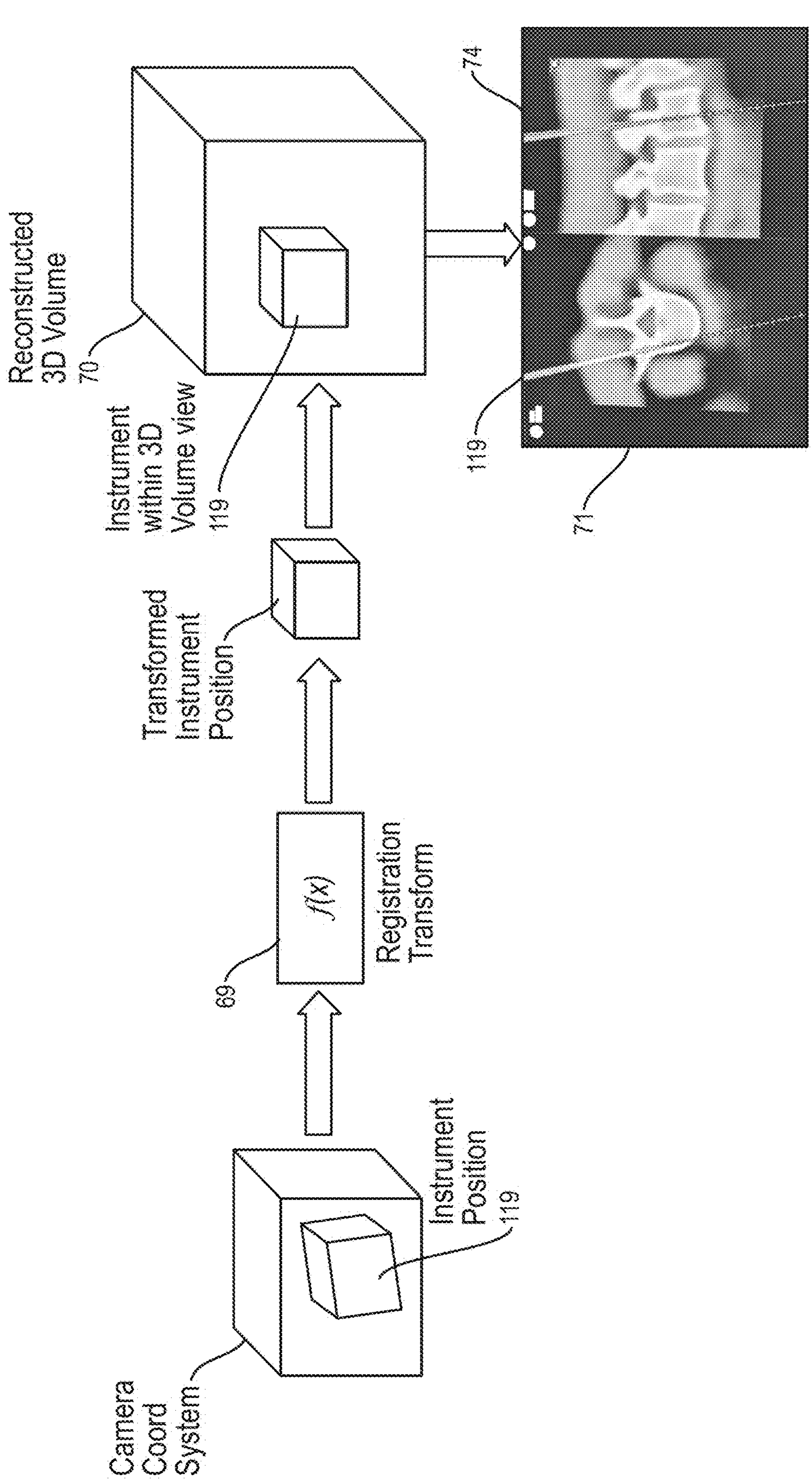
FIG. 25B is a high level conceptual illustration of the surgical navigation process in accordance with the disclosure.

FIG. 25B is a high level conceptual illustration of the surgical navigation process in accordance with the disclosure. Specifically, an instrument 119 is recognized by the system 110, with or without markers, within the camera coordinate system and is transformed by the registration transform 69 to a set of coordinates which are within the bounds of the reconstructed volume 70. Thereafter an image of instrument 119 is overlayed over planar images 71 and 74 from the reconstructed volume 70 is used to along with and an image of instrument 119 is overlayed thereon for surgical navigation guidance.

Figure 26:
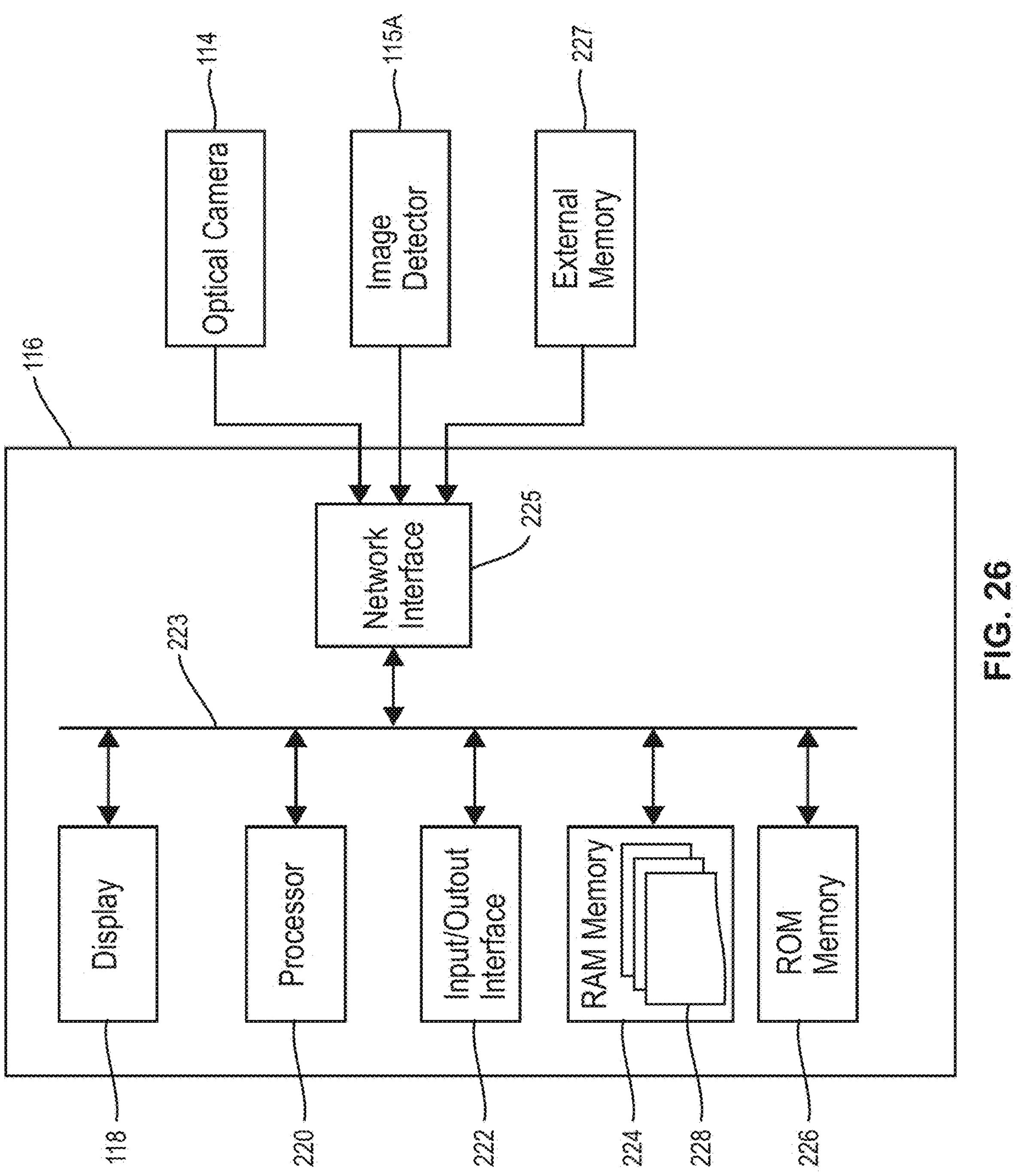
FIG. 26 is a conceptual illustration of a computer system suitable for use with the disclosed system and methods.

The methods described herein may be implemented on a computer 116 using well-known computer processors, memory units, storage devices, computer software, and other components. A high-level block diagram of such a computer is illustrated in FIG. 26. In embodiments, computer 116 comprises display 118, processor 220, I/O interface 222, memories 224 and 226, and network interface 225, all operatively interconnected by bus 223. Network interface 225 operatively connects cameras 114, radiographic image detector 115A, and external memory 227 to the other components of computer 116, as illustrated in FIG. 26. Processor 220 controls the overall operation of the computer 116 by executing software modules or applications comprising computer program instructions 288 which define such operation functionality. The computer program instructions 228 may be stored directly in memory 224 or in an external storage device 227 (e.g., magnetic disk) and loaded into memory 224 when execution of the computer program instructions is desired. Thus, the processes described herein may be defined by the computer program instructions stored in the memory 224 and/or storage 227 and controlled by the processor 220 executing the computer program instructions. ROM memory 226 typically contains computer program instructions comprising the operating system and basic input/output system firmware to provide runtime services for the operating and programs and to perform hardware initialization during power on startup processes.

A radiographic image detector 115A, such as a CT scanner, C-arm CT scanner, or X-ray scanner, or other radiographic image detector, can be connected to the computer 116 via network interface 225 to input image data to the computer 116. It is possible to implement the radiographic image detector 115A and the computer 116 as one device. It is also possible that radiographic image detector 115A and the computer 116 communicate wirelessly through a network infrastructure. In embodiments, the computer 116 can be located remotely with respect to the radiographic image detector 115A and the process described herein can be performed as part of a server or cloud based service. In this case, the process may be performed on a single computer or distributed between multiple networked computers. The computer 116 also includes one or more network interfaces 125 for communicating with other devices via a network. The computer 116 also includes other input/output devices 222 that enable user interaction with the computer 116 (e.g., display, keyboard, mouse, speakers, joystick controllers, etc.). One skilled in the art will recognize that an implementation of an actual computer could contain other components as well, and that FIG. 26 is a high level representation of some of the components of such a computer for illustrative purposes.

In light of the foregoing description, the reader will appreciate the following benefit advantages of the disclosed system and methods. The numerous advantages of the disclosed system and methods include the following. The disclosed system and method address the problem of limited projection data. As disclosed herein, by using deep learning, the limitations of traditional reconstruction methods that require numerous projections over a wide angular range are overcome. The disclosed system and method address the problem of limited pose estimation accuracy. As disclosed herein, integration of optical tracking and camera calibration provides precise pose information needed for accurate reconstruction and instrument tracking. The disclosed system and method address the problem of automatic instrument registration. As disclosed herein, enabling automatic registration enhances the feasibility of minimally invasive procedures, reducing the need for exposing the patient's anatomy. The disclosed system and method address the problem of marker-less instrument tracking. As disclosed herein, utilizing object recognition and 3D localization algorithms, instruments can be tracked without the need for attached reference arrays, simplifying the surgical workflow. The disclosed system and method address the problem of distortion correction. As disclosed herein, correcting non-linear distortions in the X-ray images improves the accuracy of back-projection and reconstruction, especially when using image intensifier systems. The disclosed system and method address the problem of voxel grid alignment. As disclosed, defining the voxel grid using the registration transform ensures that the reconstructed volume is in the patient coordinate system and consistent with the instrument tracking system. This alignment also ensures that the grid points fall within the field of view of the X-ray images when projected, to ensure effective reconstruction. The disclosed system and method address the problem of minimal radiation exposure. As disclosed herein, capturing only two X-ray images reduces patient exposure to radiation compared to traditional CT scanning. The disclosed system and method address the problem of integration of modalities. As disclosed herein, combining optical tracking with radiographic imaging leverages the strengths of both modalities for enhanced imaging capabilities. The disclosed system and method address the problem of enhanced surgical navigation. As disclosed herein, the ability to track surgical instruments within the reconstructed volume provides surgeons with real-time, precise guidance, improving surgical outcomes.

Although the systems and methods disclosed herein have been described with reference to patient anatomy and surgical navigation procedures, their applicability is not limited to the same. Any of the systems and methods disclosed herein may be utilized in other situations, including industrial control, package or baggage handling, or any other environments in which the near real-time position and tracking of objects within a volume is required.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

At various places in the present specification, values are disclosed in groups or in ranges. It is specifically intended that the description includes each and every individual sub-combination of the members of such groups and ranges and any combination of the various endpoints of such groups or ranges. For example, an integer in the range of 0) to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

For purposes of clarity and a concise description, features are described herein as part of the same or separate embodiments, however, it will be appreciated that scope of the concepts may include embodiments having combinations of all or some of the features described herein. Further, terms such as "first," "second," "top," "bottom," "front," "rear," "side," and other are used for reference purposes only and are not meany to be limiting.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to an example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A." and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A method for constructing a three-dimensional (3D) volume from a set of two or more medical images, the method comprising:

A) acquiring two or more biplanar radiographic images with an X-ray imaging device;

B) calibrating each of the biplanar radiographic images both intrinsically and extrinsically in relation to a common coordinate system;

C) encoding the calibrated images using a machine learning or deep learning algorithm executing on a processor;

D) back-projecting the encoded images into separate respective volumes and concatenating the separate respective volumes into a combined volume along a new dimension within the common coordinate system based on known relative 3D poses; and E) decoding the back-projected combined volume to reconstruct the 3D volume using a pretrained 3D neural network.

2. The method of claim 1, wherein the machine learning or deep learning algorithm is trained on a dataset comprising CT scans and corresponding X-ray images.

3. A computer program product comprising a non-transitory computer-readable medium storing instruction that, when executed by a processor, cause the processor to perform a method for constructing a three-dimensional (3D) volume from a set of two or more medical images, the method comprising:

A) acquiring two or more biplanar radiographic images with an X-ray imaging device;

B) calibrating each of the biplanar radiographic images both intrinsically and extrinsically in relation to a common coordinate system;

C) encoding the calibrated images using a machine learning or deep learning algorithm executing on a processor;

D) back-projecting the encoded images into separate respective volumes and concatenating the separate respective volumes into a combined volume along a new dimension within the common coordinate system based on known relative 3D poses; and E) decoding the back-projected combined volume to reconstruct the 3D volume using a pretrained 3D neural network.

4. The method of claim 3, wherein the machine learning or deep learning algorithm is trained on a dataset comprising CT scans and corresponding X-ray images.

5. The computer program product of claim 3, further comprising:

F) iteratively refining the encoding and decoding algorithms using a training process by comparing the reconstructed 3D volume with pre-existing corresponding computed tomography (CT) scans.

* * * * *